US008367851B2

(12) United States Patent
Lilga et al.

(10) Patent No.: US 8,367,851 B2
(45) Date of Patent: *Feb. 5, 2013

(54) HYDROXYMETHYLFURFURAL REDUCTION METHODS AND METHODS OF PRODUCING FURANDIMETHANOL

(75) Inventors: Michael A. Lilga, Richland, WA (US); Richard T. Hallen, Richland, WA (US); James F. White, Richland, WA (US); Michel J. Gray, Mesa, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/173,942

(22) Filed: Jun. 30, 2011

(65) Prior Publication Data

US 2011/0306780 A1  Dec. 15, 2011

Related U.S. Application Data

(63) Continuation of application No. 11/760,634, filed on Jun. 8, 2007, now Pat. No. 7,994,347.

(60) Provisional application No. 60/804,409, filed on Jun. 9, 2006.

(51) Int. Cl.
*C07D 307/02* (2006.01)
(52) U.S. Cl. ........................ 549/503; 549/502
(58) Field of Classification Search .................. 549/502, 549/503
See application file for complete search history.

(56) References Cited

U.S. PATENT DOCUMENTS

| | | | |
|---|---|---|---|
| 1,903,850 A | 4/1933 | Peters, Jr. | |
| 1,906,873 A | 5/1933 | Peters, Jr. | |
| 2,077,409 A | 4/1937 | Graves | |
| 2,077,422 A | 4/1937 | Lazier | |
| 2,082,025 A | 6/1937 | Peters, Jr. | |
| 2,094,975 A | 10/1937 | Adkins et al. | |
| 2,487,054 A | 11/1949 | Howk | |
| 2,763,666 A | 9/1956 | Mastagli | |
| 3,040,062 A | 6/1962 | Hales | |
| 3,083,236 A | 3/1963 | Utne et al. | |
| 3,847,952 A | 11/1974 | Smirnov et al. | |
| 4,182,721 A | 1/1980 | De Thomas et al. | |
| 4,185,022 A | 1/1980 | Kozinski | |
| 4,251,396 A | 2/1981 | Frainier et al. | |
| 4,261,905 A | 4/1981 | Preobrazhenskaya et al. | |
| 4,302,397 A | 11/1981 | Frainier et al. | |
| 4,335,049 A | 6/1982 | Hamada et al. | |
| 4,400,468 A | 8/1983 | Faber | |
| 4,728,671 A | 3/1988 | Hinnekens | |
| 4,764,627 A | 8/1988 | Diebold et al. | |
| 4,780,552 A | 10/1988 | Wambach et al. | |
| 5,591,873 A | 1/1997 | Bankmann et al. | |
| 6,479,677 B1 | 11/2002 | Ahmed | |
| 7,994,347 B2 * | 8/2011 | Lilga et al. ............ | 549/503 |

FOREIGN PATENT DOCUMENTS

| | | |
|---|---|---|
| EP | 0096913 A1 | 12/1983 |
| FR | 2556344 A1 | 12/1983 |
| JP | 59190984 | 10/1984 |

OTHER PUBLICATIONS

Morikawa, "Reduction of 5-Hydroxymethylfurfural", Noguchi Kenkyusho Jiho (1980), (23), 39-44.
Balandin et al., "Selective Hydrogenation of Furan Compounds", Doklady Akademii Nauk SSSR (1955), 100, 917-20.
Schiavo et al., "Hydrogenation Catalytique du 5-hydroxymethylfurfural en milieu aqueux", Bull. Soc. Chim. Fr. (1991) 704-711.
Vaidya et al., "Kinetics of Liquid-Phase Hydrogenation of Furfuraldehyde to Furfuryl Alcohol over a PUC Catalyst", American Chemical Society, Jun. 11, 2003, 5 pages.
Liaw et al., "Catalysis of CuB/SiO2 Catalysts for Hydrogenation of Furfural, Crotonaldehyde, and Citral", J. China Inst. Chem. Engrs., vol. 34, No. 6, 667-674, Oct. 29, 2003.
PCT/US2007/070802, Oct. 12, 2008, IPRP.
PCT/US2007/070802, Nov. 26, 2007, Search Report.
PCT/US2007/070802, Nov. 11, 2007, Written Opinion.
Lewkowski, "Synthesis, Chemistry and Applications of 5-Hydroxymethyl-furfural and Its Derivatives", General Papers Arkivoc 2001 (i) 17-54. ISSN 1424-6376.
Moye et al., "Reaction of Ketohexoses with Acids", J. appl. Chem., 1966, vol. 16, July, pp. 206-208.
Huber et al., "Production of Liquid Alkanes by Aqueous-Phase Processing of Biomass-Derived Carbohydrates" Science, vol. 308, 2005, pp. 1446-1450, XP002458811.

* cited by examiner

*Primary Examiner* — Nizal Chandrakumar
(74) *Attorney, Agent, or Firm* — Wells St. John P.S.

(57) ABSTRACT

A method of reducing hydroxymethylfurfural (HMF) where a starting material containing HMF in a solvent comprising water is provided. $H_2$ is provided into the reactor and the starting material is contacted with a catalyst containing at least one metal selected from Ni, Co, Cu, Pd, Pt, Ru, Ir, Re and Rh, at a temperature of less than or equal to 250° C. A method of hydrogenating HMF includes providing an aqueous solution containing HMF and fructose. $H_2$ and a hydrogenation catalyst are provided. The HMF is selectively hydrogenated relative to the fructose at a temperature at or above 30° C. A method of producing tetrahydrofuran dimethanol (THFDM) includes providing a continuous flow reactor having first and second catalysts and providing a feed comprising HMF into the reactor. The feed is contacted with the first catalyst to produce furan dimethanol (FDM) which is contacted with the second catalyst to produce THFDM.

14 Claims, 80 Drawing Sheets

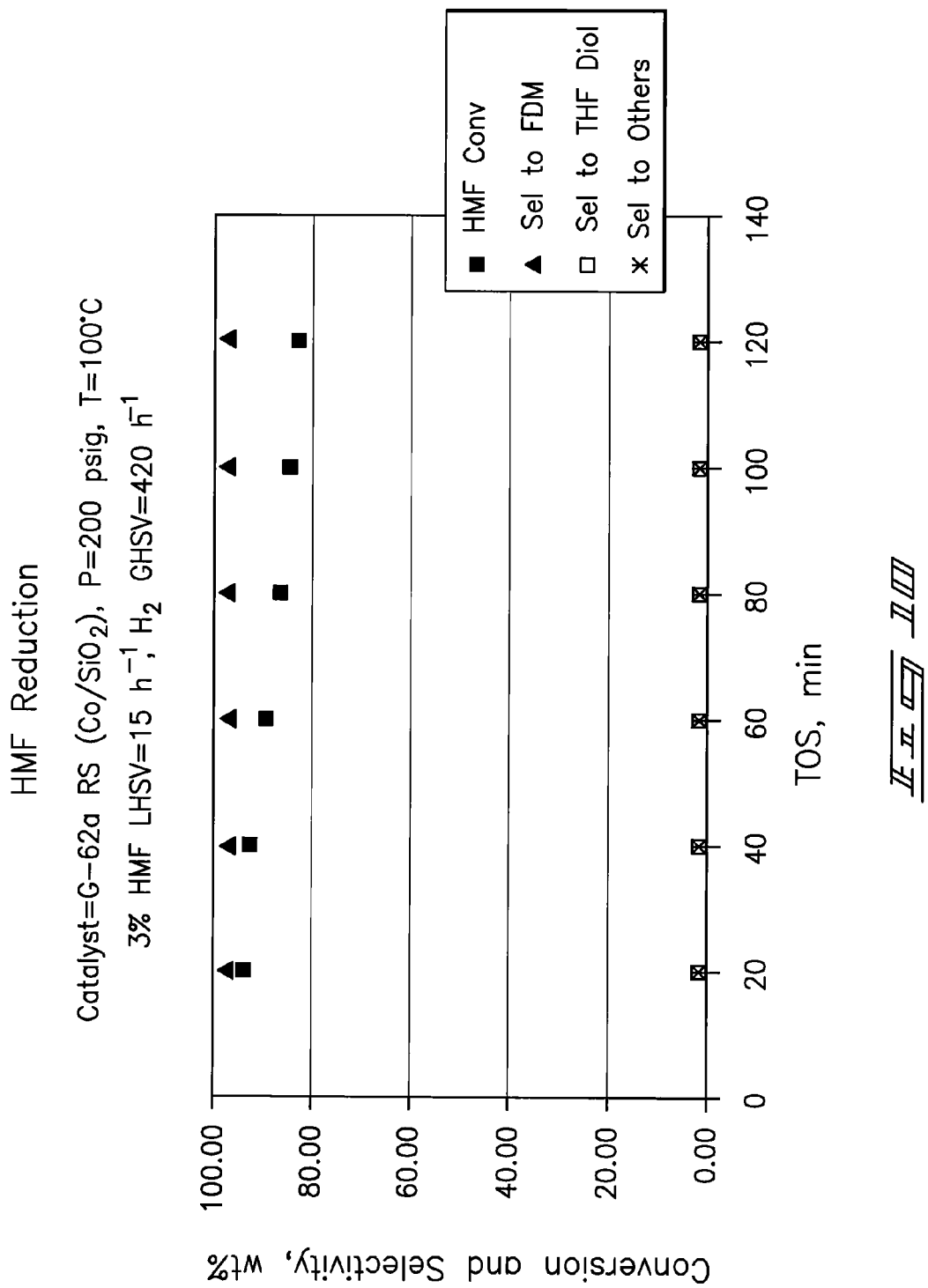

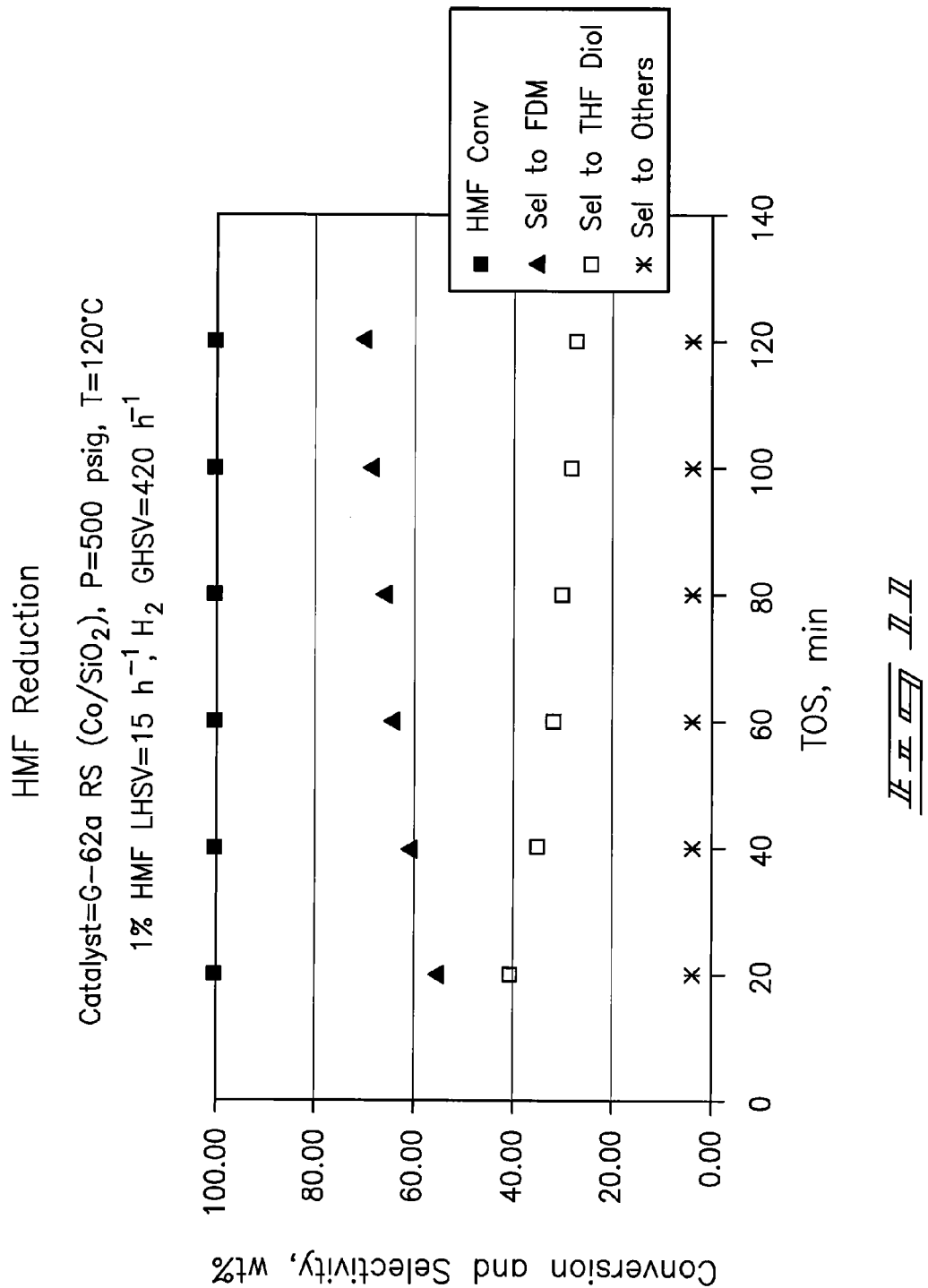

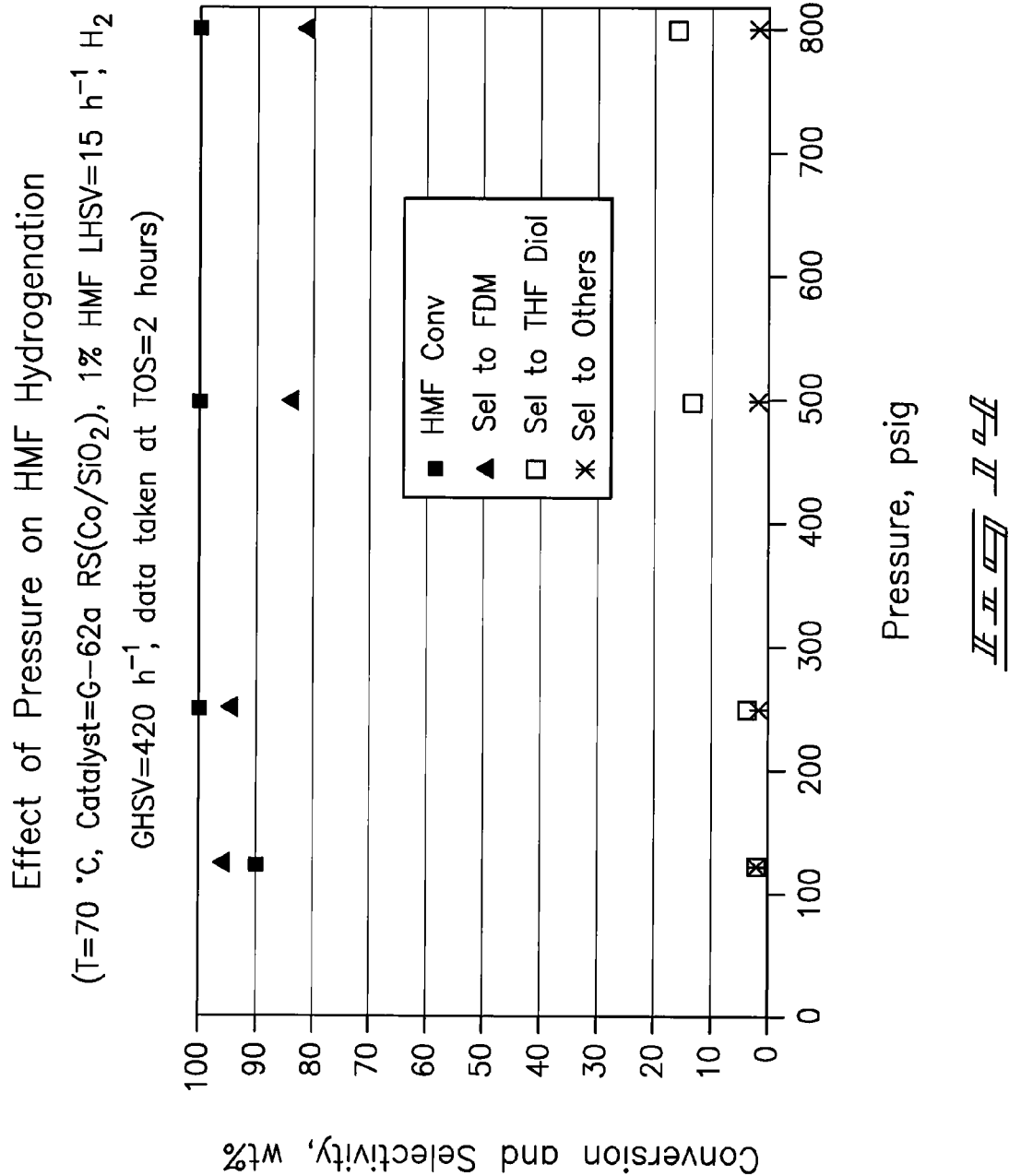

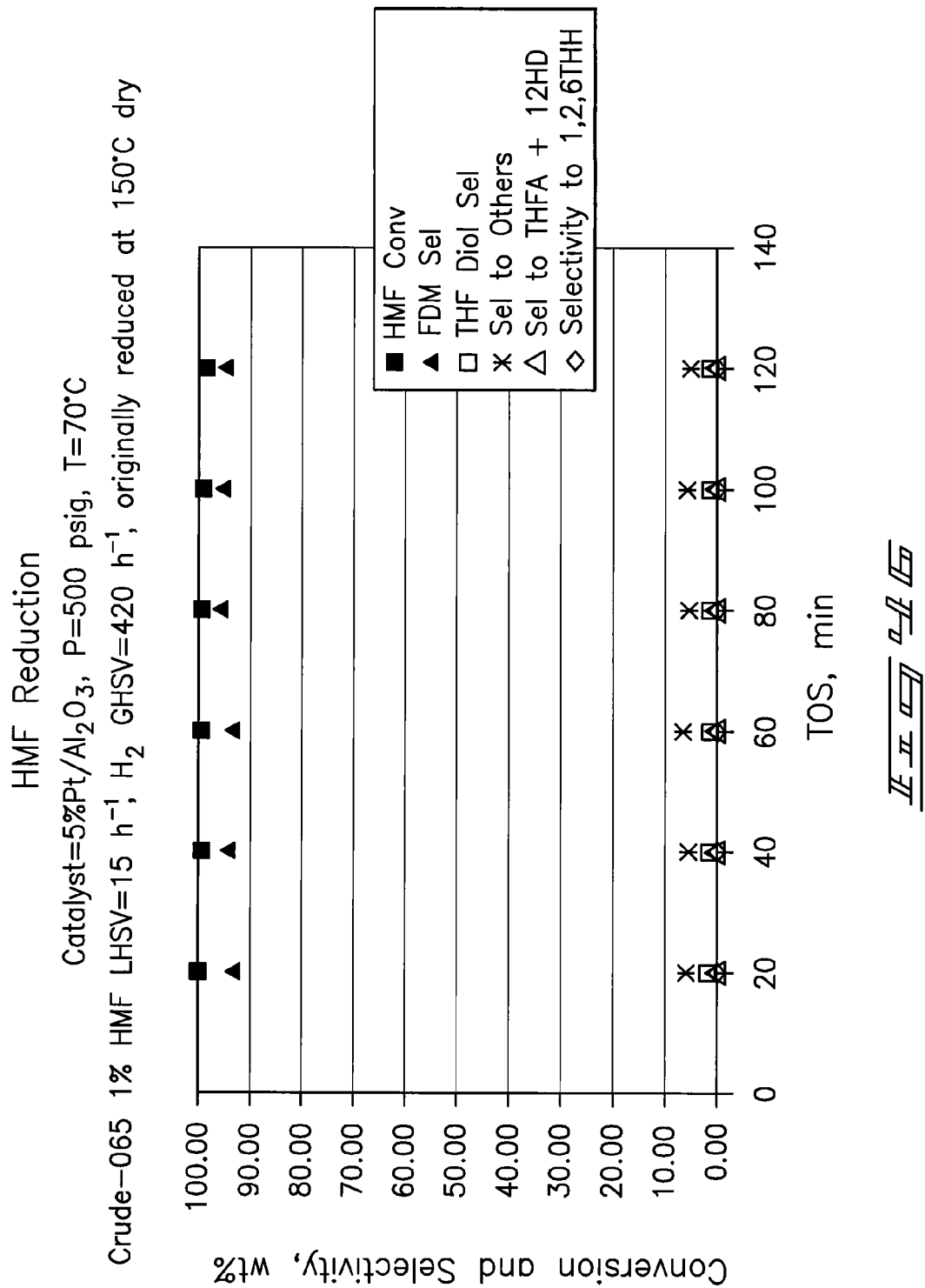

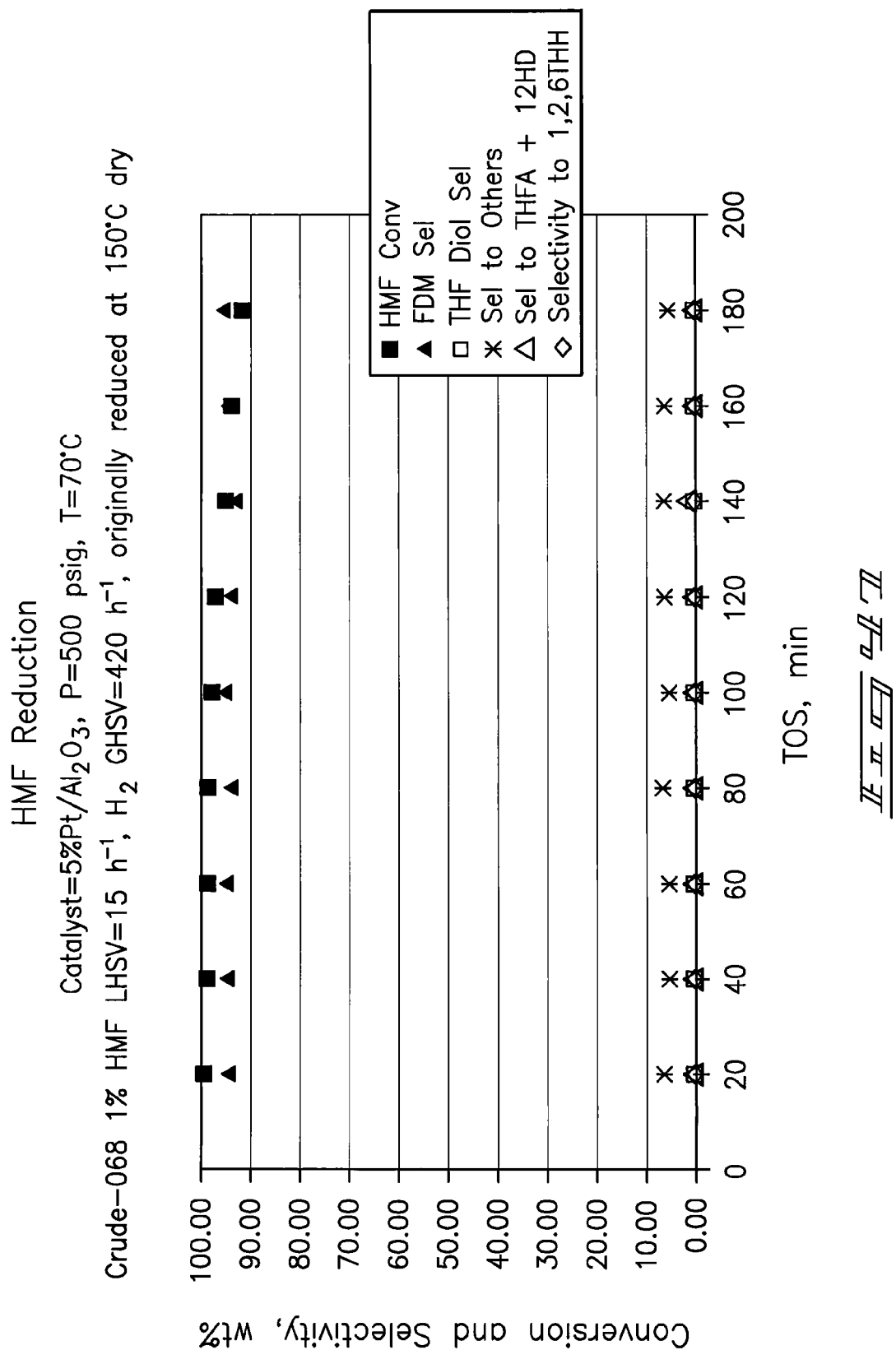

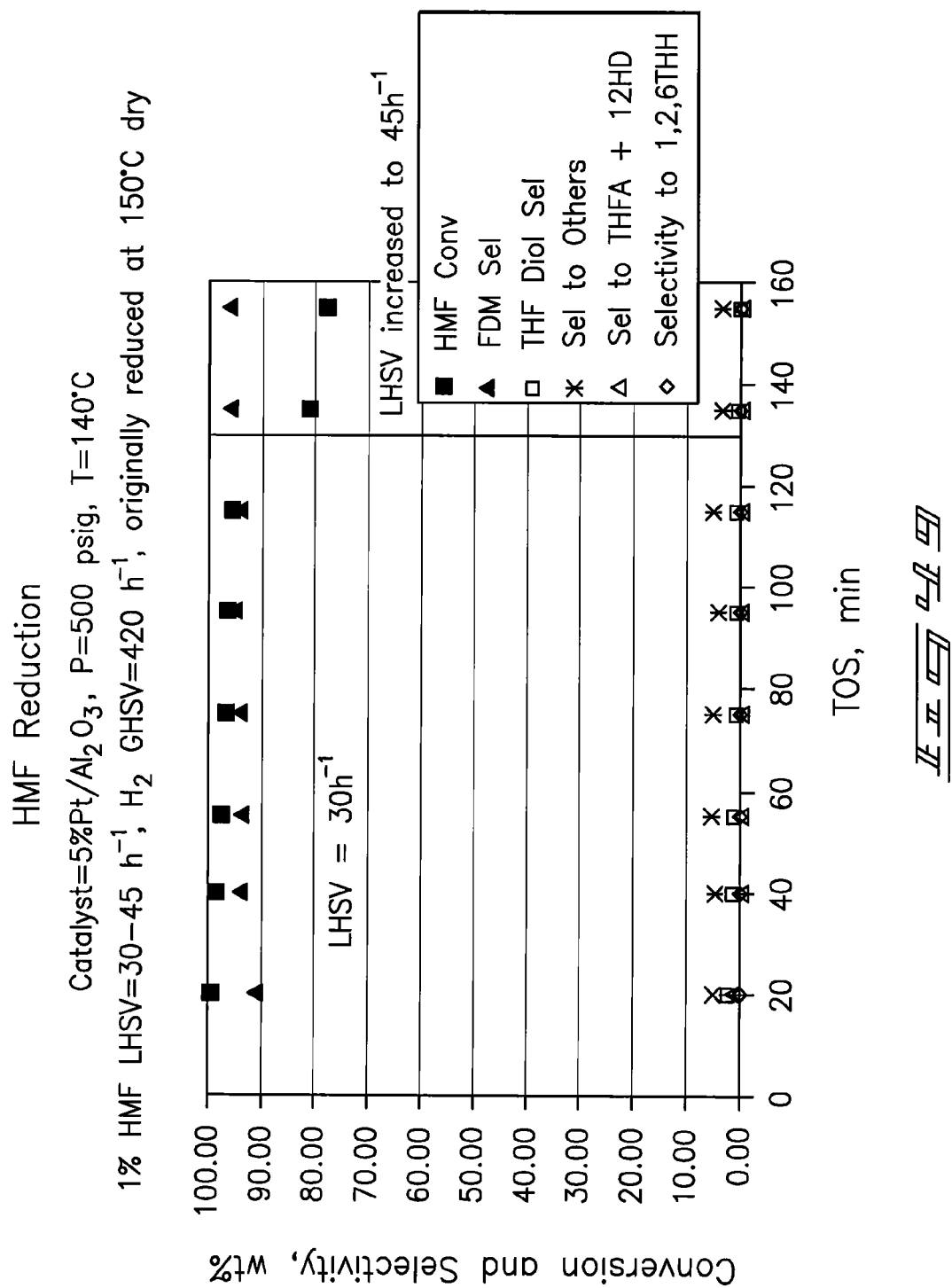

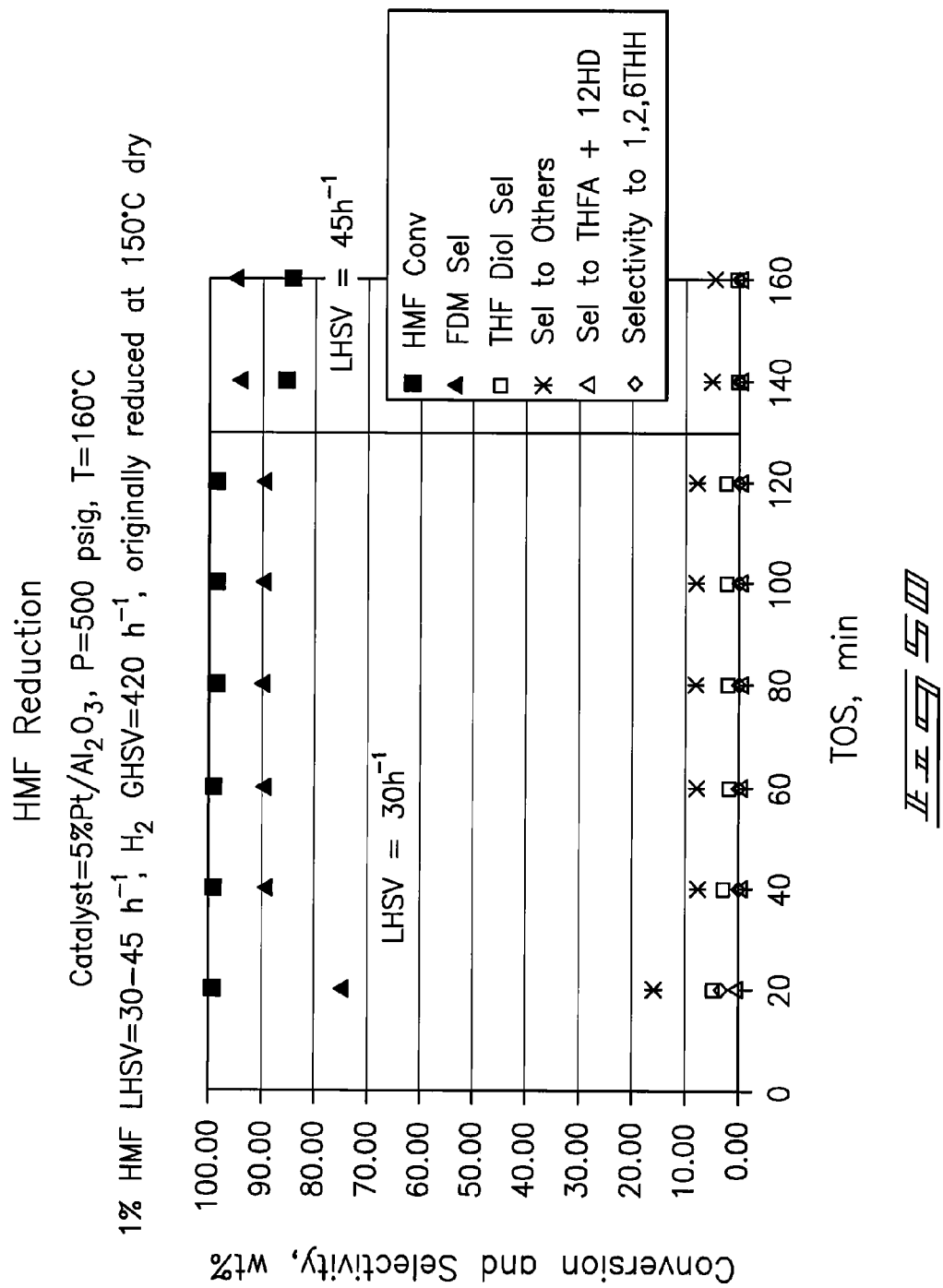

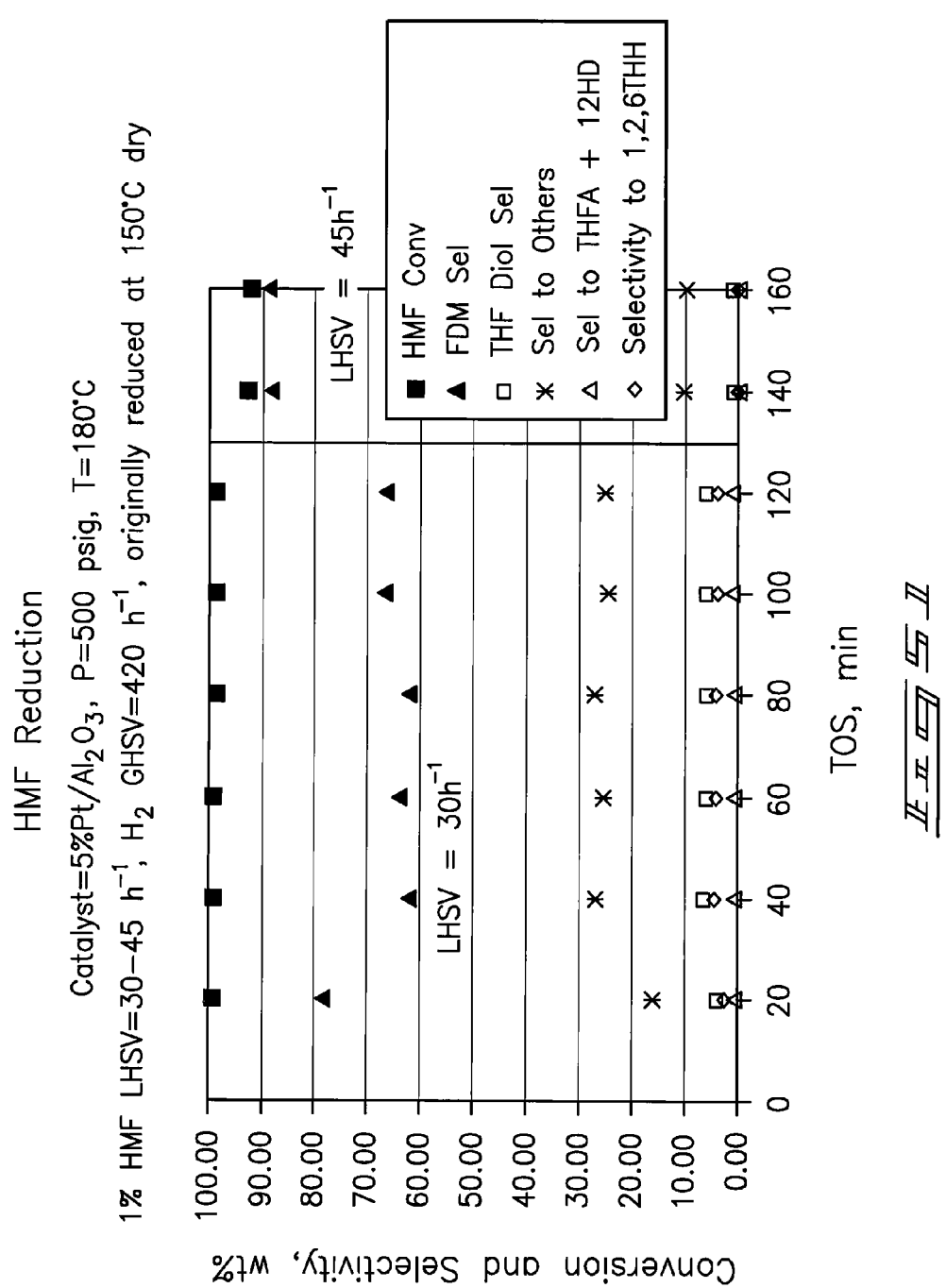

3% HMF, 500 psig H₂, 70°C

LHSV = 2.7–4.5 h⁻¹, GHSV = 127.3 h⁻¹

Legend:
- ◆ HMF Conv
- □ Sel to 14.25 (not FDM)
- △ Sel to FDM
- ○ Sel to 17.03
- ✱ Sel to 18.20
- ● Sel to THFDM
- ┼ Sel to 27.12

X-axis: Time (min)
Y-axis: Conversion and Selectivity, wt%

LHSV = 2.7 h⁻¹ | LHSV = 4.5 h⁻¹

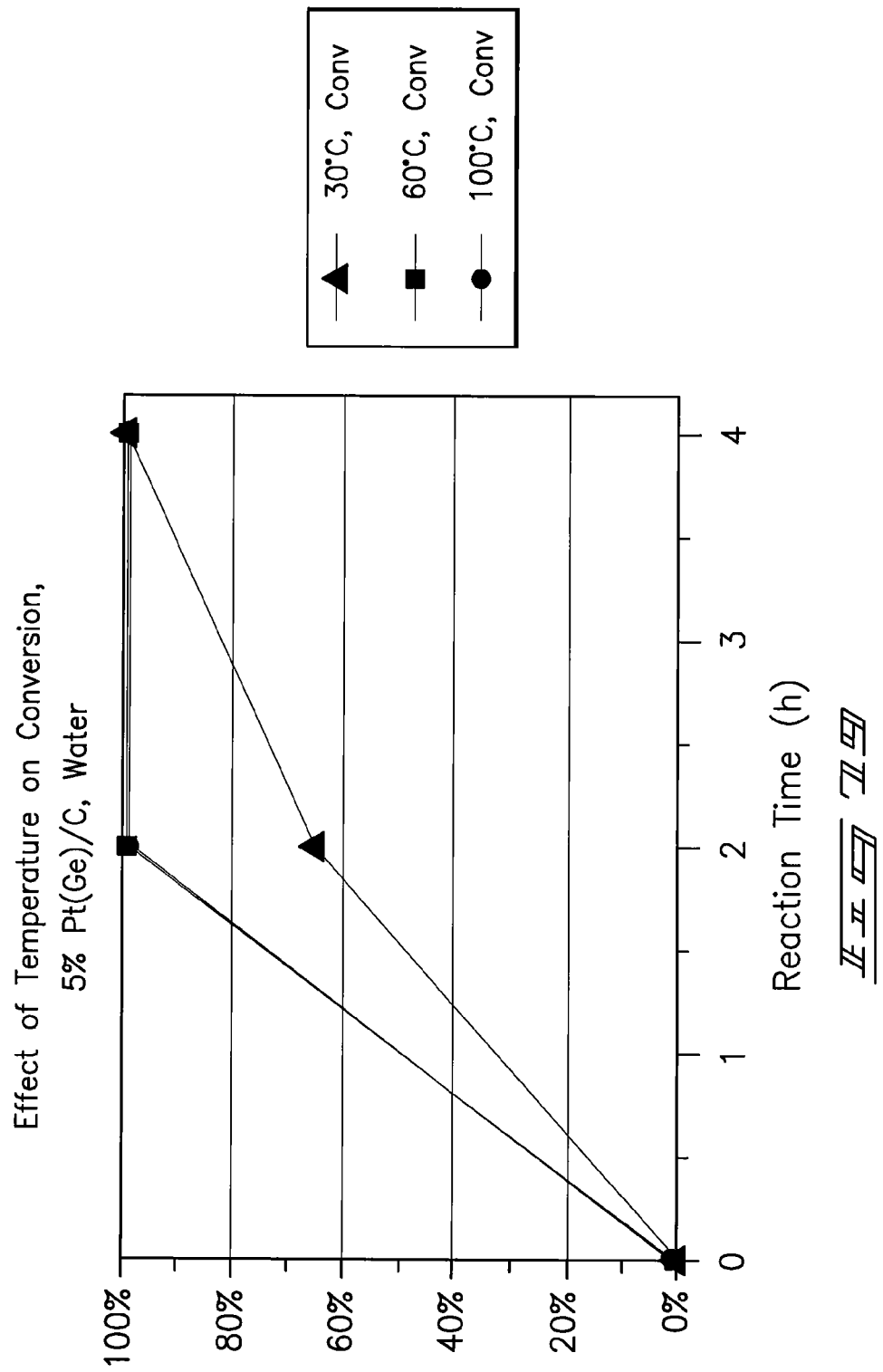

US 8,367,851 B2

HYDROXYMETHYLFURFURAL REDUCTION METHODS AND METHODS OF PRODUCING FURANDIMETHANOL

RELATED PATENT DATA

This patent is a continuation of U.S. patent application Ser. No. 11/760,634 entitled Hydroxymethylfurfural Reduction Methods and Methods of Producing Furandimethanol which was filed Jun. 8, 2007 now U.S. Pat. No. 7,994,347 and claims priority under 35 U.S.C. §119 to U.S. Provisional Application No. 60/804,409, which was filed Jun. 9, 2006, the entirety of both of which are incorporated by reference herein.

TECHNICAL FIELD

The invention pertains to hydroxymethylfurfural reduction methods, methods of producing furandimethanol, and methods of producing tetrahydrofuran dimethanol.

BACKGROUND OF THE INVENTION

Hydroxymethylfurfural (HMF) is a compound which can be produced from various hexoses or hexose-comprising materials. HMF can in turn be converted into a variety of derivatives, many of which are currently or are quickly becoming commercially valuable. Of particular interest is a reduction product furandimethanol (FDM). Another reduction product of interest is tetrahydrofuran dimethanol (THF dimethanol, alternatively referred to as THF-diol or THFDM). FDM and THF dimethanol are useful in adhesives, sealants, composites, coatings, binders, foams, curatives, polymer materials, solvents, resins or as monomers, for example.

Conventional methodology for production of FDM and/or THF dimethanol from HMF typically results in low yields, and/or low selectivity and can therefore be cost prohibitive. Additionally, conventional methodology often utilizes one or more environmentally unfriendly compound or solvent, or utilizes harsh reaction conditions. Accordingly, it is desirable to develop alternative methods for production of FDM and/or THF dimethanol from HMF.

SUMMARY OF THE INVENTION

In one aspect the invention encompasses a method of reducing HMF where a starting material containing HMF in a solvent comprising water is provided into a reactor. $H_2$ is provided into a reactor and the starting material is contacted with a catalyst containing at least one metal selected from Ni, Co, Cu, Pd, Pt, Ru, Ir, Re and Rh. The contacting is conducted at a reactor temperature of less than or equal to 250° C.

In one aspect the invention encompasses a method of hydrogenating HMF. An aqueous solution containing HMF and fructose is provided into a reactor and $H_2$ is provided into the reactor. A hydrogenation catalyst is provided in the reactor. The HMF is selectively hydrogenated relative to the fructose at a temperature at or above about 30° C.

In one aspect the invention pertains to a method of producing tetrahydrofuran dimethanol (THFDM) A feed comprising HMF is provided into a reactor containing a first and a second catalyst. The feed is contacted with the first catalyst to produce furan dimethanol (FDM). The FDM is contacted with the second catalyst to produce THFDM.

BRIEF DESCRIPTION OF THE DRAWINGS

Preferred embodiments of the invention are described below with reference to the following accompanying drawings.

FIG. 10 shows HMF conversion and product selectivity as a function of time on stream utilizing the catalyst of FIG. 1 at an increased HMF feed concentration and a decreased pressure with increased temperature relative to that of FIG. 1.

FIG. 13 shows HMF conversion and product selectivity as a function of temperature utilizing the catalyst of FIG. 1.

FIG. 14 shows HMF conversion and product selectivity as a function of pressure utilizing the catalyst of FIG. 1.

FIG. 46 shows HMF conversion and product selectivity as a function of time on stream utilizing the catalyst of FIG. 43 and a second crude HMF feed.

FIG. 47 shows HMF conversion and product selectivity as a function of time on stream utilizing the catalyst of FIG. 43 and a third crude HMF feed.

FIG. 49 shows HMF conversion and product selectivity as a function of time on stream for the catalyst of FIG. 43 at an increased reactor temperature and at an increased LHSV relative to FIG. 43.

FIG. 50 shows HMF conversion and product selectivity as a function of time on stream of the catalyst of FIG. 43 at an increased reactor temperature and increased LHSV relative to FIG. 43.

FIG. 51 shows HMF conversion and product selectivity as a function of time on stream for the catalyst of FIG. 43 at an increased reactor temperature and at an increased LHSV relative to FIG. 43.

FIG. 61 shows HMF conversion and product selectivity for a staged bed (segregated catalysts) continuous flow reactor utilizing Co/SiO$_2$ and Ni/SiO$_2$ catalysts.

FIG. 79 shows HMF conversion as a function of reaction time at three different temperatures utilizing a 5% Pt (Ge)/C catalyst.

Figure 1:
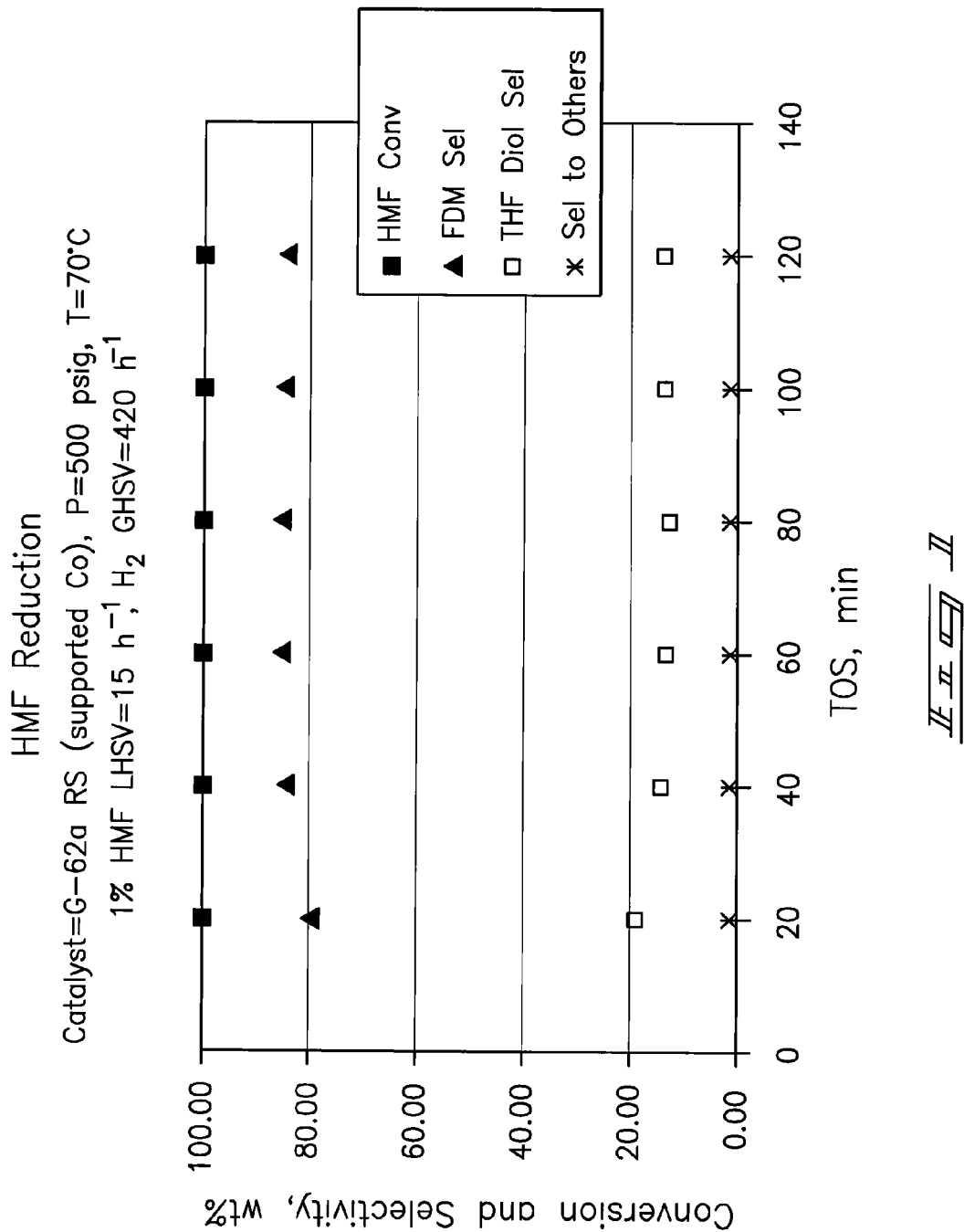
FIG. 1 shows conversion of HMF and selective production of furandimethanol and tetrahydrofuran diol (THF diol) as a function of time on stream (TOS) utilizing a continuous flow reactor with a cobalt supported on $SiO_2$ catalyst and a base set of parameters in accordance with one aspect of the invention.
Figure 2:
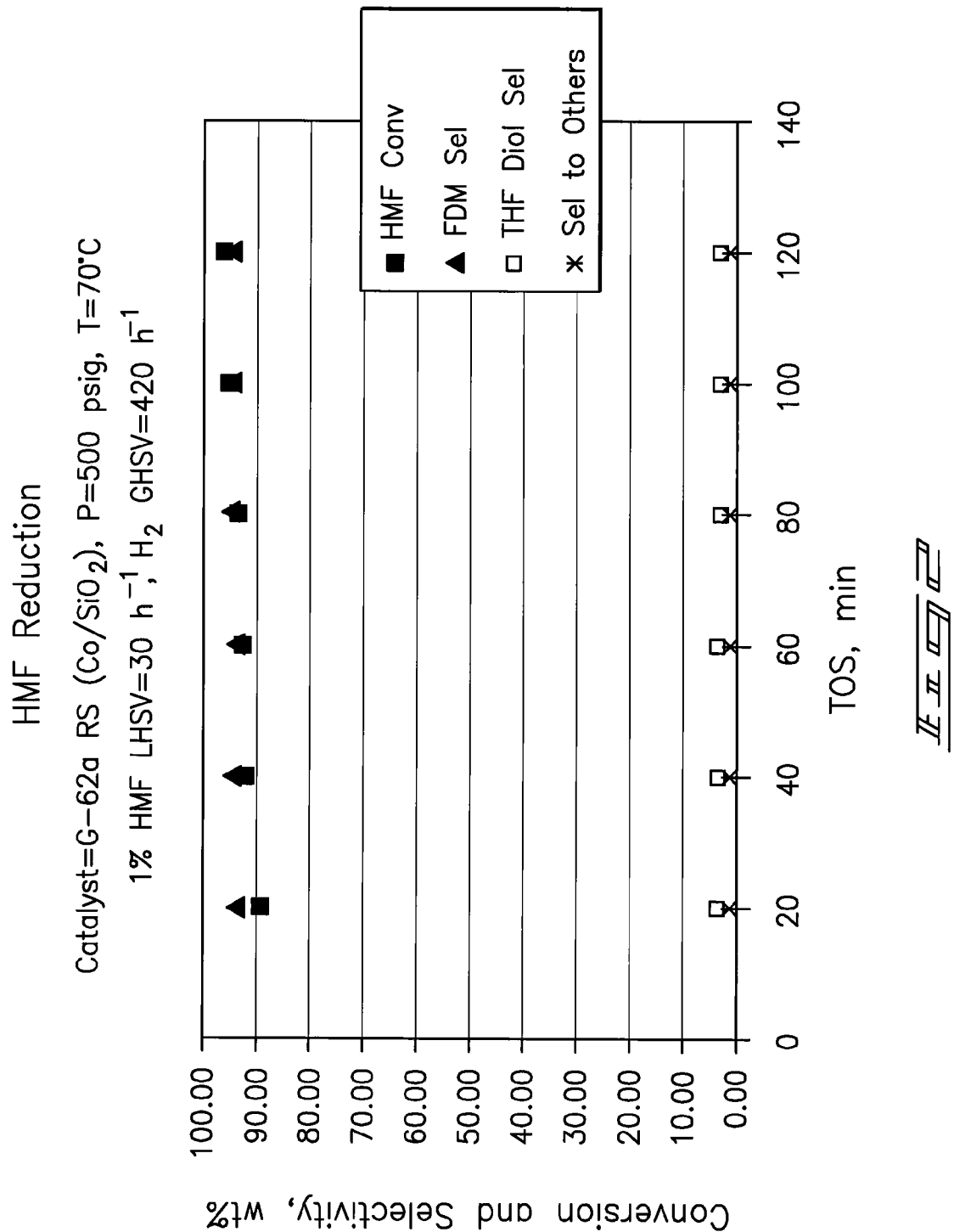
FIG. 2 shows HMF conversion and product selectivity as a function of time on stream utilizing the catalyst of FIG. 1 at an increased liquid hourly space velocity (LHSV) relative to FIG. 1.
Figure 3:
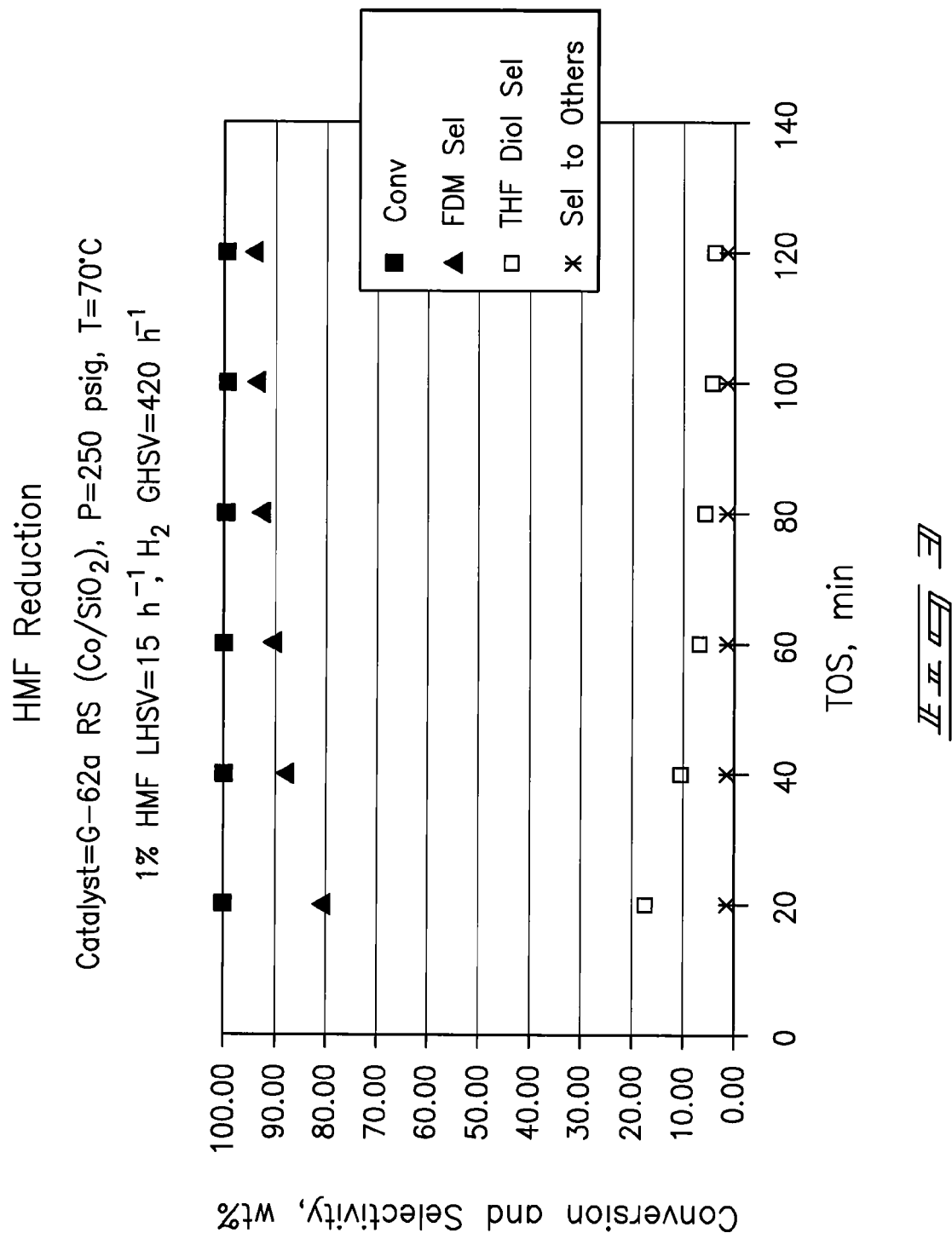
FIG. 3 shows HMF conversion and product selectivity as a function of time on stream utilizing the catalyst of FIG. 1 at a decreased pressure relative to FIG. 1.
Figure 4:
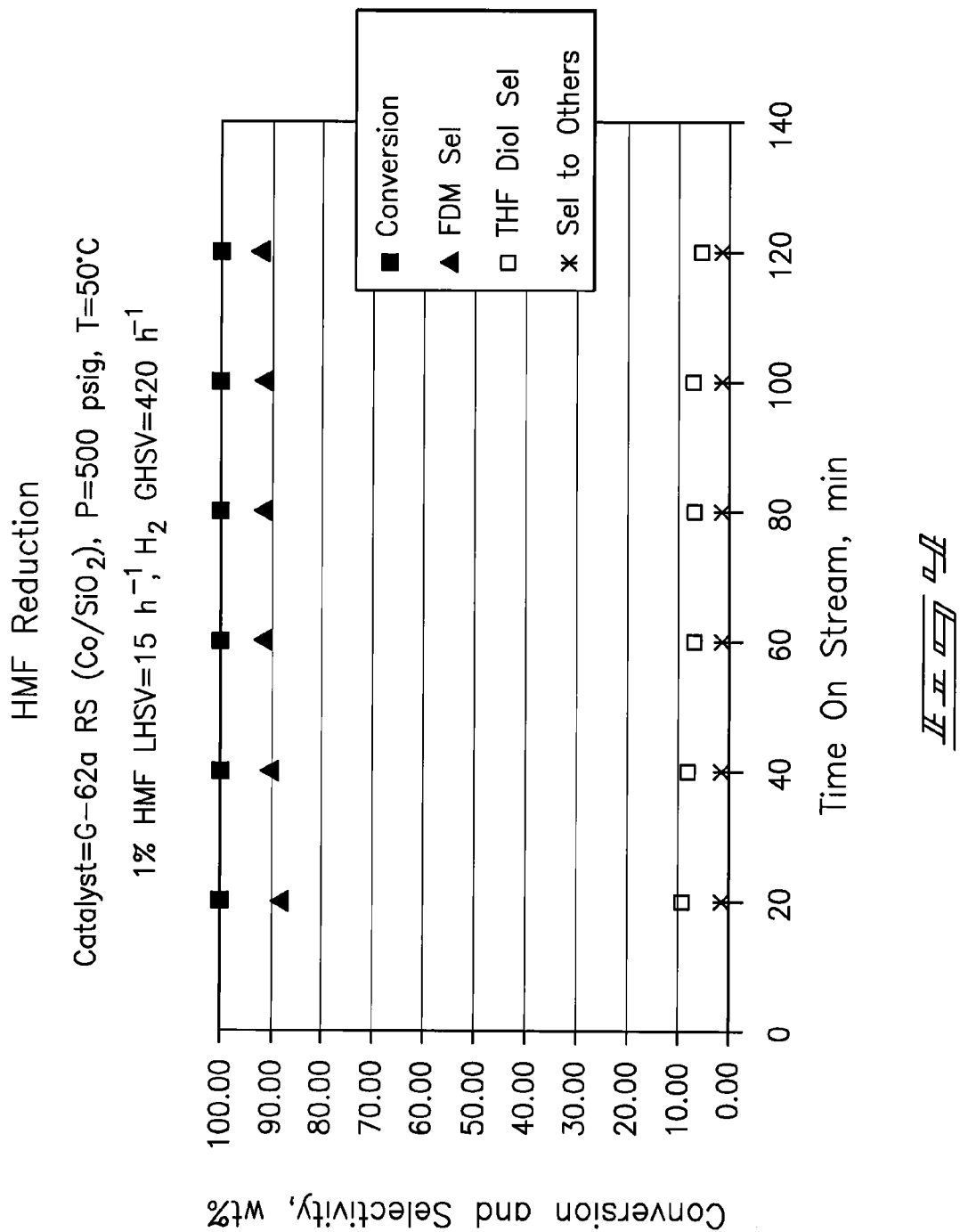
FIG. 4 shows HMF conversion and product selectivity as a function of time on stream utilizing the catalyst of FIG. 1 at a decreased temperature relative to FIG. 1.
Figure 5:
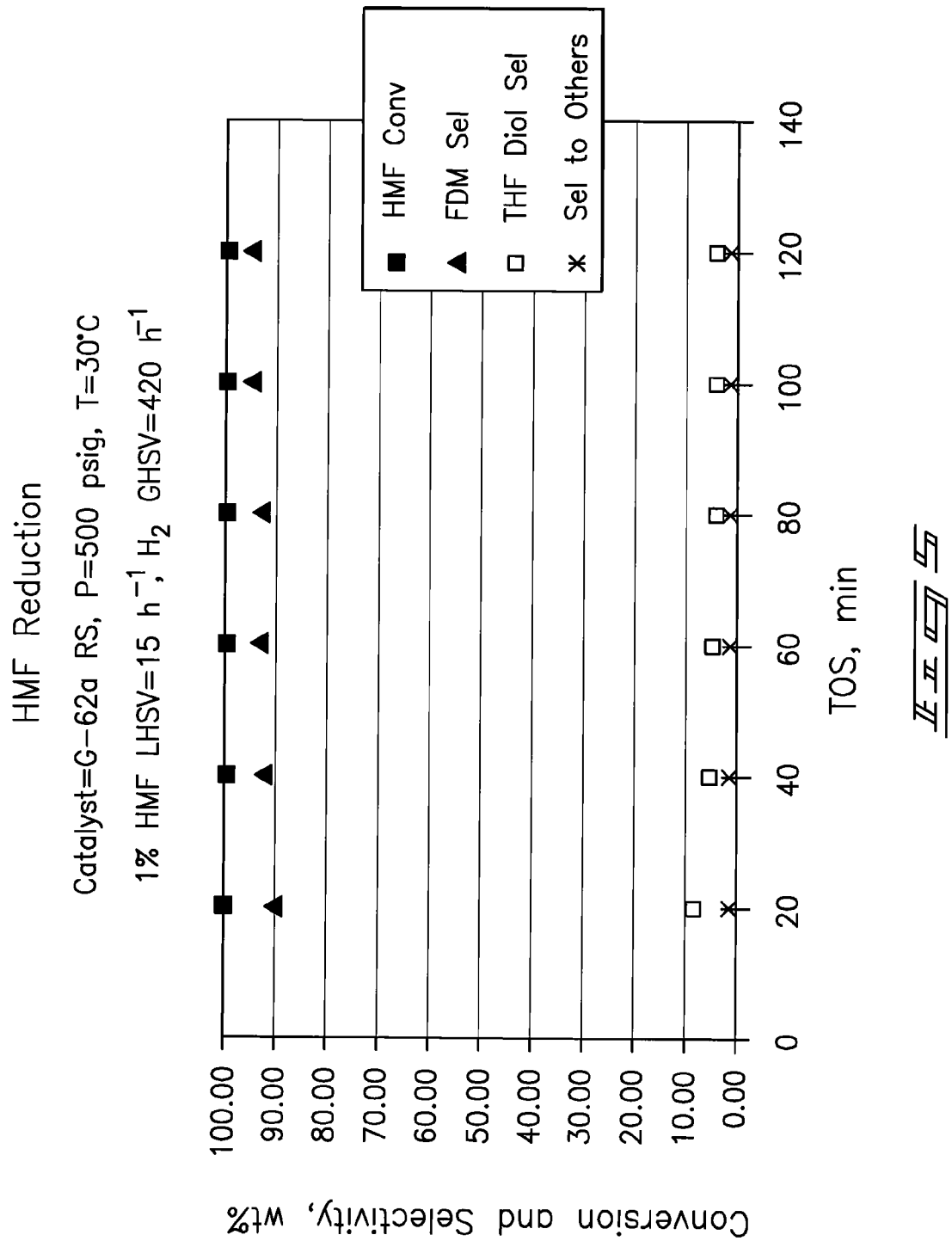
FIG. 5 shows HMF conversion and product selectivity as a function of time on stream utilizing the catalyst of FIG. 1 at a decreased temperature relative to FIG. 1.
Figure 6:
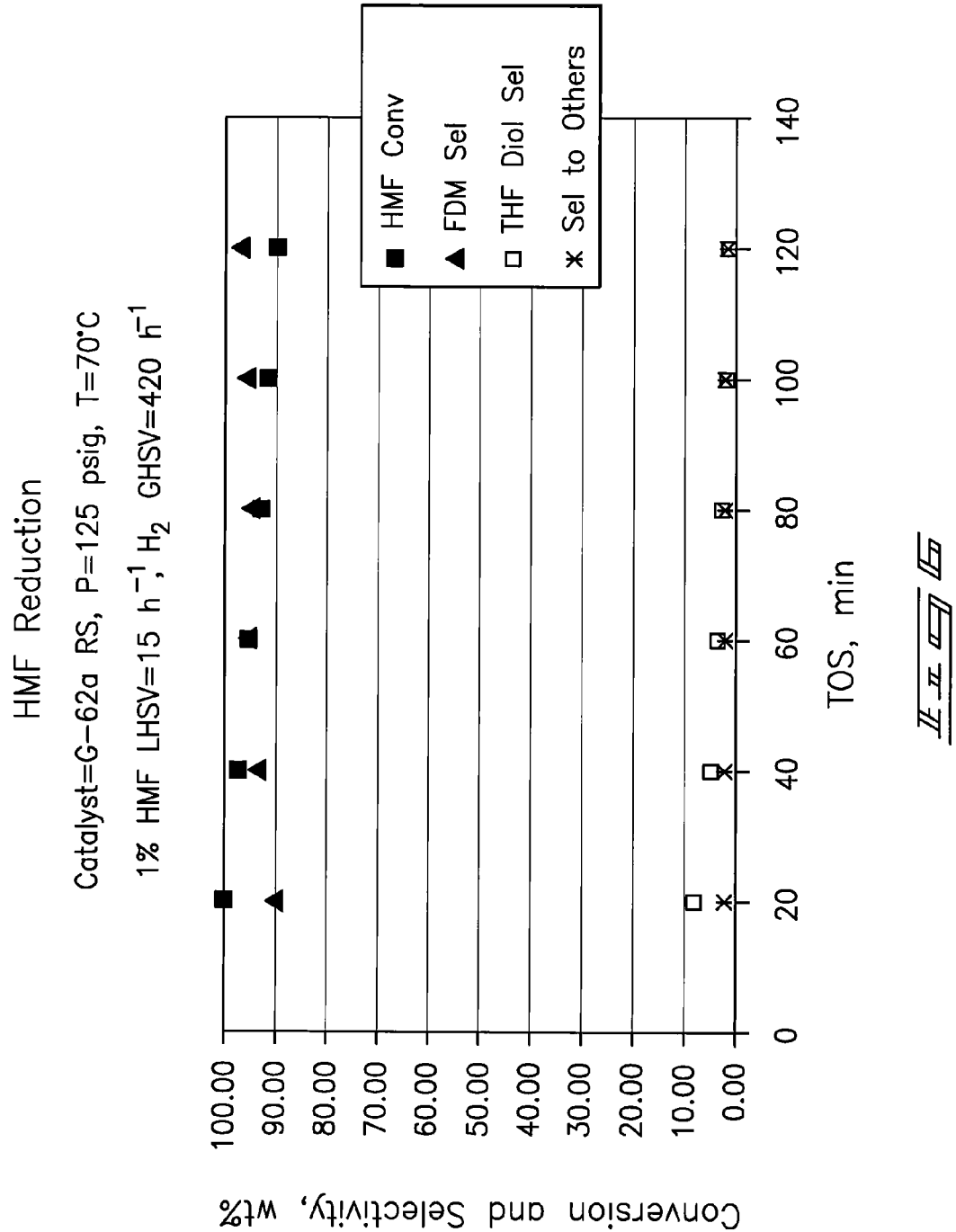
FIG. 6 shows HMF conversion and product selectivity as a function of time on stream utilizing the catalyst of FIG. 1 at a decreased pressure relative to that of FIG. 1.
Figure 7:
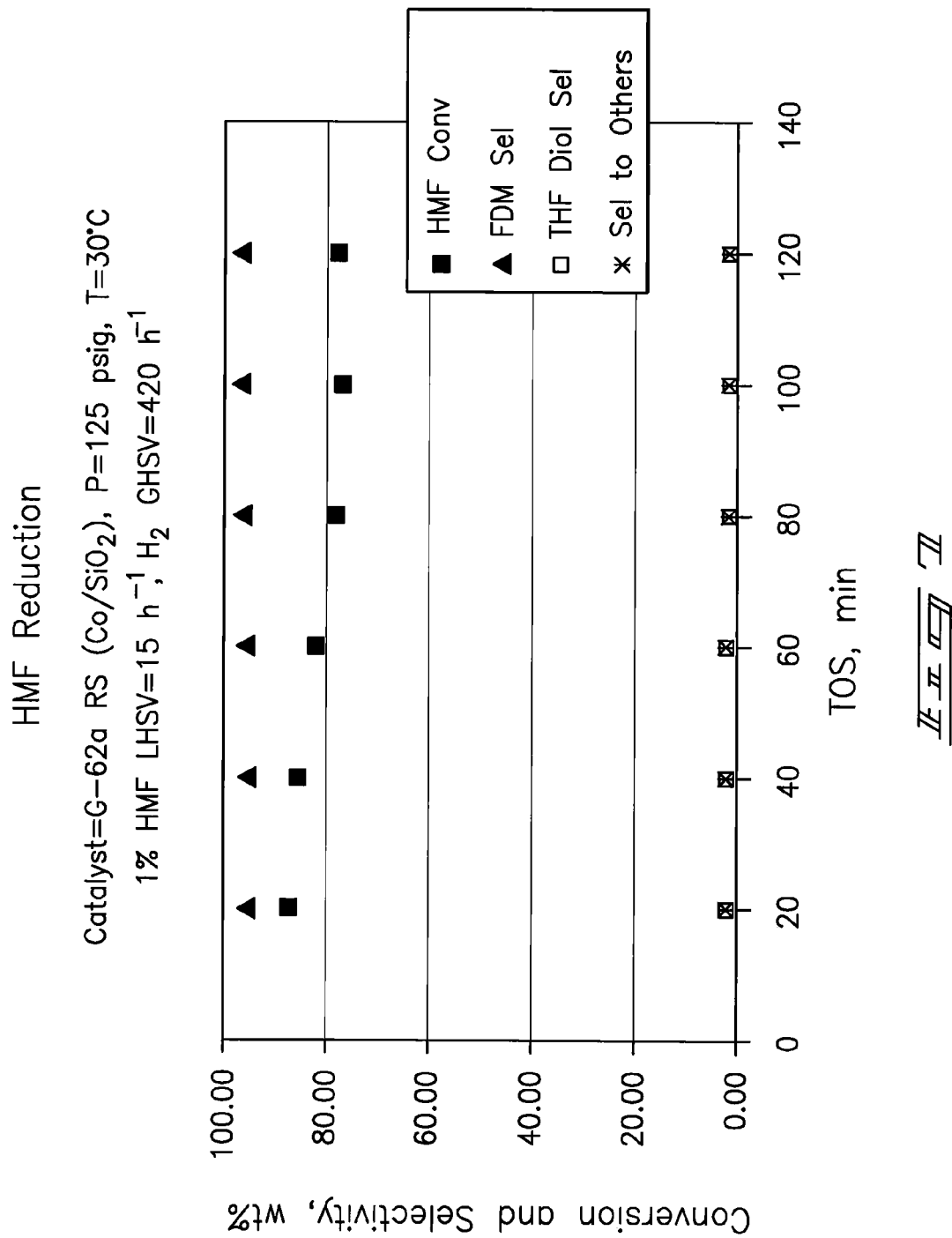
FIG. 7 shows HMF conversion and product selectivity as a function of time on stream utilizing the catalyst of FIG. 1 at decreased pressure and temperature relative to that of FIG. 1.
Figure 8:
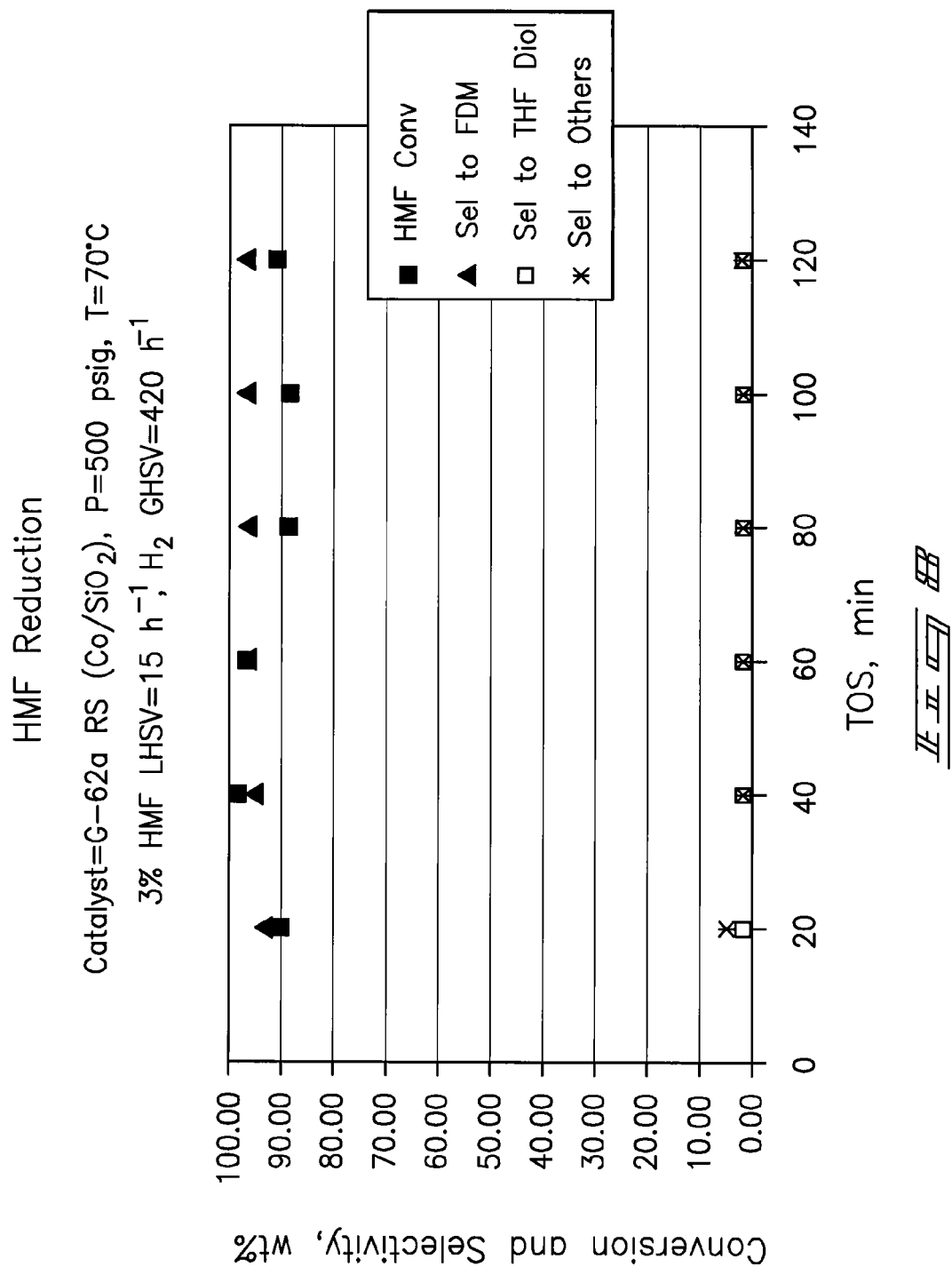
FIG. 8 shows HMF conversion and product selectivity as a function of time on stream utilizing the catalyst of FIG. 1 and an increased HMF feed concentration relative to that of FIG. 1.
Figure 9:
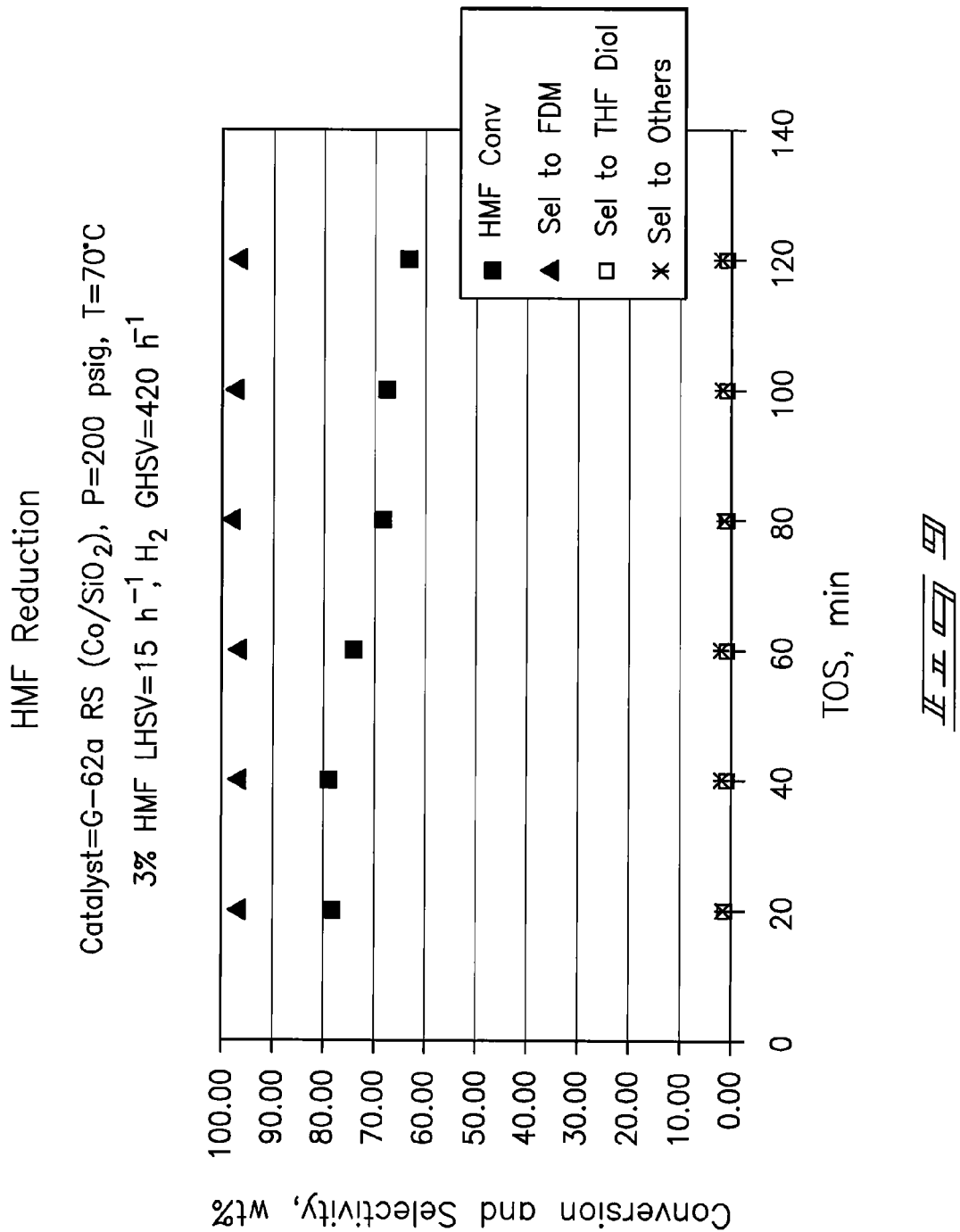
FIG. 9 shows HMF conversion and product selectivity as a function of time on stream utilizing the catalyst of FIG. 1 at an increased HMF feed concentration and decreased pressure relative to that of FIG. 1.
Figure 12:
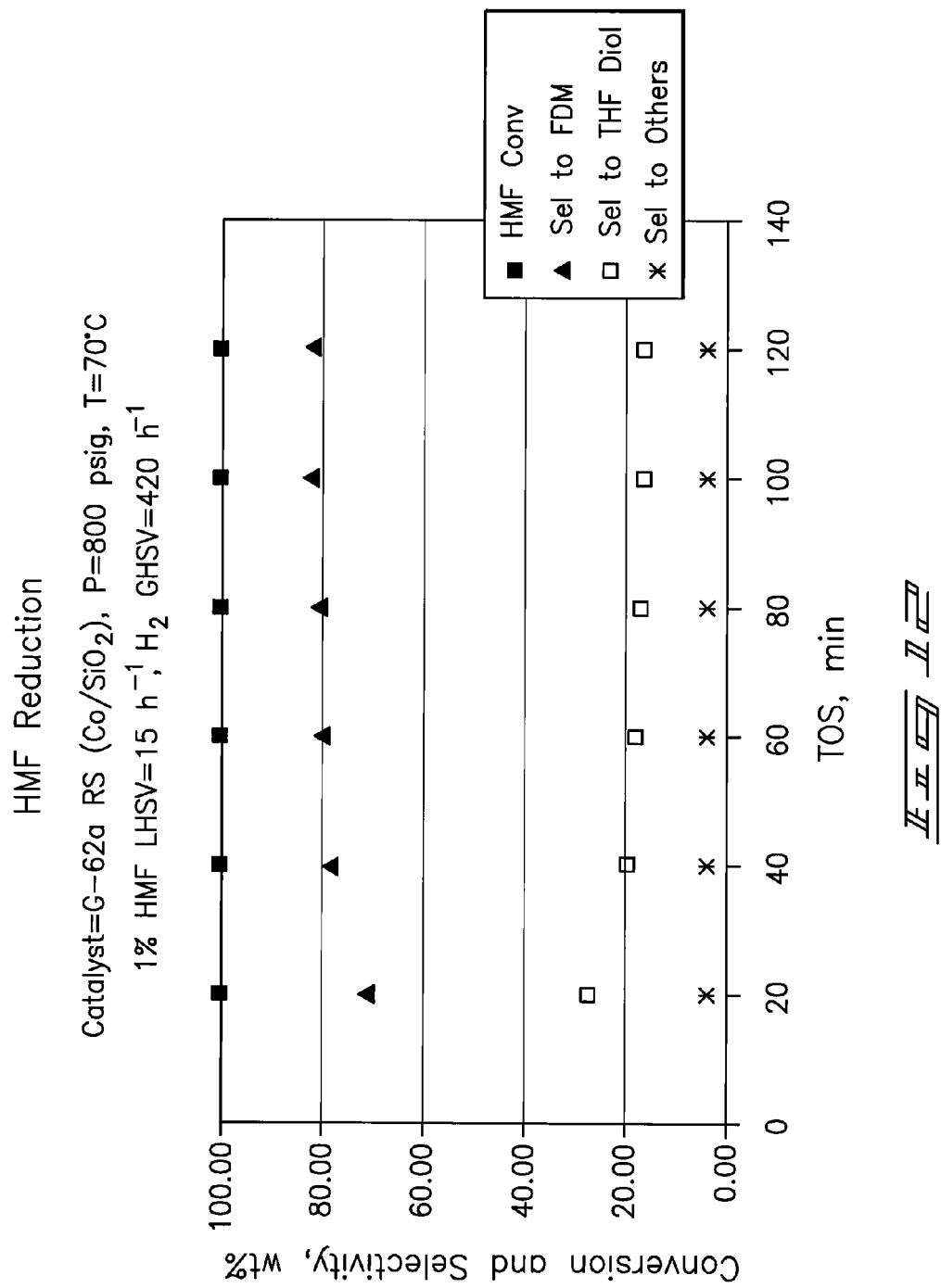
FIG. 12 shows HMF conversion and product selectivity as a function of time on stream utilizing the catalyst of FIG. 1 at an increased pressure relative to that of FIG. 1.
Figure 11:
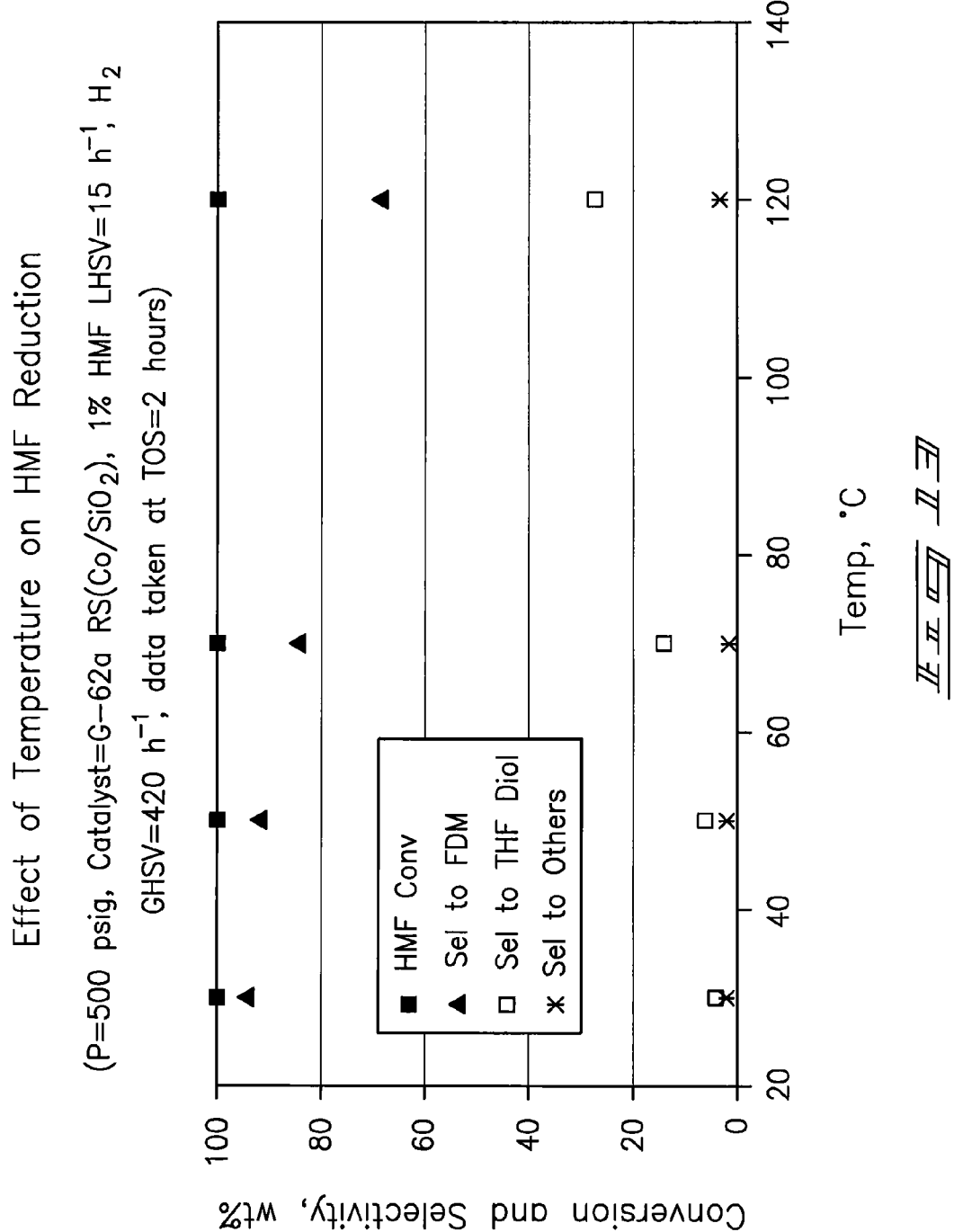
FIG. 11 shows HMF conversion and product selectivity as a function of time on stream utilizing the catalyst of FIG. 1 at an increased temperature relative to FIG. 1.
Figure 15:
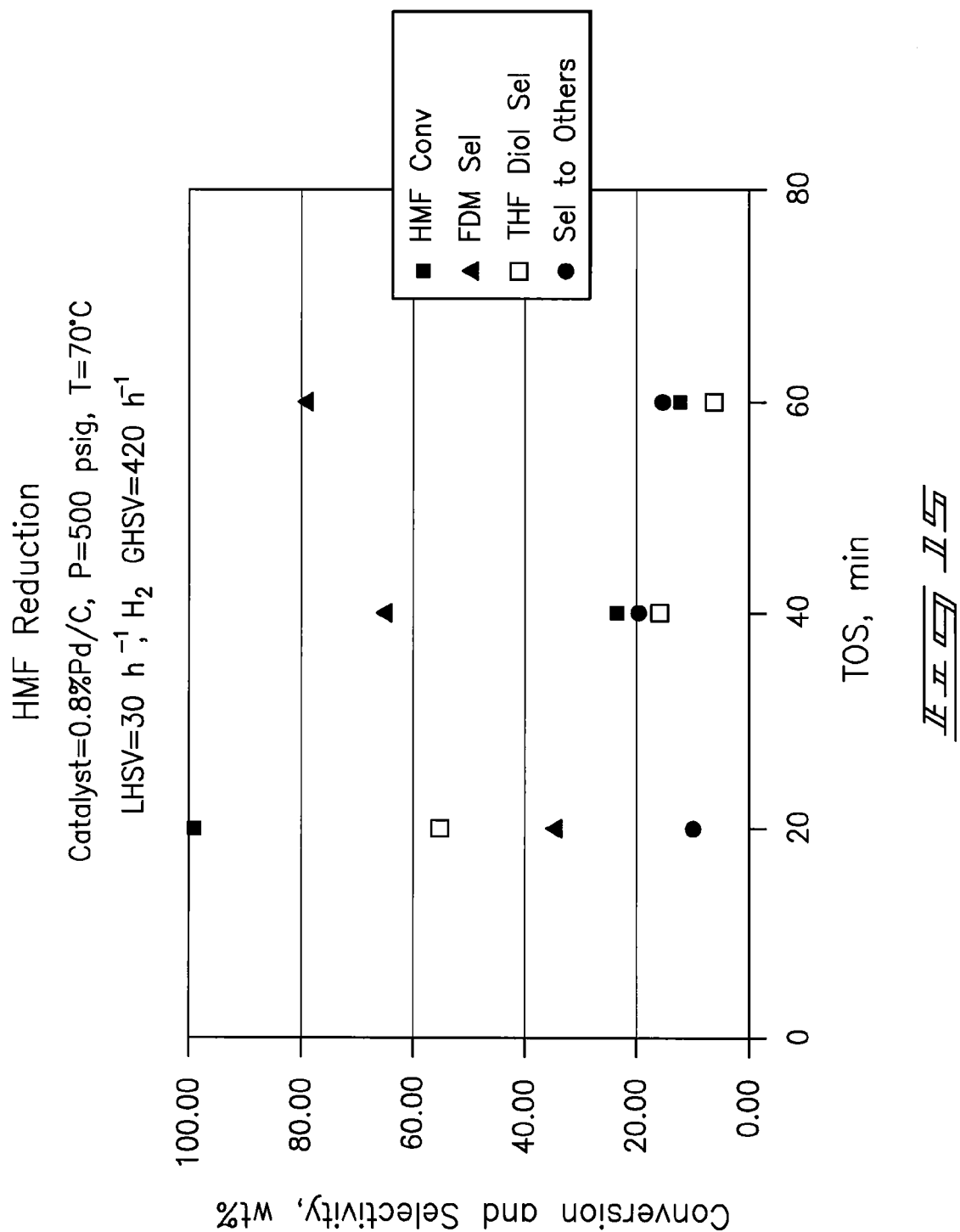
FIG. 15 shows HMF conversion and product selectivity as a function of time on stream utilizing an 0.8% palladium supported on carbon catalyst in a continuous flow reactor utilizing a base set of reaction parameters in accordance with one aspect of the invention.
Figure 16:
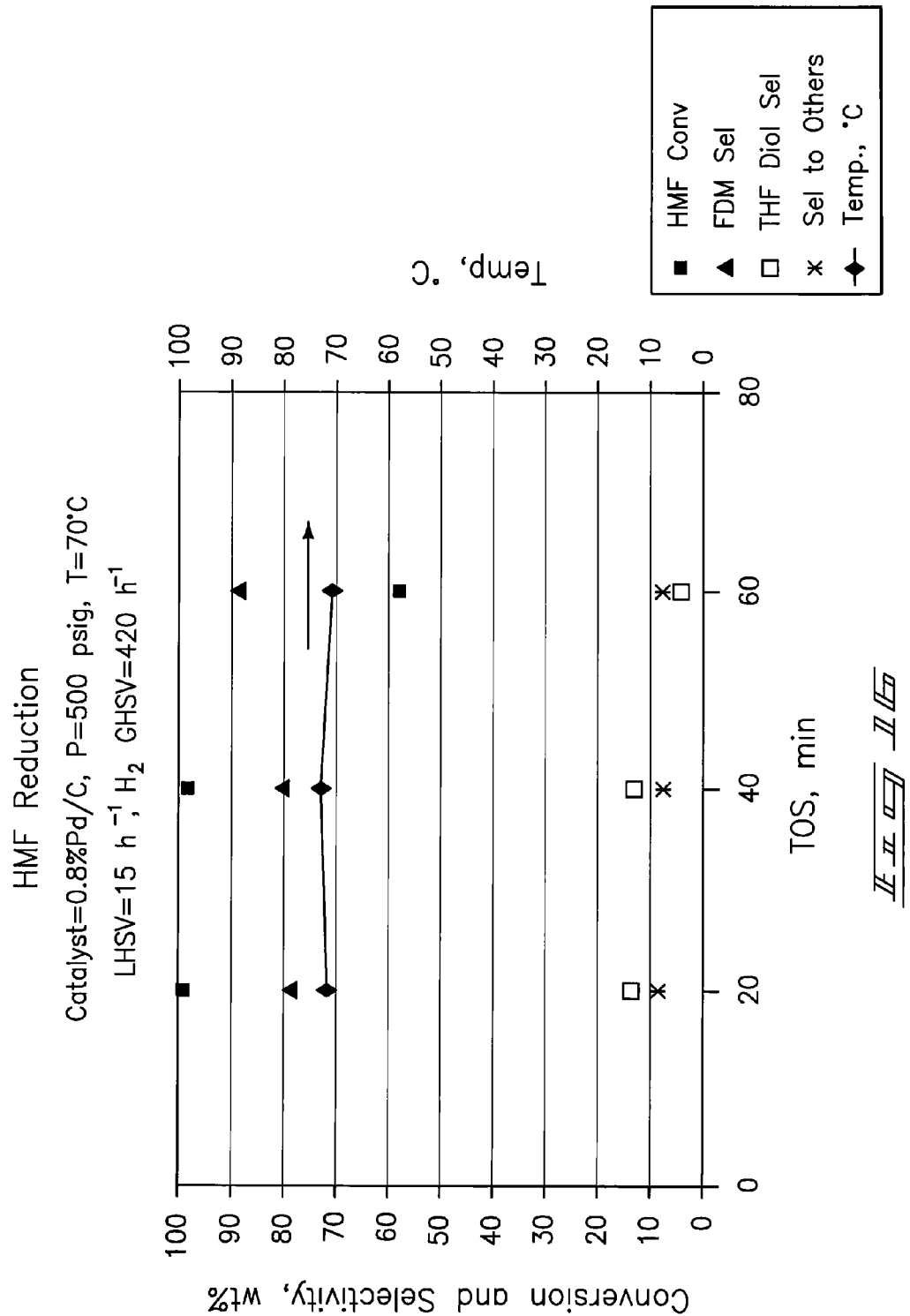
FIG. 16 shows HMF conversion and product selectivity as a function of time on stream utilizing the catalyst of FIG. 15 at a decreased LHSV relative to FIG. 15.
Figure 17:
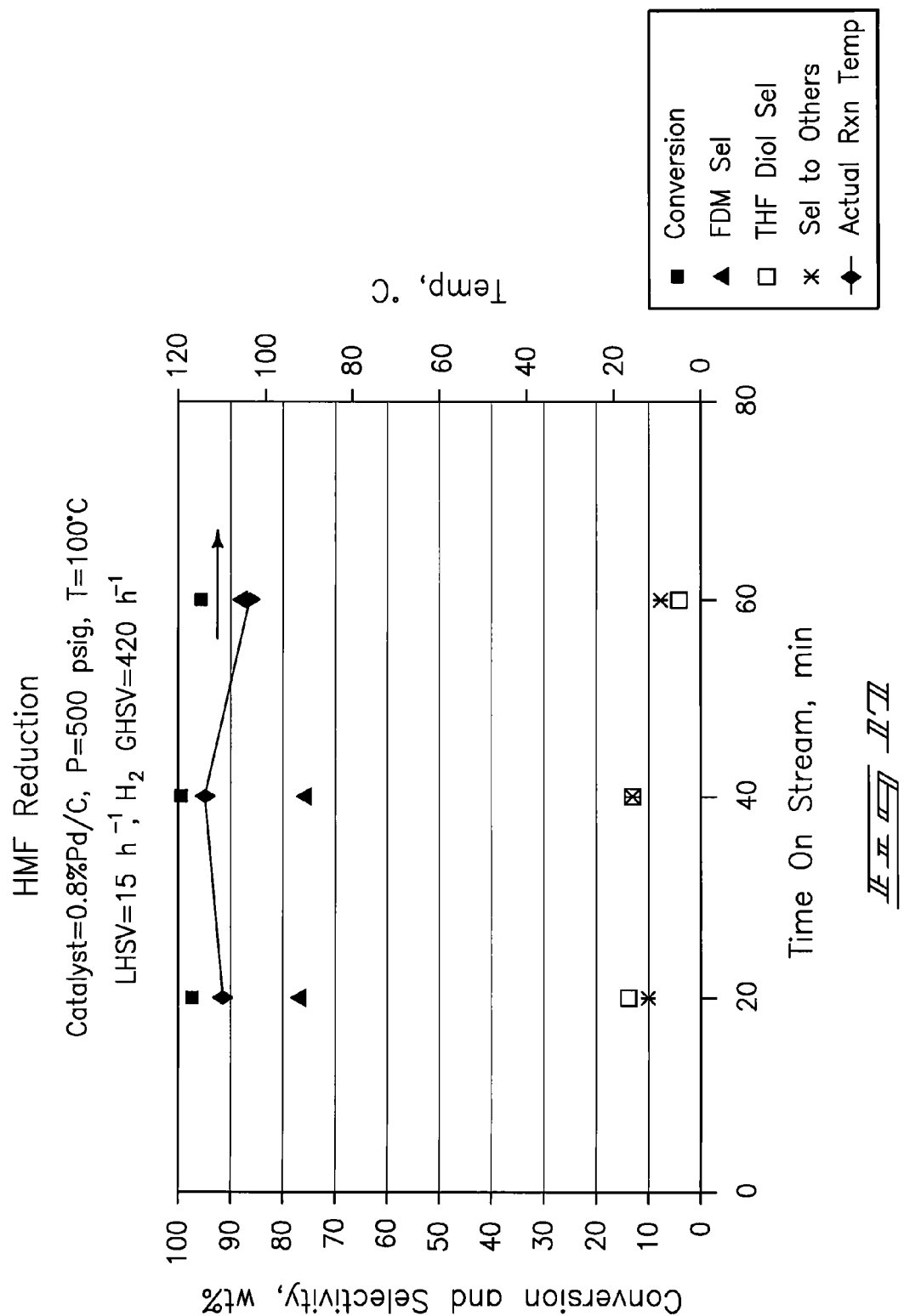
FIG. 17 shows HMF conversion and product selectivity as a function of time on stream utilizing the catalyst of FIG. 15 at an increased temperature and decreased LHSV relative to FIG. 15.
Figure 18:
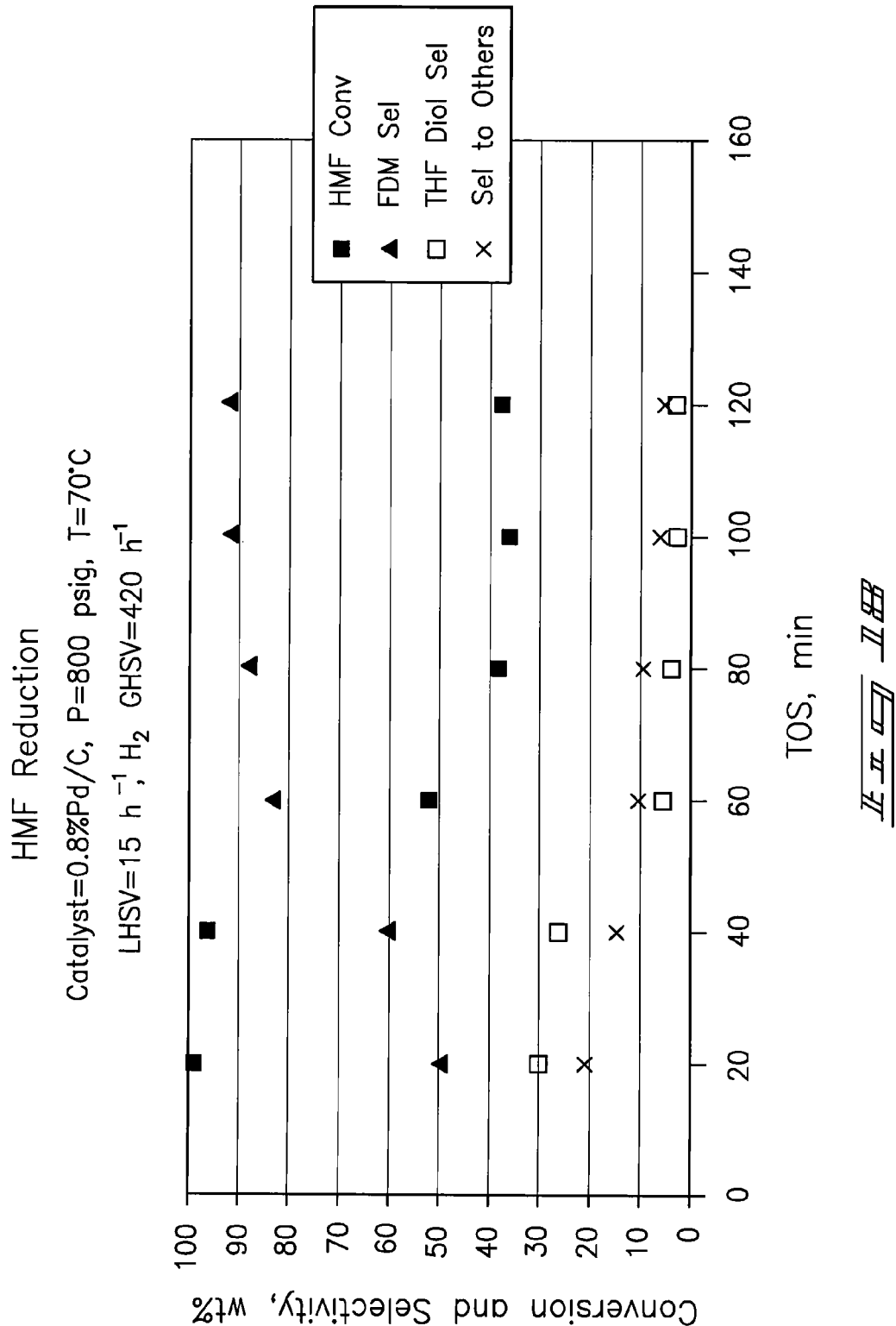
FIG. 18 shows HMF conversion and product selectivity as a function of time on stream utilizing the catalyst of FIG. 15 at an increased pressure and decreased LHSV relative to FIG. 15.
Figure 19:
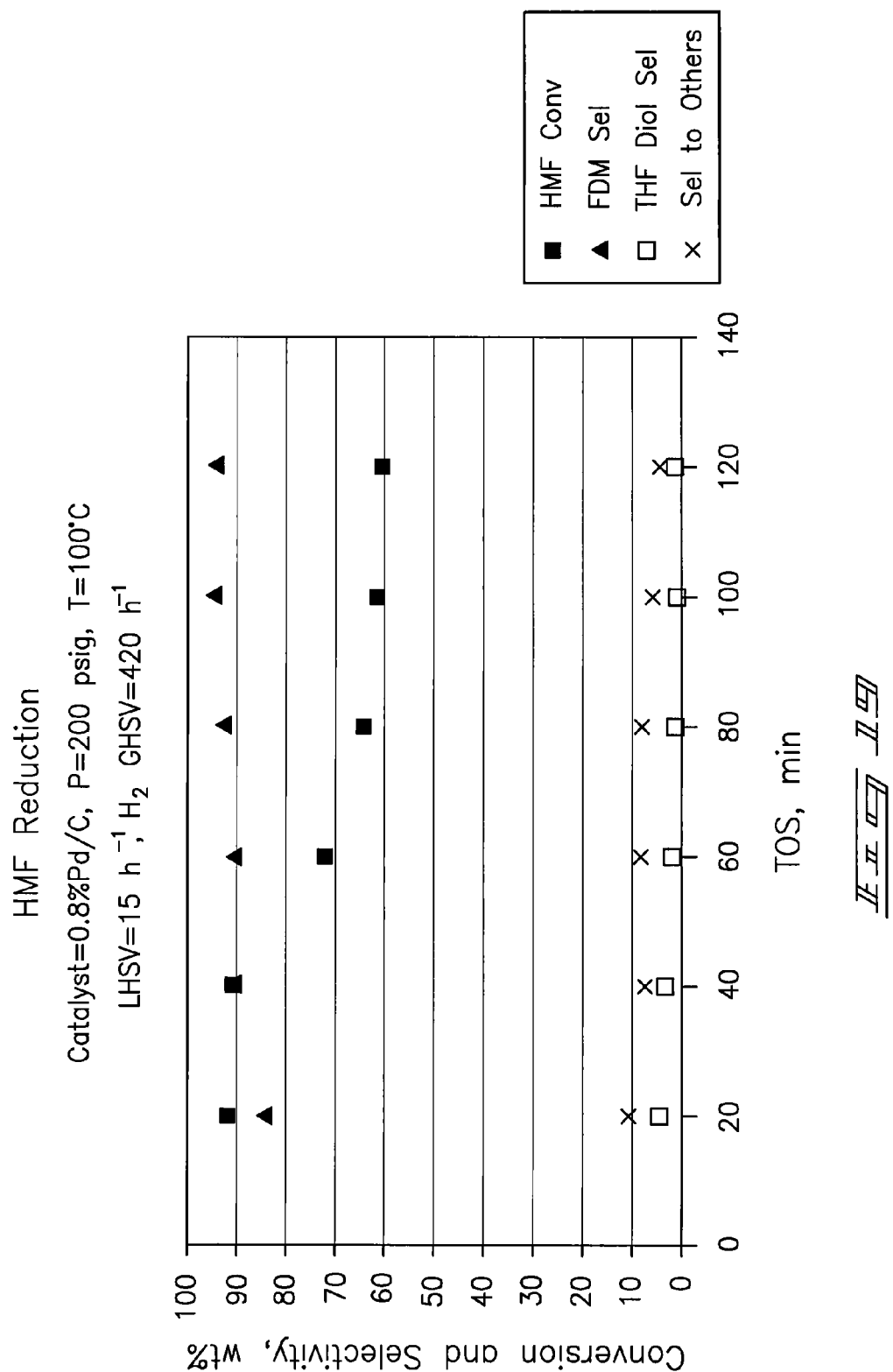
FIG. 19 shows HMF conversion and product selectivity as a function of time on stream utilizing the catalyst of FIG. 15 at reduced pressure and increased temperature and decreased LHSV relative to FIG. 15.
Figure 20:
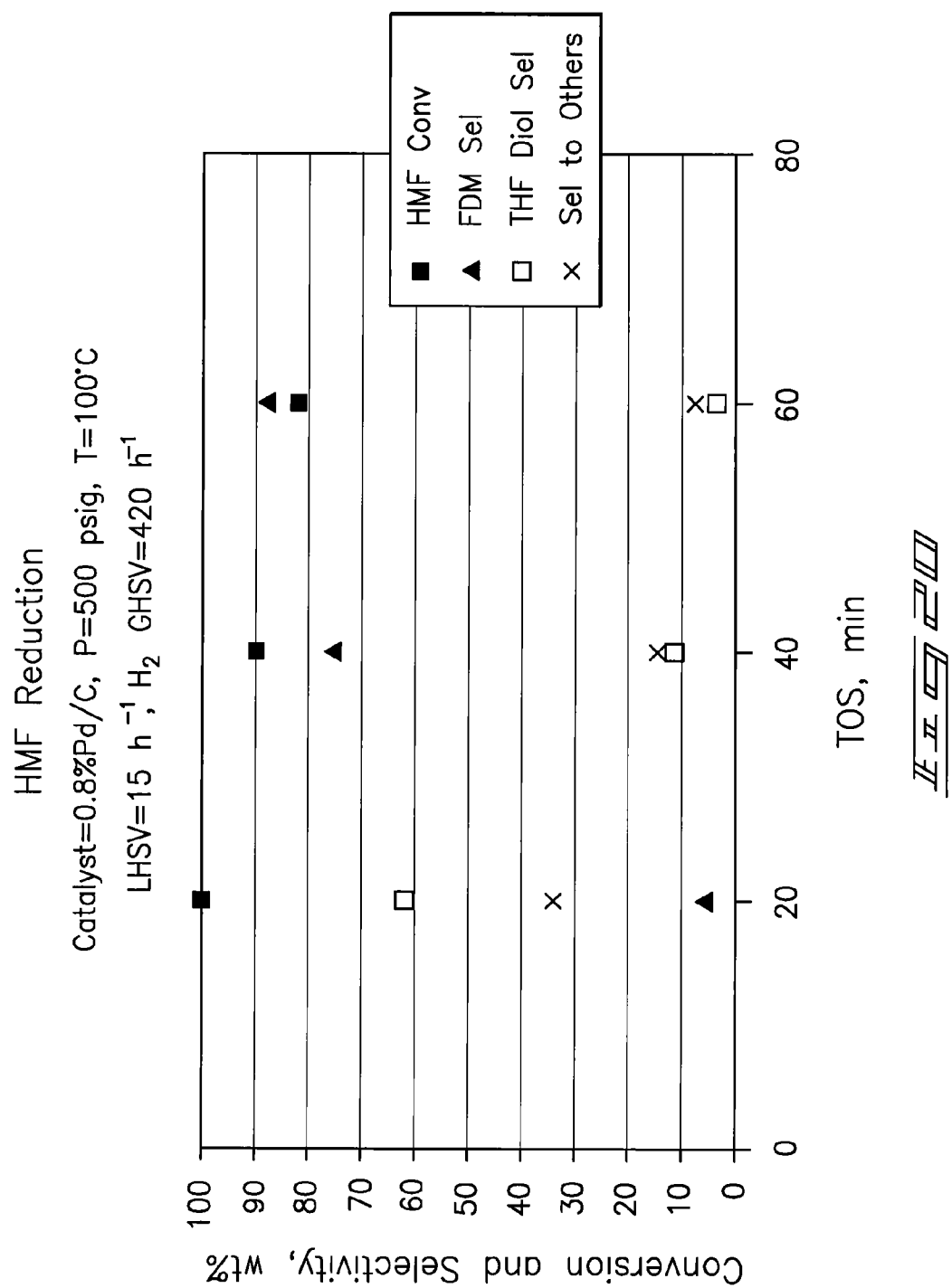
FIG. 20 shows HMF conversion and product selectivity as a function of time on stream for the catalyst of FIG. 15 at an increased temperature and decreased LHSV relative to FIG. 15.
Figure 21:
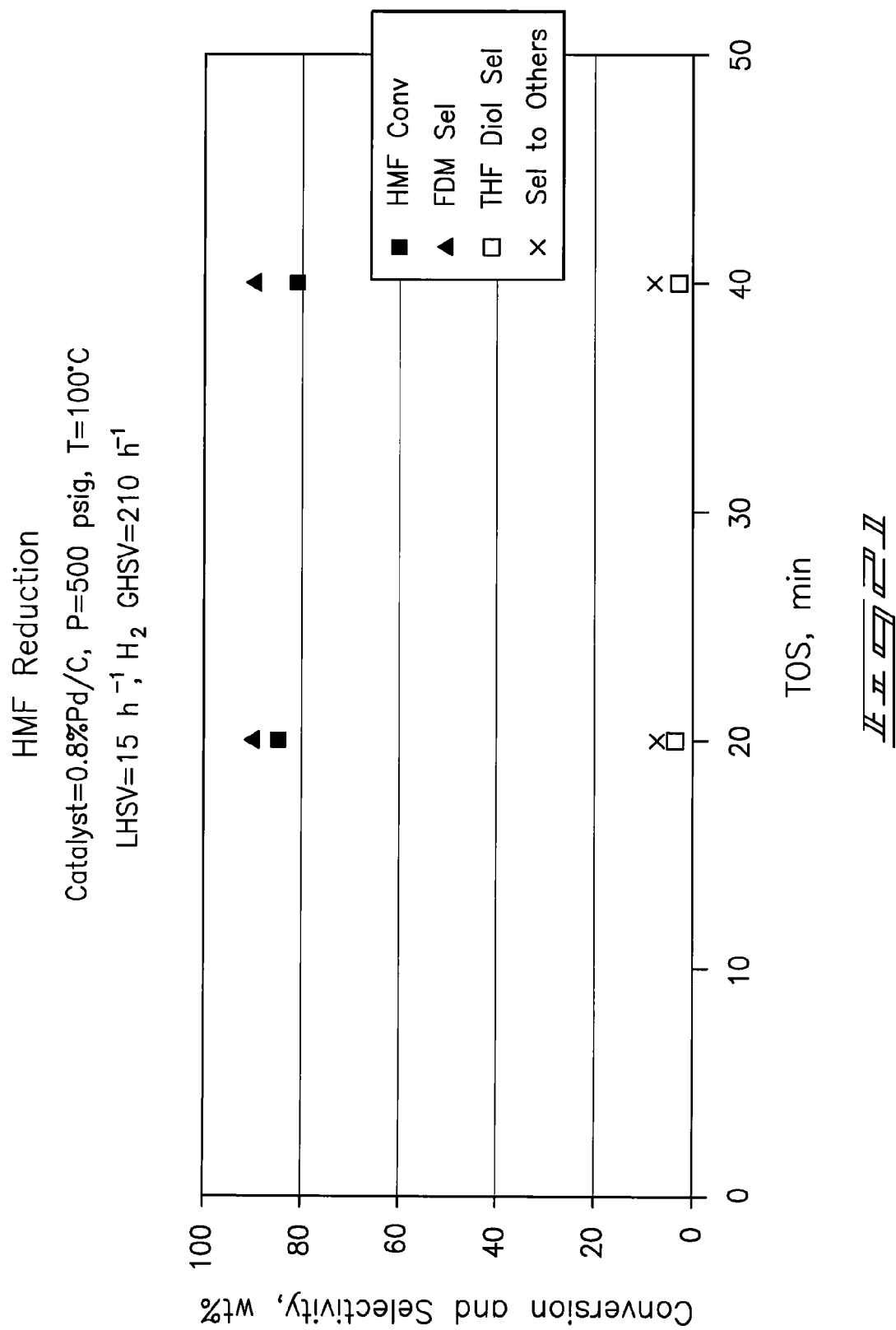
FIG. 21 shows HMF conversion and product selectivity as a function of time on stream for the catalyst of FIG. 15 at a decreased $H_2$ gas hourly space velocity (GHSV), increased temperature, and decreased LHSV relative to FIG. 15.

The following acronyms are used:
FDM=Furan-2,5-dimethanol; GHSV=Gas hourly space velocity; 12HD=1,2-hexanediol; HMF=5-Hydroxymethyl-2-furaldehyde; HMFCA=5-Hydroxymethyl-2-furancarboxylic acid; LHSV=Liquid hourly space velocity; THFA=Tetrahydrofurfuryl alcohol; THF-diol=Tetrahydrofuran-2,5-dimethanol (THFDM); THFDM=Tetrahydrofuran-2,5-dimethanol (THF-diol); 1,2,6-THH=1,2,6-trihydroxyhexane; 1,2,6-Triol=1,2,6-trihydroxyhexane; TOS=Time on Stream

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general, the methodology of the invention encompasses production of furandimethanol (FDM), production of tetrahydrofuran dimethanol (THF dimethanol), or both. More specifically, selective reduction of the aldehyde group on HMF, or both aldehyde groups on alternative starting material diformyl furan (DFF), can be conducted to selectively produce FDM. In particular instances, THF dimethanol is produced as a byproduct. Alternatively, reaction parameters and/or the reaction catalyst can be altered to increase production of, or to selectively produce THF dimethanol. The reaction methodology involves providing HMF or DFF in aqueous solution or within an aqueous mixture. However, the invention contemplates conducting reduction reactions in the presence of one or more organic solvents. In general, the reaction mixture is exposed to a catalyst in accordance with the invention which promotes a reduction of the aldehyde group, and in particular instances the carbon-carbon double bond(s), in water solvent and under relatively mild reaction conditions as compared to conventional methodology. It is to be understood that the invention additionally includes use of alternative starting compounds for reduction utilizing methodology in accordance with the invention, such as HMF derivatives with similarly reducible groups including but not limited to formyl, acid, ester or amide groups.

For aqueous reactions, the relatively mild reaction conditions of reduction methodology in accordance with the invention typically comprise a reaction temperature of less than or equal to 250° C., and in particular instances the reaction temperature will be less than or equal to 100° C. The reduction reaction is performed in the presence of H$_2$. Typically the H$_2$ pressure will be at least 1 atm (14.7 psi) and less than or equal to 1400 psi, more typically between 200-500 psi. Although not limited to a particular pH, the HMF reduction is typically conducted at a pH of about neutral.

For methodology of the invention that utilize fixed-bed continuous flow operation, additional parameters such as liquid and gas flow rates, and feed concentration can be adjusted and in some aspects can affect overall yield.

In one aspect, catalysts of the present invention can comprise at least one of the catalyst metals selected from the group consisting of Pd, Pt, Ru, Rh, Ni, Ir, Cu, Re and Co. In particular instances, catalysts comprising Pd, Pt, Co, Rh, Ir, Cu and/or Ni, can be combination catalysts which additionally include one or more metals selected from the group consisting of Ca, Cr, Mn, Re, Fe, Ru, Rh, Ir, Ni, Pd, Pt, Ag, Au, In, Ge, Cu, Sn, S, Cd, Ga, Al, Mo, Zn and Bi. In particular embodiments, the catalyst can preferably comprise both In and Ir. In alternative aspects, a Cu-chromite catalyst can be preferred.

Where catalysts comprising these metals or combinations of metals are utilized for HMF/HMF-derivative reduction, the catalyst metal can typically be supported by one or more support materials. Such support materials can be, for example, carbon support materials including but not limited to activated carbon support materials, and various inorganic supports such as metal oxide support materials including but not limited to Zr-oxides, Ti-oxides, Al-oxides, Si-oxides, etc. Various exemplary catalysts of the type described above which were utilized for conducting reduction methodology in accordance with the invention are set forth in Tables 1 and 2. Table 1 presents commercially available catalysts while Table 2 presents catalysts prepared in-house for use in the reduction reactions. It is to be understood that the listed catalysts are exemplary and are not intended to limit the scope of the invention.

TABLE 1

Exemplary commercially available catalysts for HMF reduction

| Catalyst Composition | Manufacturer | Lot No/Sample ID |
|---|---|---|
| 5% Pd, 0.5% Cu/C | Engelhard | 787A-15-409-1 |
| 10% Pd/C | Degussa | CC1-2155 |
| 5% Pd, 1% Sn/C | Engelhard | SOC 98186 |
| 5% Pd, 0.15% Fe/C | Engelhard | 787A-8-157-1 |
| 5% Pd, 0.5% Fe/C | Engelhard | 787A-15-417-1 |
| 5% Pd/C | Engelhard | 39658 |
| 5% Pd, 5% Re/C | Engelhard | 6758-17-03 |
| 5% Pd, 5% Re/C | Engelhard | 6555-38-1 |
| 5% Pt(Ge)/C | Engelhard | 43932 |
| 5% Pt(S)/C | Engelhard | 787A-15-321-1 |
| 1.5% Pt, 0.15% Cu/C | Engelhard | 787A-8-153-1 |
| 1.5% Pt, 0.15% Sn/C | Engelhard | 787A-8-152-1 |
| 1.5% Pt, 0.15% Bi/C | Engelhard | 787A-8-151-1 |
| 1.5% Pt, 0.15% Ru/C | Engelhard | 787A-8-150-1 |
| 3% Pt/$Al_2O_3$ | Engelhard | 6849-14-1 |
| 3% Pt/C | Engelhard | 43931 |
| Escat 288 | Engelhard | 324230 |
| 5% Ru/C | AlfaAesar | C10J23 |
| 2.5% Ru/C | Engelhard | 6818-13-2 |
| 5% Ru/$ZrO_2$ | Engelhard | 712A-4-294-1 |
| 5% Ru/C | Johnson Matthey | 072183 |
| 3% Ru/$TiO_2$ (rutile) | Degussa | H7709x/o |
| 3% Ru/$TiO_2$ | Degussa | CC4-251A |
| 5% Rh/C | Heraeus | K-0319 |
| 5% Rh/C | Engelhard | 43671 |
| Ni powder | Mallinckrodt | S-96-674 |
| 2.5% Ni, 2.5% Re/C | Engelhard | 6757-43-2 |
| 4% Ni, 4% Re/C | Engelhard | 6818-15-3 |
| Cu/Cr | SudChemie | G-22/2 |
| Cu/Cr/Mn | United Catalyst (SudChemie) | G-89, 4171-S |
| Cu-chromite | Engelhard | S-02-245 |
| 1.5% Pt, 0.15% Cu on C | Engelhard | 787a-8-153-1 |
| 10% Re on $Al_2O_3$ | Davicat | Al2301 |
| 10% Re on $Al_2O_3$ | Davicat | Al2400 |
| 0.5% Pd on C | Degussa | E181 |
| 5% Rh on C | Degussa | G106 |
| 5% Ru on $ZrO_2$ | Engelhard | Ru on $ZrO_2$ |
| 0.7% Ru on C | Engelhard | 47038 |
| 5% Pd, 1% Sn on C | Engelhard | 5% Pd 1% Sn |
| 2.5% Ni, 2.5% Re on C | Engelhard | 6757-43-2 |
| 5% Pd, 5% Re on C | Engelhard | 6758-17-02 |
| 2.5% Co, 2.5% Re on C | Engelhard | 6818-15-1 |
| 2% Ni, 2.5% Re on C | Engelhard | 6818-20-4 |
| Supported 40% Co | Engelhard | Co-0124 |
| Supported 40% Co | Engelhard | Co-0138 |
| Supported 40% Co | Engelhard | Co-0164 |

TABLE 1-continued

Exemplary commercially available catalysts for HMF reduction

| Catalyst Composition | Manufacturer | Lot No/Sample ID |
|---|---|---|
| 40% Co on $SiO_2$ | Engelhard | Co-0179 |
| Supported 50% Ni | Engelhard | Ni-3210 T |
| Supported 50% Ni | Engelhard | Ni-3288 E |
| Supported Cu | Engelhard | Cu-1186 t 1/8 lot #60" |
| 0.8% Pd on C | Engelhard | Escat 132 |
| 0.5% Pd on C | Engelhard | Escat 138 |
| 0.5% Pt on C | Engelhard | Escat 238 |
| 5% Pt on C | Engelhard | Escat 288 |
| Supported Cu | Sud Chemie | G-132 1/16 ext." |
| Supported Cu | Girdler | G-9 CuMn tab. |
| Supported Cu | Harshaw | Cu-2501 G4-6 |
| 5% Rh on C | Engelhard | Italiana 43664 |
| Supported Cu | Katalco | ICI MeOH cat. CuZnAl |
| 55% Ni on $SiO_2$ | Sud Chemie | C46-7-03 RS |
| 40% Co on $SiO_2$ + $ZrO_2$ | Sud Chemie | G62aExt |
| 40% Co on $SiO_2$ | Sud Chemie | G62aRS |
| 40% Co on $SiO_2$ +$ZrO_2$ | Sud Chemie | G67aRS Ext |
| Supported 50% Ni | Sud Chemie | G69bRS |
| Supported Cu | Sud Chemie | G-99b-13 EF tab. |
| Supported Cu | Sud Chemie | T-4489 rs 3x3 tab |
| 40% Co on $SiO_2$ | United Catalysts | G62RS |
| Supported Cu | United Catalysts | G-89 CuCrMn |
| Supported Cu | United Catalysts | T-4489 CuAl |
| Raney ® 2700-Co | W.R. Grace & Co | Lot# 7865 |
| Raney ® 2724-Co | W.R. Grace & Co | Lot# 8318 |
| Raney ® Cu sponge | Strem Chemicals | Lot# 141625-S |
| Raney ® Ni catalyst | Activated Metals | A-5200 |

TABLE 2

Reduction catalysts prepared in-house.

| Catalyst Composition | Catalyst Composition |
|---|---|
| 5% Co on $SiO_2$ | 5.1% Ir on $SiO_2$ |
| 20% Co on $SiO_2$ | 2.6% Ir, 0.3% Ca on $SiO_2$ |
| 5% Co, 1% Ag on $SiO_2$ | 2.6% Ir, 0.7% Cd on $SiO_2$ |
| 20% Co, 4% Ag on $SiO_2$ | 2.6% Ir, 0.5% Ga on $SiO_2$ |
| 5% Co, 1.8% Au on $SiO_2$ | 2.6% Ir, 0.8% In on $SiO_2$ |
| 20% Co, 7.2% Au on $SiO_2$ | 2.6% Ir, 0.8% Sn on $SiO_2$ |
| 5% Co, 0.4% Ca on $SiO_2$ | 7% Ni, 0.5% Fe on C |
| 20% Co, 1.6% Ca on $SiO_2$ | Supported 20% Ni, 10% Mo |
| 5% Co, 0.6% Cu on $SiO_2$ | 1% Pd on $TiO_2$ (rutile) |
| 20% Co, 2.4% Cu on $SiO_2$ | 1.4% Pd on $SiO_2$ |
| 5% Co, 0.3% Fe on $SiO_2$ | 1.4% Pd, 0.3% Ca on $SiO_2$ |
| 20% Co, 1.2% Fe on $SiO_2$ | 1.4% Pd, 0.7% Cd on $SiO_2$ |
| 5% Co, 0.9% Ir on $SiO_2$ | Pd, Fe on C |
| 20% Co, 3.5% Ir on $SiO_2$ | 1.4% Pd, 0.5% Ga on $SiO_2$ |
| 5% Co, 0.3% Mn on $SiO_2$ | 1.4% Pd, 0.8% In on $SiO_2$ |
| 20% Co, 1.2% Mn on $SiO_2$ | 1.4% Pd, 0.8% Sn on $SiO_2$ |
| 5% Co, 0.3% Ni on $SiO_2$ | Pt on C |
| 20% Co, 1.2% Ni on $SiO_2$ | 2.6% Pt on $SiO_2$ |
| 5% Co, 0.5% Pd on $SiO_2$ | 5% Pt on $SiO_2$ |
| 20% Co, 2% Pd on $SiO_2$ | 5% Pt on Al2O3 |
| 5% Co, 0.9% Pt on $SiO_2$ | 2.6% Pt, 0.3% Ca on $SiO_2$ |
| 20% Co, 3.5% Pt on $SiO_2$ | 2.6% Pt, 0.7% Cd on $SiO_2$ |
| 5% Co, 0.5% Rh on $SiO_2$ | 2.6% Pt, 0.5% Ga on $SiO_2$ |
| 20% Co, 2% Rh on $SiO_2$ | 2.6% Pt, 0.8% In on $SiO_2$ |
| 0.65% Ir on $SiO_2$ | 2.6% Pt, 0.8% Sn on $SiO_2$ |
| 1.3% Ir on $SiO_2$ | 1.4% Rh on $SiO_2$ |
| 2.6% Ir on $SiO_2$ | 1.4% Rh, 0.8% In on $SiO_2$ |
| 5.1% Ir on SiO2 | 1.4% Rh, 0.8% Sn on $SiO_2$ |

For preparation of the catalysts presented in Table 2, support material was manually weighed into a vial, impregnated with the first metal solution and allowed to dry in air at ambient pressure overnight. Where a second metal was utilized, a second metal solution was then added. Optionally, the vial could be exposed to a flow of air (100 mL/min) and heated to 400° C. for 4 h with a ramp of about 5° C./min. The vial was then placed in a catalyst reduction reactor and reduced at 250-300° C. with a ramp of 1-2° C./min and held for 2-4 h under a flow of $H_2$ (100 mL/min). After reduction, the catalyst reduction reactor was sealed under an $N_2$ environment and moved to a glovebox where the catalyst could be loaded into the conversion reactor.

Each of the catalysts listed in Tables 1 and 2 was tested batch-wise under mild conditions (typical conditions: 500 psi $H_2$ and 60° C. for a reaction time of 1 hour) and/or in a fixed-bed continuous flow reactor. Of the listed catalysts tested batch-wise, Co, Pd, Ir and Pt catalysts resulted in the highest yields of FDM. Test reactions were also conducted batch wise at temperatures as low as 30° C. and showed good conversion of HMF. The batch testing additionally included experiments conducted as low as 100 psi $H_2$, also showing good conversion. Selectivity of HMF to FDM is often highest upon just reaching approximately 100% conversion of HMF, with continued reaction times sometimes resulting in over-reduction.

Reactions were also performed utilizing various of the catalysts presented in the Tables in fixed-bed reactor systems. Such studies suggest that, of the catalysts tested, Pd, Pt, Co and Cu—Cr catalysts can be preferred for FDM production under the conditions utilized.

In addition to the catalysts described above, reaction methodology of the invention can alternatively be conducted utilizing RANEY® type metals such as RANEY® nickel, RANEY® cobalt or RANEY® copper.

With respect to the RANEY® type metals, RANEY® cobalt appears to be both highly active and selective for FDM production from HMF. RANEY® Ni is also able to catalyze reduction of HMF to FDM under the reaction conditions of the present invention. RANEY® copper also shows ability to produce FDM under the mild reaction conditions, however such metal is less reactive and gives a different product distribution than was observed for RANEY® cobalt or RANEY® Ni catalyzed reductions.

EXAMPLE 1

Selective Reduction of HMF Utilizing Pd/C

To 10 mL of water in a small pressure autoclave (45 mL total volume) was added 0.2289 g of dry Pd/C catalyst (commercially available 0.8% Pd on carbon). A magnetic stir bar was added and the vessel was sealed. The reactor was purged with $N_2$ and was pressure tested for leaks at 500 psi. After confirming an absence of leaks, the vessel was vented, the line was removed and 0.4513 g of HMF dissolved in 5 mL of water was added utilizing a small syringe and needle through the 1/16 inch fitting on the head of the vessel.

The vessel was then purged with $N_2$, purged with $H_2$ and pressurized to 500 psi $H_2$. The reaction vessel was isolated from the $H_2$ feed line by a valve downstream from the pressure gauge. The reactor was brought to a reaction temperature of 60° C. in less than 5 minutes. After 2 hours reaction time (measured from the point of reaching 60° C.) the pressure within the vessel was determined to be 330 psi. The vessel was then vented and purged with $N_2$ and the gas line removed to allow sampling of vessel contents. Approximately 1 mL of sample was removed utilizing an approximately 5 inch needle, and the sample was filtered utilizing a 0.2 micron syringe filter. The gas line was then reconnected and the vessel purged with $N_2$ followed by $H_2$ and was re-pressurized to 500 psi $H_2$.

Sampling was repeated after 4 hours and the reaction was stopped after removing the 4 hour sample. Each of the 2 hour and 4 hour samples was diluted by 50% and was analyzed by liquid chromatography (LC). The results showed that by 2 hours the HMF conversion was 100% with 51% selectivity to FDM due to over-reduction (as apparent by the presence of THF dimethanol).

EXAMPLE 2

Reduction of HMF Utilizing RANEY® Metals

Reduction reactions were performed utilizing RANEY® cobalt, RANEY® copper and RANEY® nickel in independent reactions. The reduction reactions were performed at 60° C. and 500 psi $H_2$ for at least 2 hours. The experiment conducted utilizing RANEY® cobalt resulted in a 100% HMF conversion with 97% selectivity for FDM upon reacting for 2 hours. As indicated above, RANEY® copper was less reactive and resulted in a different product distribution.

EXAMPLE 3

Reduction of HMF with Production of THF Dimethanol

A commercially available nickel powder catalyst (Mallinckrodt Specialty Chemical Company, Calsicat, S-96-674, #69F-093A, E-473P L, Dec. 6, 1996) was utilized. The catalyst was received and stored under water.

1 mL of catalyst slurry was placed in a glass liner and 9 mL of water added. A magnetic stir bar was added and the liner sealed in a 45 mL autoclave. The autoclave was purged and pressure/leak tested to 500 psi with hydrogen. The autoclave was vented and 0.45 grams of HMF dissolved in 5 mL of water was added. The reactor was purged again, and pressurized to 500 psi with hydrogen. The desired temperature of 60° C. was achieved upon heating for approximately 5 minutes and was maintained for 2 hours at which time the first sample was removed and analyzed by LC. HMF conversion was 99% with selectivity to FDM of 84%. Over reduction of FDM to THF dimethanol occurred with a selectivity to THF dimethanol of 10%.

After 4 hours at 60° C. a second sample was removed and analyzed. Conversion of HMF was 100% with more over reduction, selectivity to FDM dropped to 77% and selectivity to THF dimethanol increased to 17%. At 4 hours the temperature was increased to 100° C. and pressure increased to 950 psi hydrogen. After 3 hours of additional reaction under these conditions, FDM selectivity had dropped to 3% and THF dimethanol selectivity increased to 95%.

In fixed-bed continuous flow experiments using the same or similar catalysts and reaction conditions described above, alternative parameters such as gas and liquid flow rates, and feed concentrations were also independently varied to study the effect of such variations on conversion, yield and selectivity. A first set of studies was performed utilizing cobalt metal on $SiO_2$ support material with varying parameters including temperature, $H_2$ pressure, feed concentration, and flow rate parameters. The results of such studies are presented in a series of graphs set forth in FIGS. 1-14.

Similar studies were performed utilizing a palladium metal on carbon support catalyst. For both the palladium and the cobalt catalyst studies, a fixed-bed reactor was utilized to allow sample flow rate to be studied. The results of independent variants of flow rate, reaction temperature, and pressure for the Pd/C catalyst studies are presented in FIGS. 15-21. Tables 3 and 4 show the effect of pressure at 70° C. and 100° C. respectively utilizing the Pd/C catalyst.

TABLE 3

Pressure Effect (T = 70° C., data taken at TOS = 60 minutes)

|  | P = 500 psig | P = 800 psig |
|---|---|---|
| HMFConv, wt % | 57.29 | 51.71 |
| FDM Sel, wt % | 88.36 | 84.07 |
| THF Diol Sel, wt % | 3.78 | 5.68 |
| Sel to Others, wt % | 7.86 | 10.25 |

TABLE 4

Pressure Effect (T = 100° C., data taken at TOS = 60 minutes)

|  | P = 200 psig | P = 500 psig |
|---|---|---|
| HMFConv, wt % | 72.68 | 95.32 |
| FDM Sel, wt % | 91.19 | 87.93 |
| THF Diol Sel, wt % | 1.28 | 4.79 |
| Sel to Others, wt % | 7.53 | 7.28 |

Figure 22:
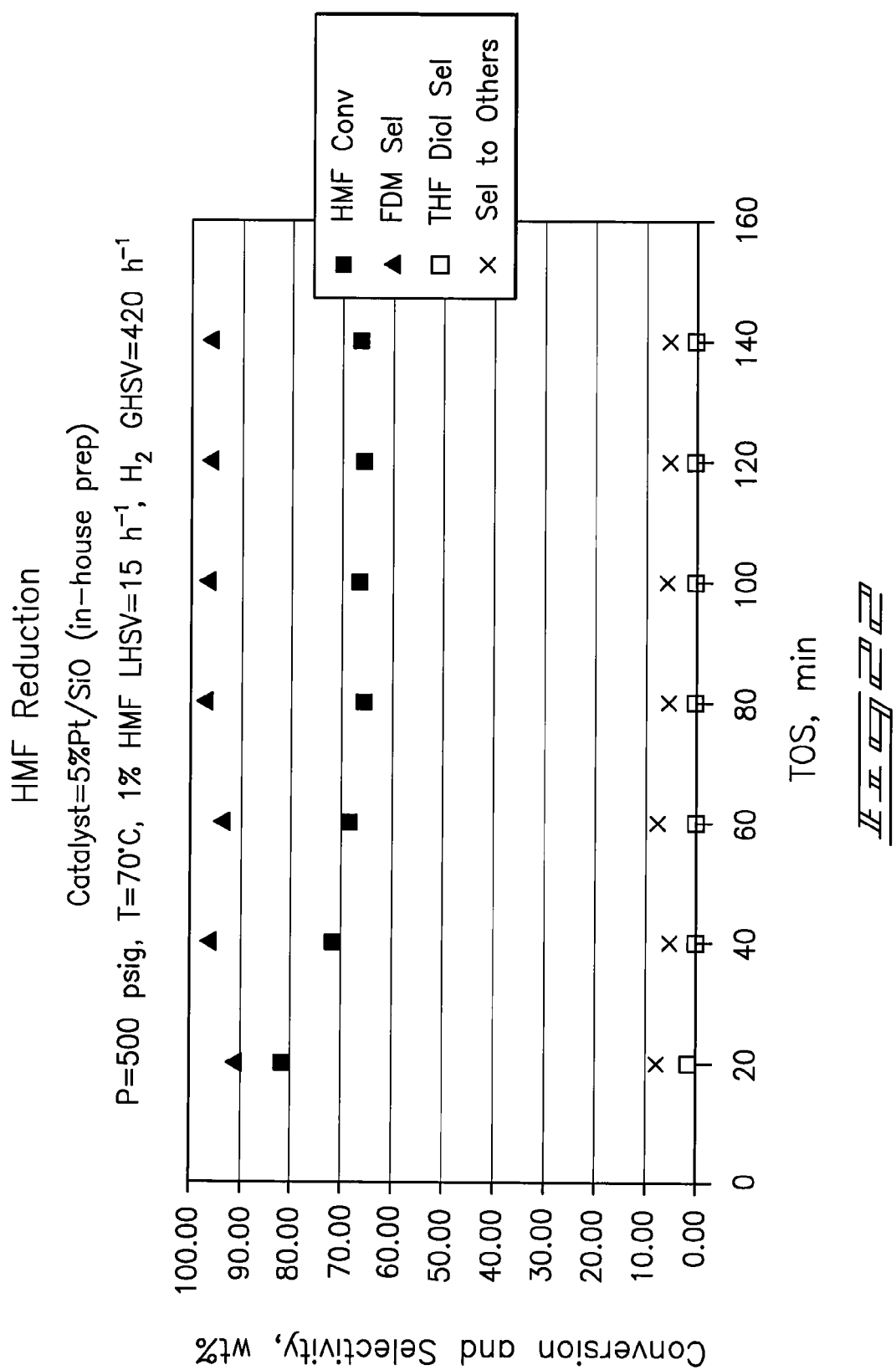
FIG. 22 shows HMF conversion and product selectivity as a function of time on stream for a continuous flow reactor utilizing a Pt on $SiO_2$ support (in-house prep) catalyst and a base set of reaction parameters in accordance with one aspect of the invention.
Figure 23:
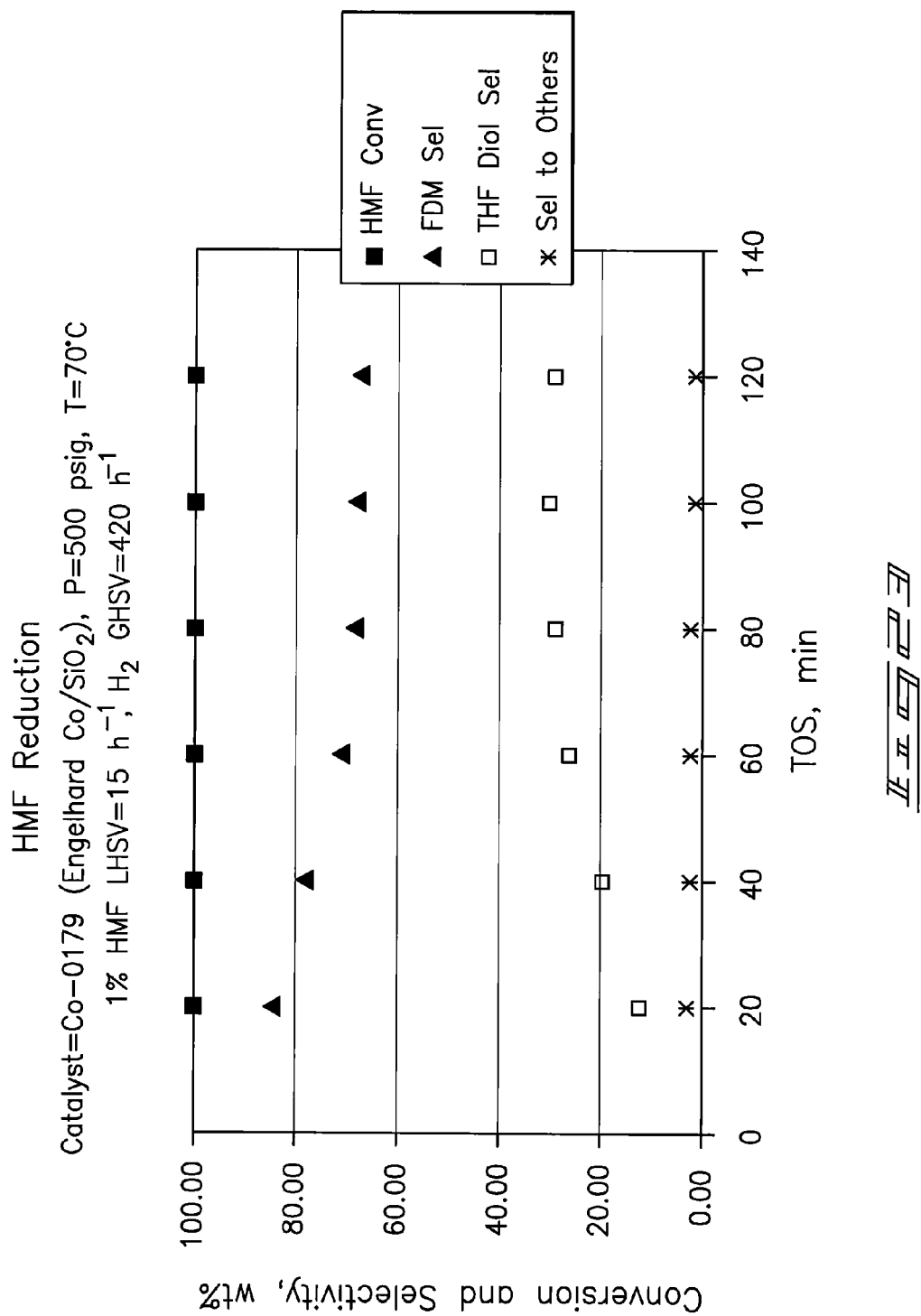
FIG. 23 shows HMF conversion and product selectivity as a function of time on stream for a continuous flow reaction utilizing another Co/$SiO_2$ catalyst and a base set of reaction of parameters in accordance with another aspect of the invention.
Figure 24:
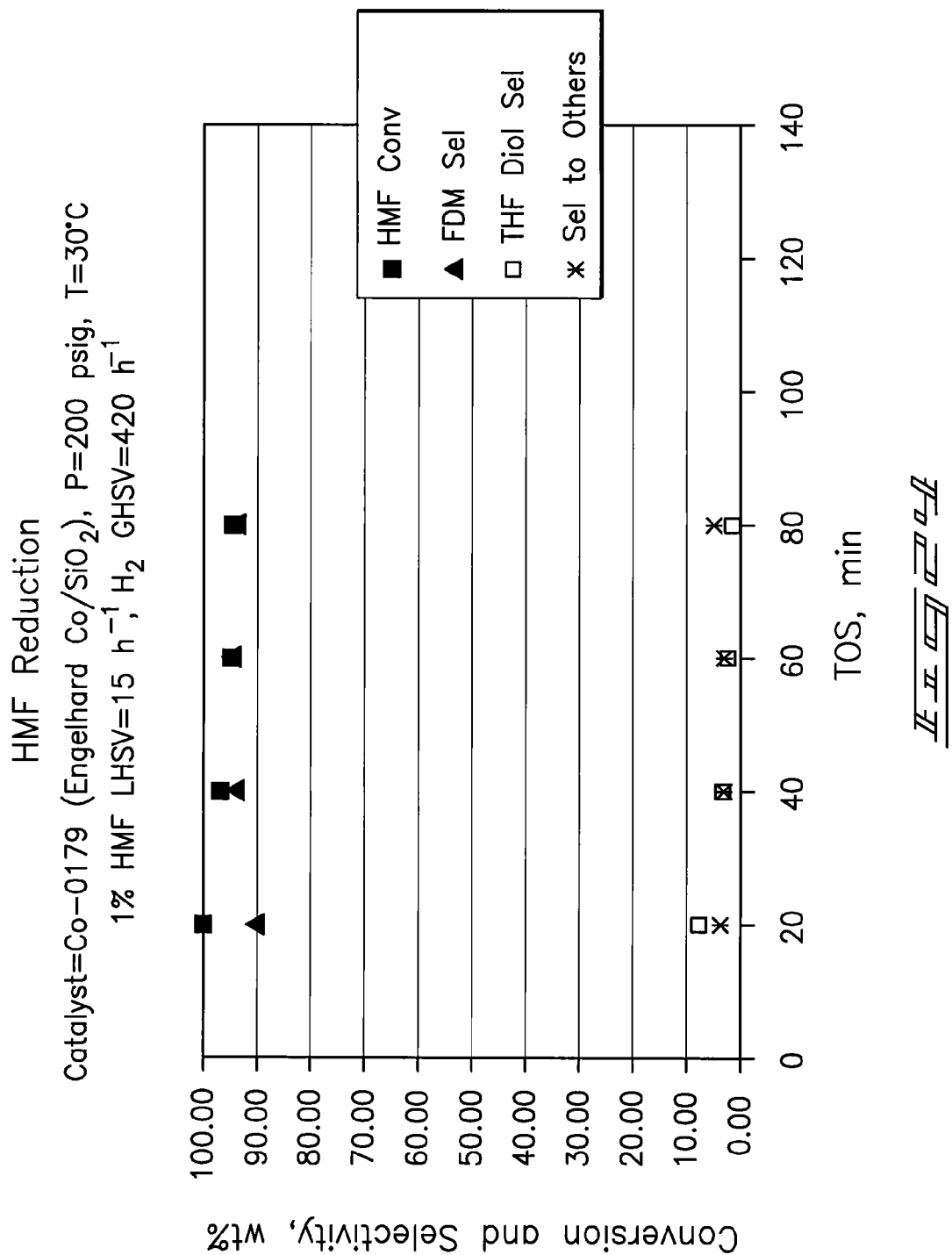
FIG. 24 shows HMF conversion and product selectivity as a function of time on stream utilizing the catalyst of FIG. 23 at a decreased pressure and decreased temperature relative to FIG. 23.
Figure 25:
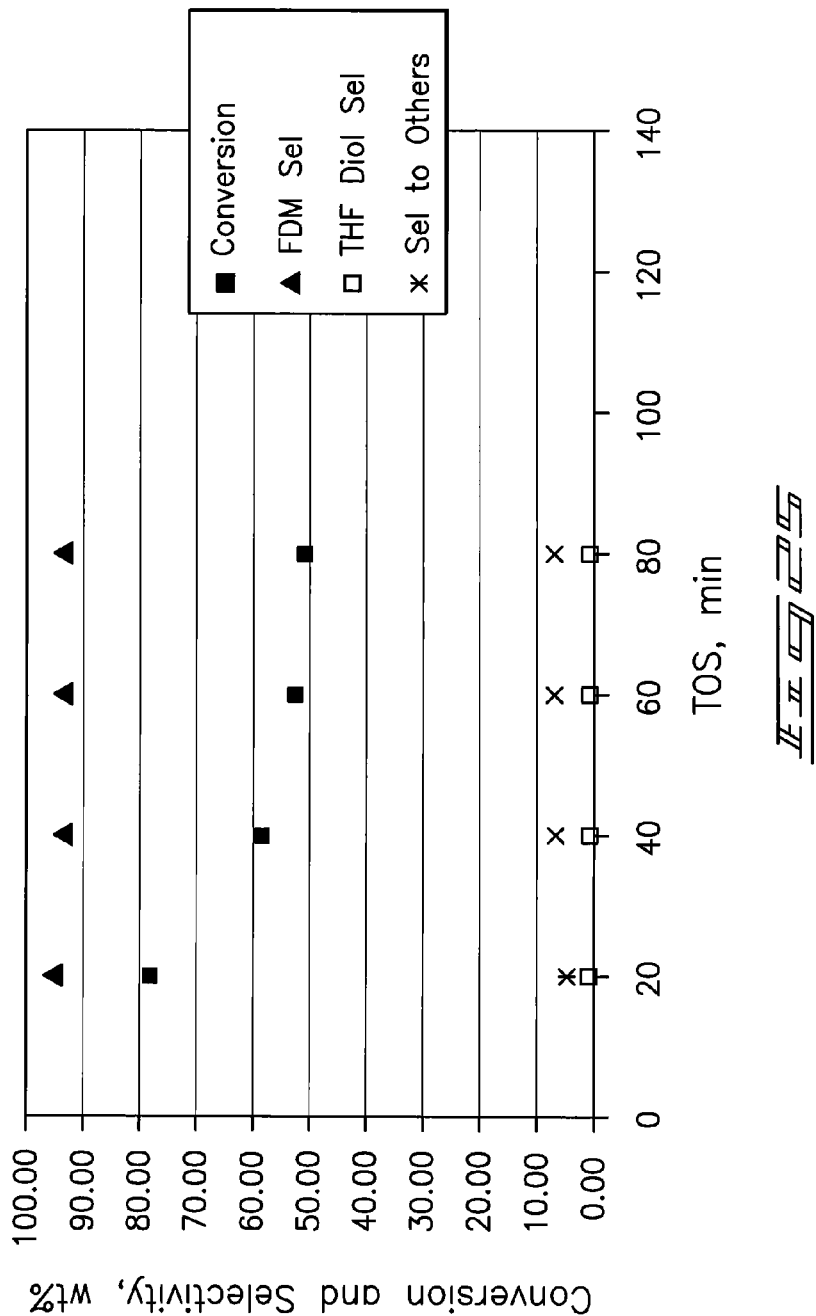
FIG. 25 shows HMF conversion and product selectivity as a function of time on stream utilizing the catalyst of FIG. 23 at a decreased pressure and decreased temperature with an increased HMF feed concentration relative to FIG. 23.
Figure 26:
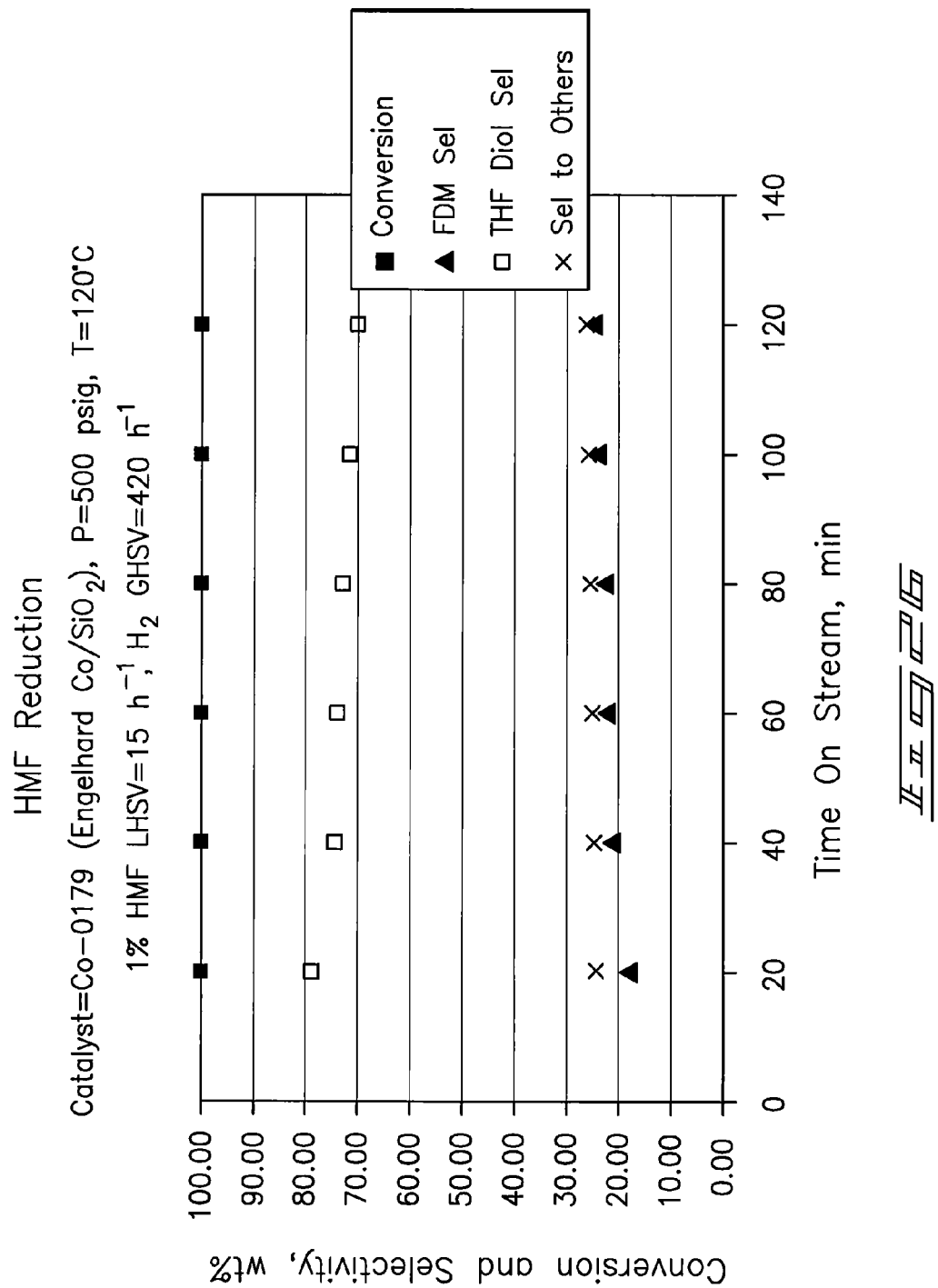
FIG. 26 shows HMF conversion and product selectivity as a function of time on stream for the catalyst of FIG. 23 at an increased temperature relative to FIG. 23.
Figure 27:
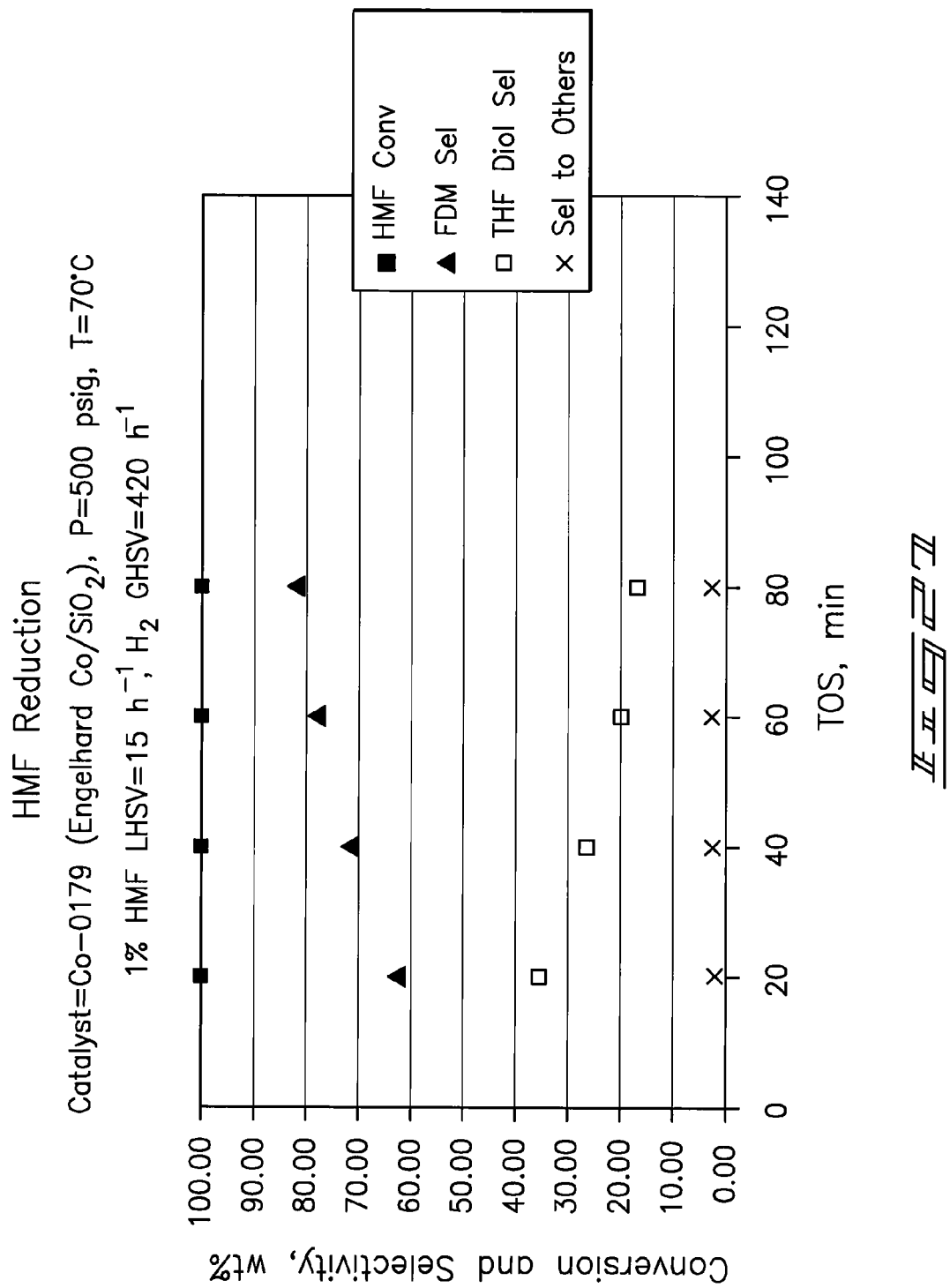
FIG. 27 shows HMF conversion and product selectivity as a function of time on stream for the catalyst of FIG. 23 at the parameters used in FIG. 23.
Figure 28:
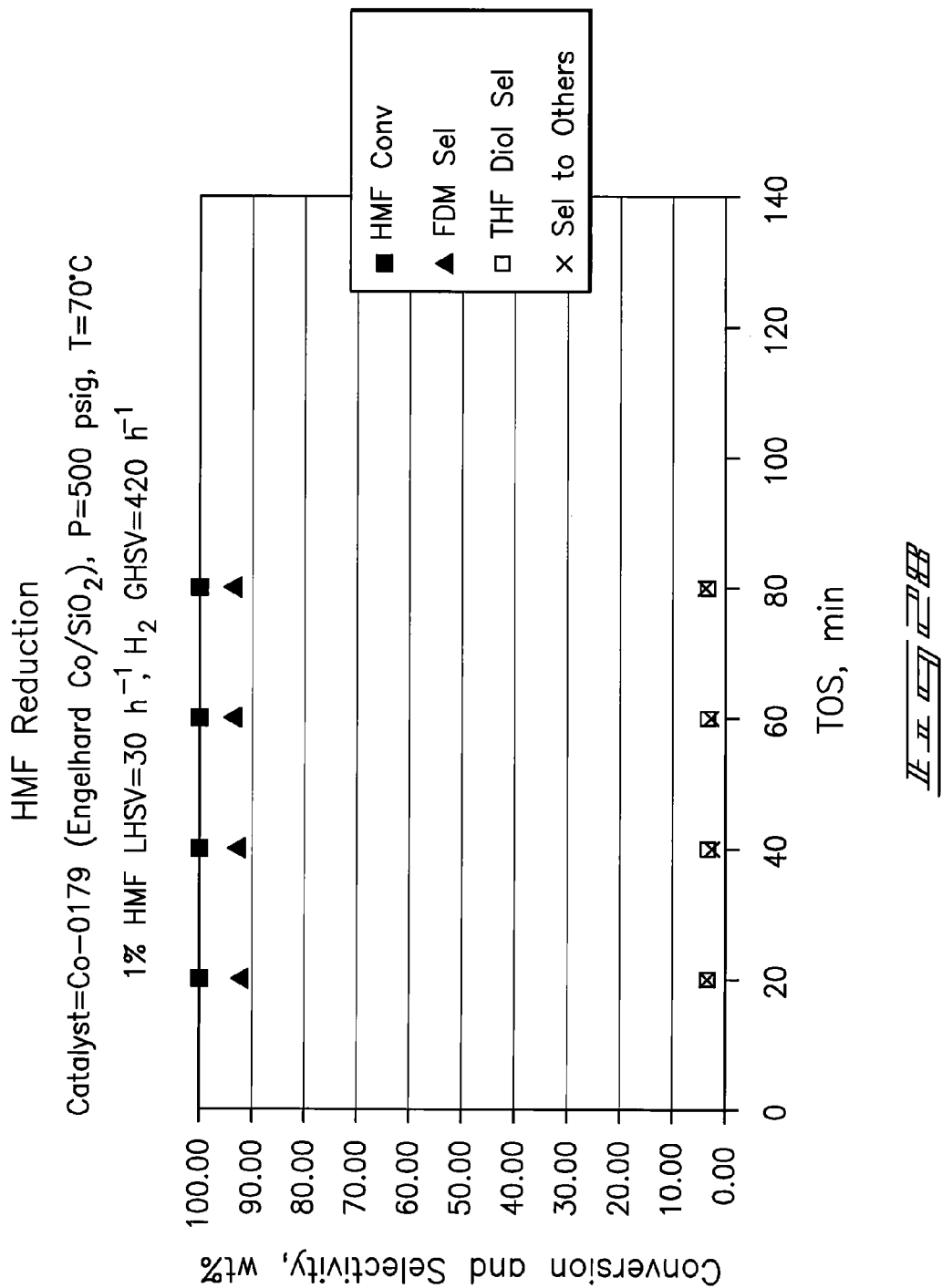
FIG. 28 shows HMF conversion and product selectivity as a function of time on stream for the catalyst of FIG. 23 utilizing an increased LHSV relative to FIG. 23.
Figure 29:
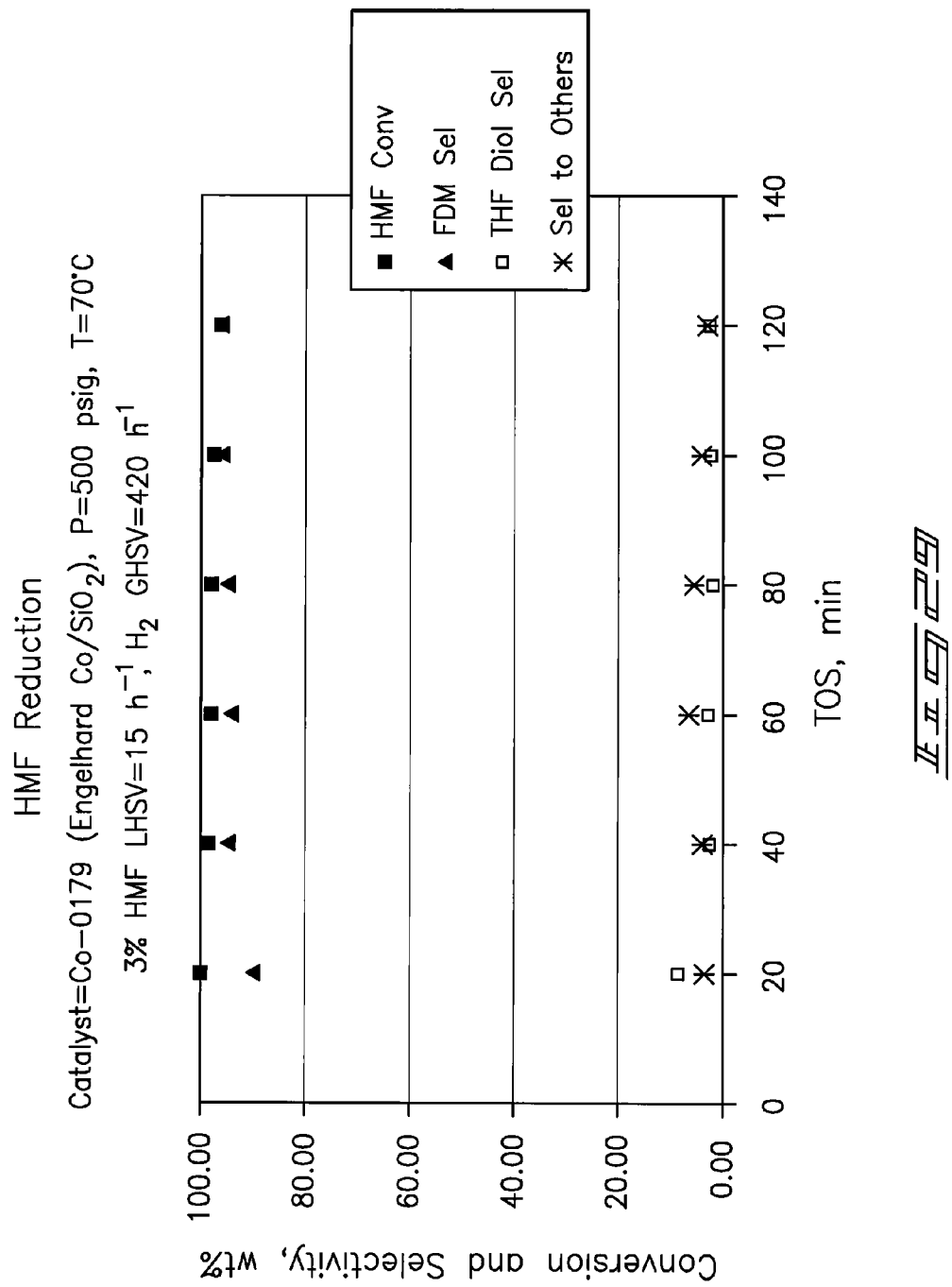
FIG. 29 shows HMF conversion and product selectivity as a function of time on stream for the catalyst of FIG. 23 utilizing an increased HMF feed concentration relative to FIG. 23.
Figure 30:
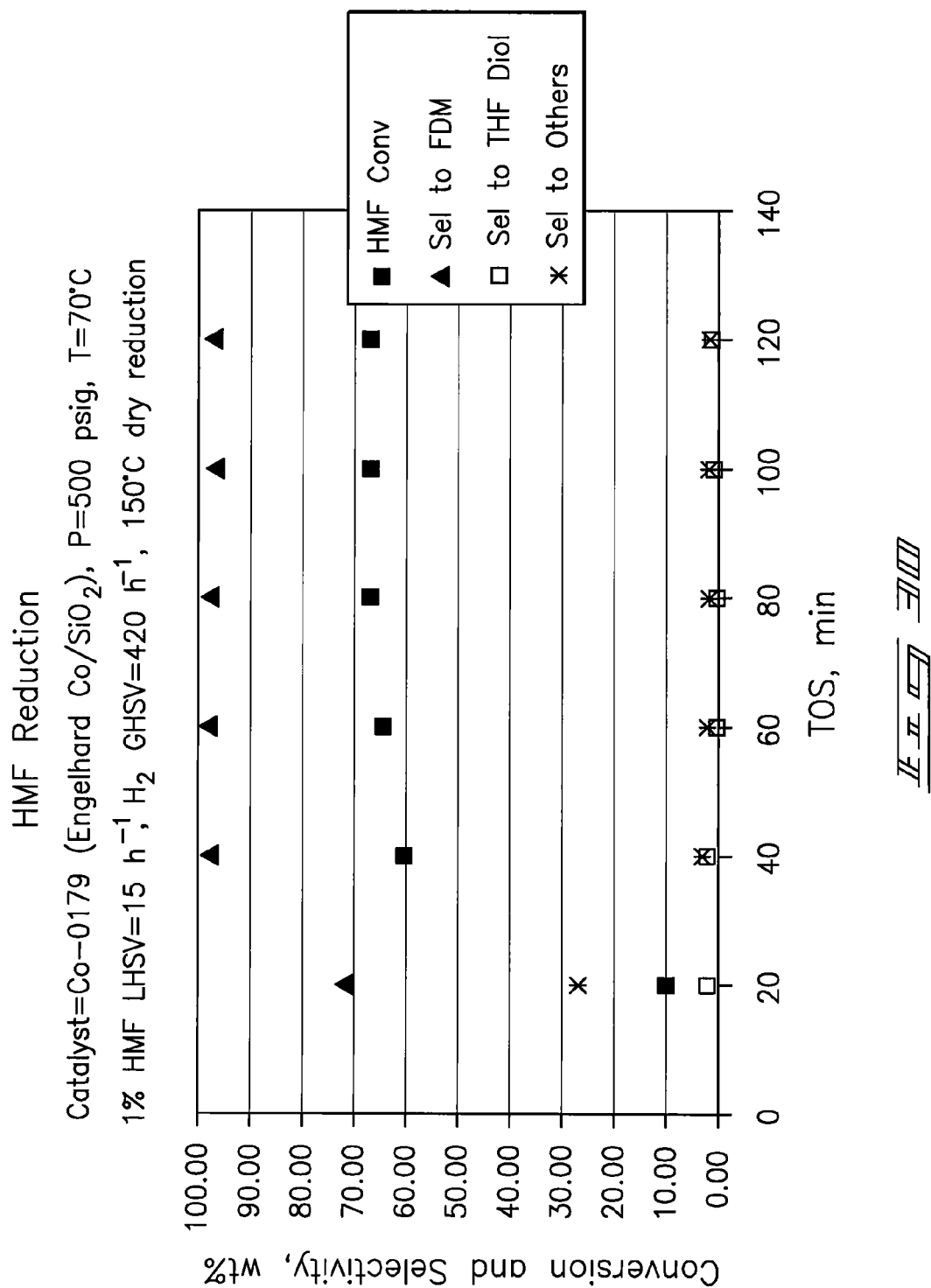
FIG. 30 shows HMF conversion and product selectivity as a function of time on stream utilizing the catalyst of FIG. 23 and the parameters of FIG. 23 where the catalyst was pretreated by dry reduction at 150° C.
Figure 31:
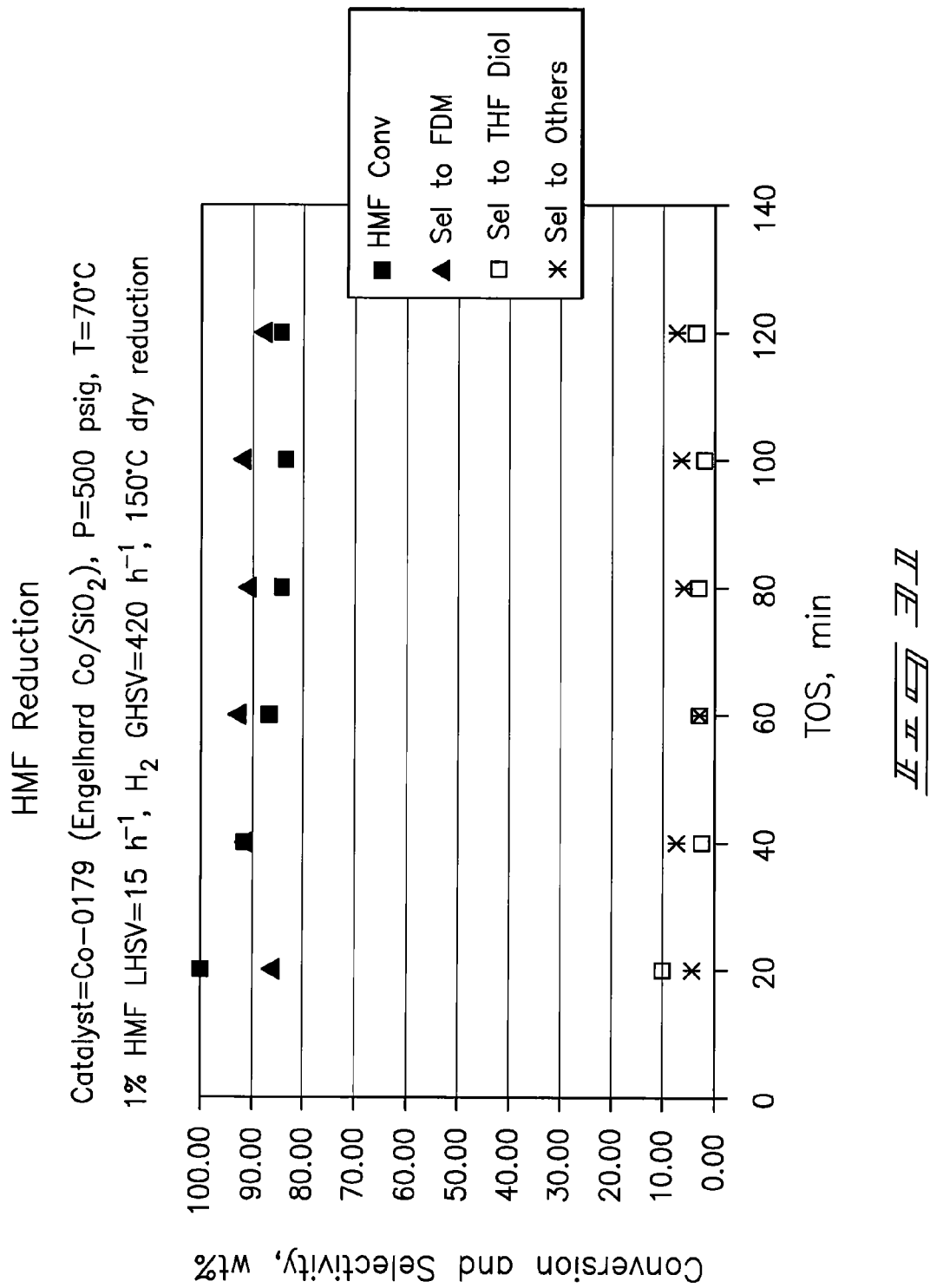
FIG. 31 shows HMF conversion and product selectivity as a function of time on stream for the catalyst of FIG. 23 after 150° C. dry reduction utilizing the parameters of FIG. 23.
Figure 32:
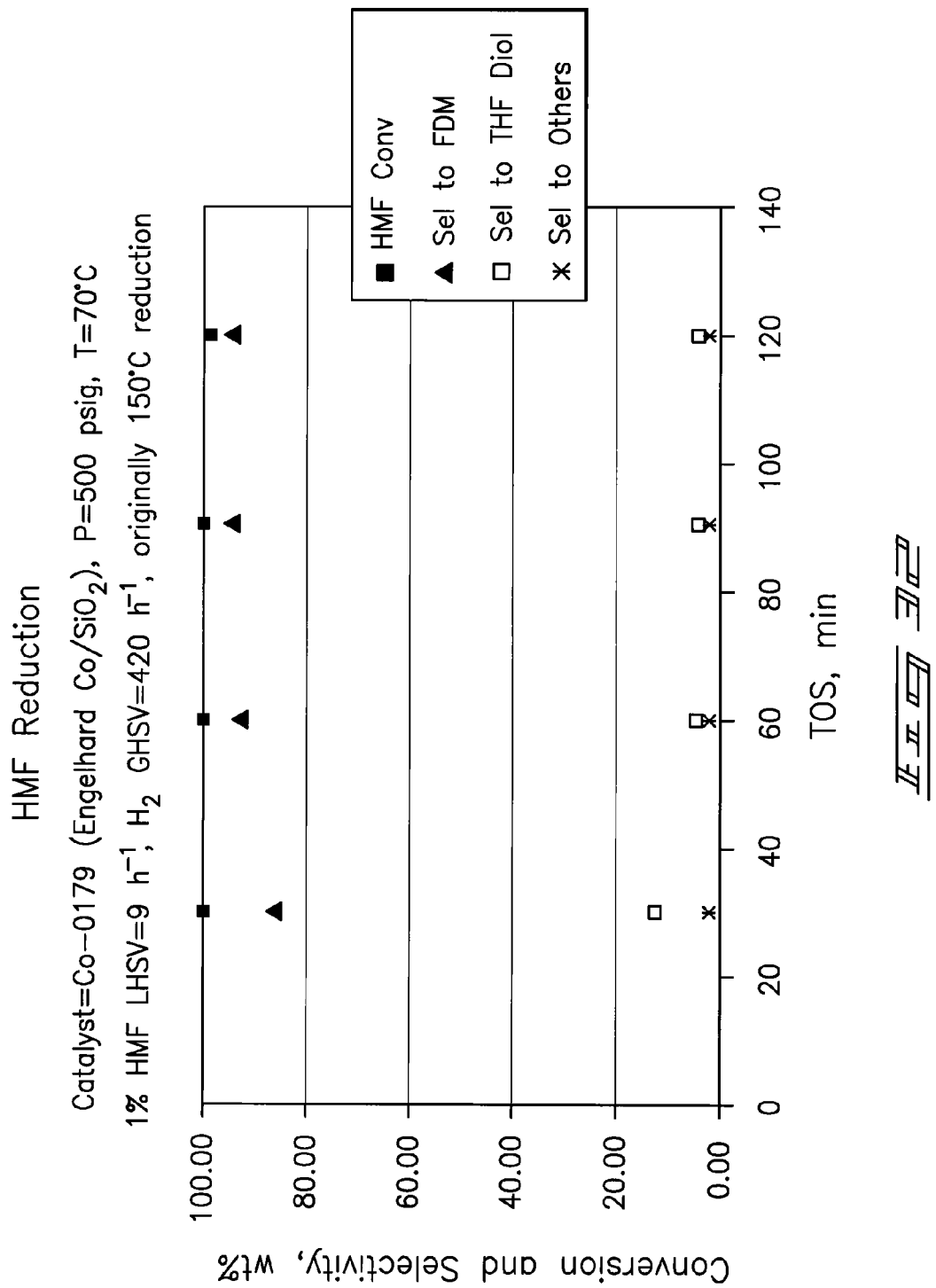
FIG. 32 shows HMF conversion and product selectivity as a function of time on stream for the catalyst of FIG. 23 reduced at 150° C. at a decreased LHSV.
Figure 33:
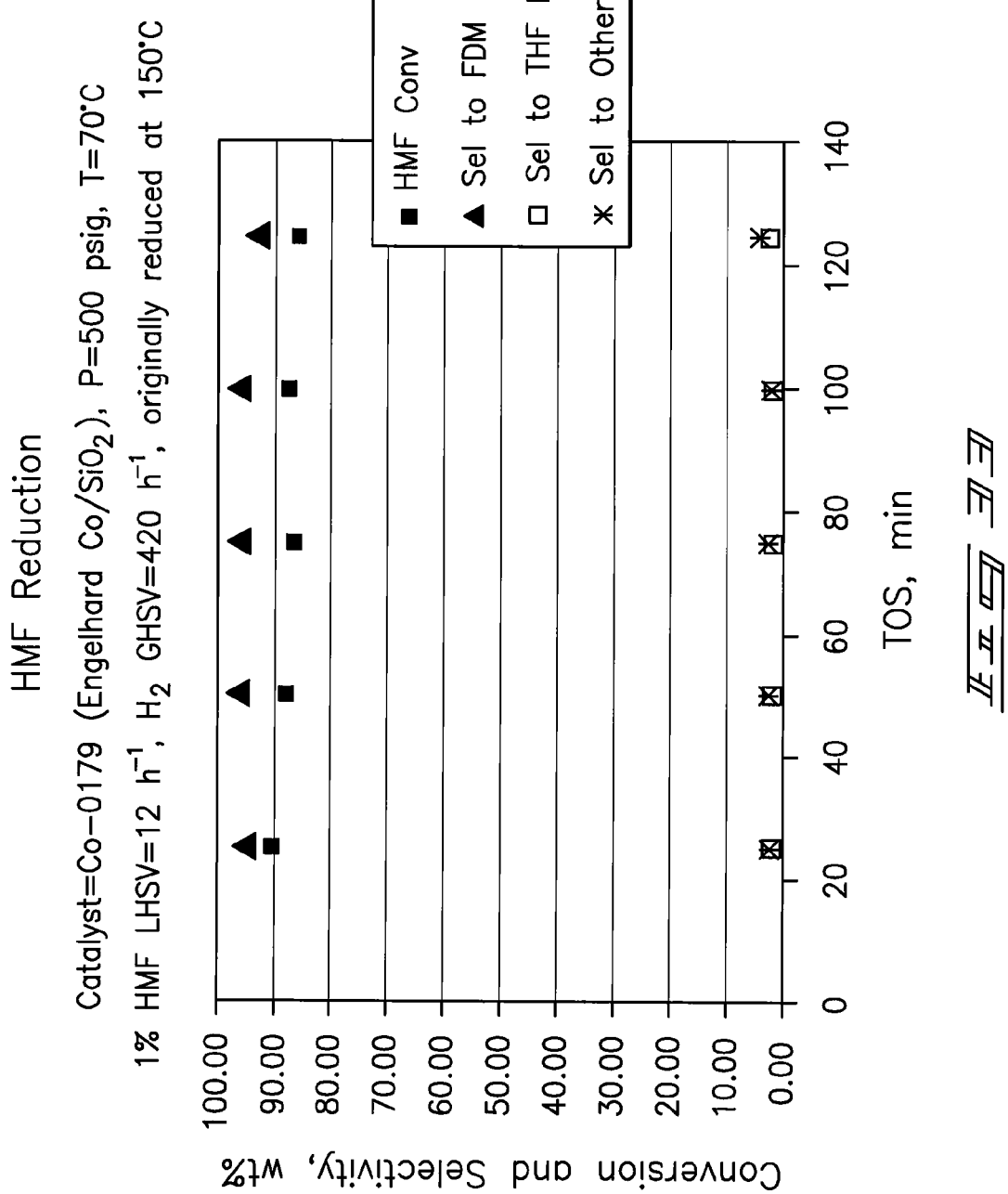
FIG. 33 shows HMF conversion and product selectivity as a function of time on stream for the catalyst of FIG. 23 reduced at 150° C. at a decreased LHSV relative to FIG. 23.
Figure 34:
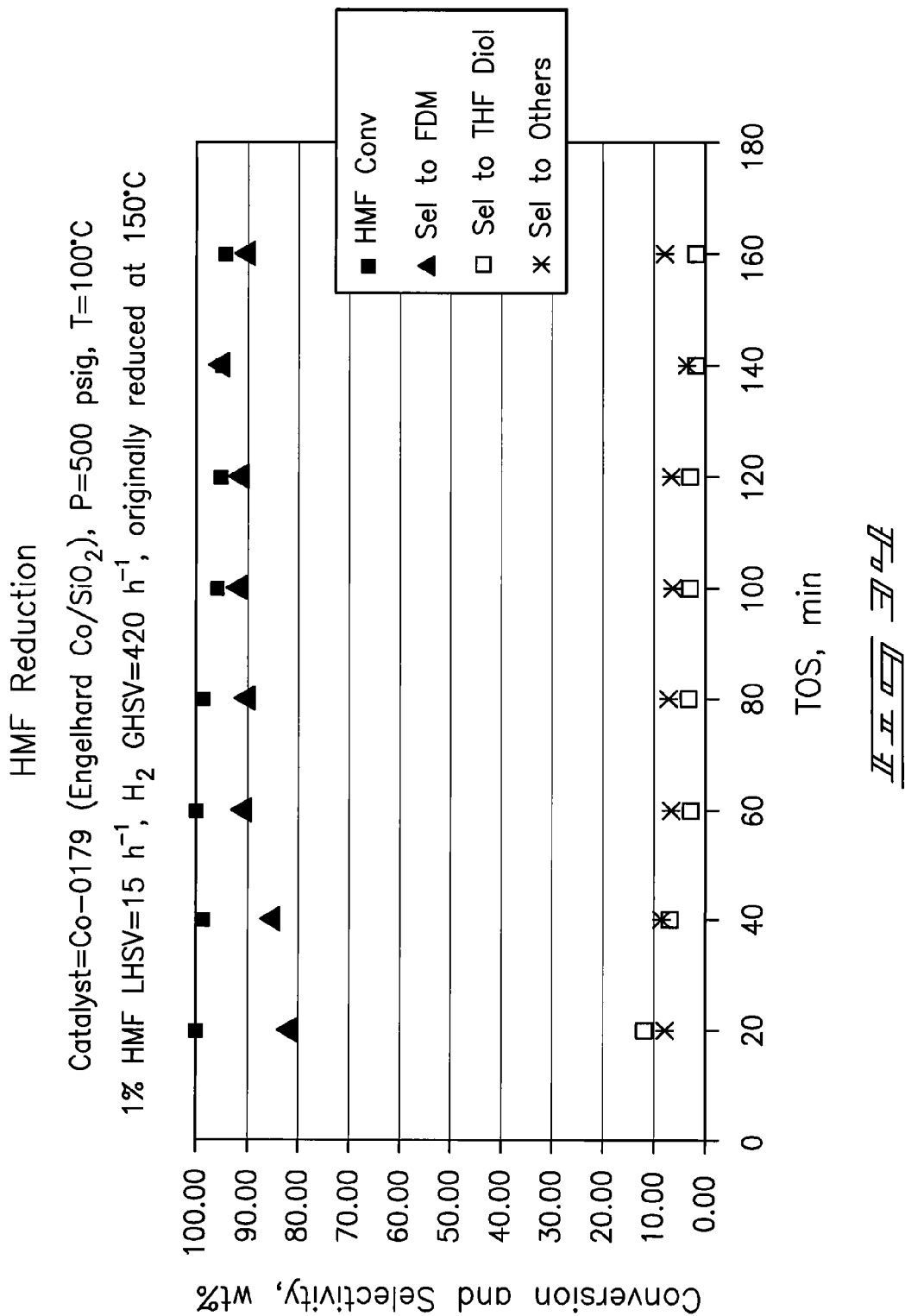
FIG. 34 shows HMF conversion and product selectivity as a function of time on stream for the catalyst of FIG. 23 reduced at 150° C. at an increased reactor temperature relative to FIG. 23.
Figure 35:
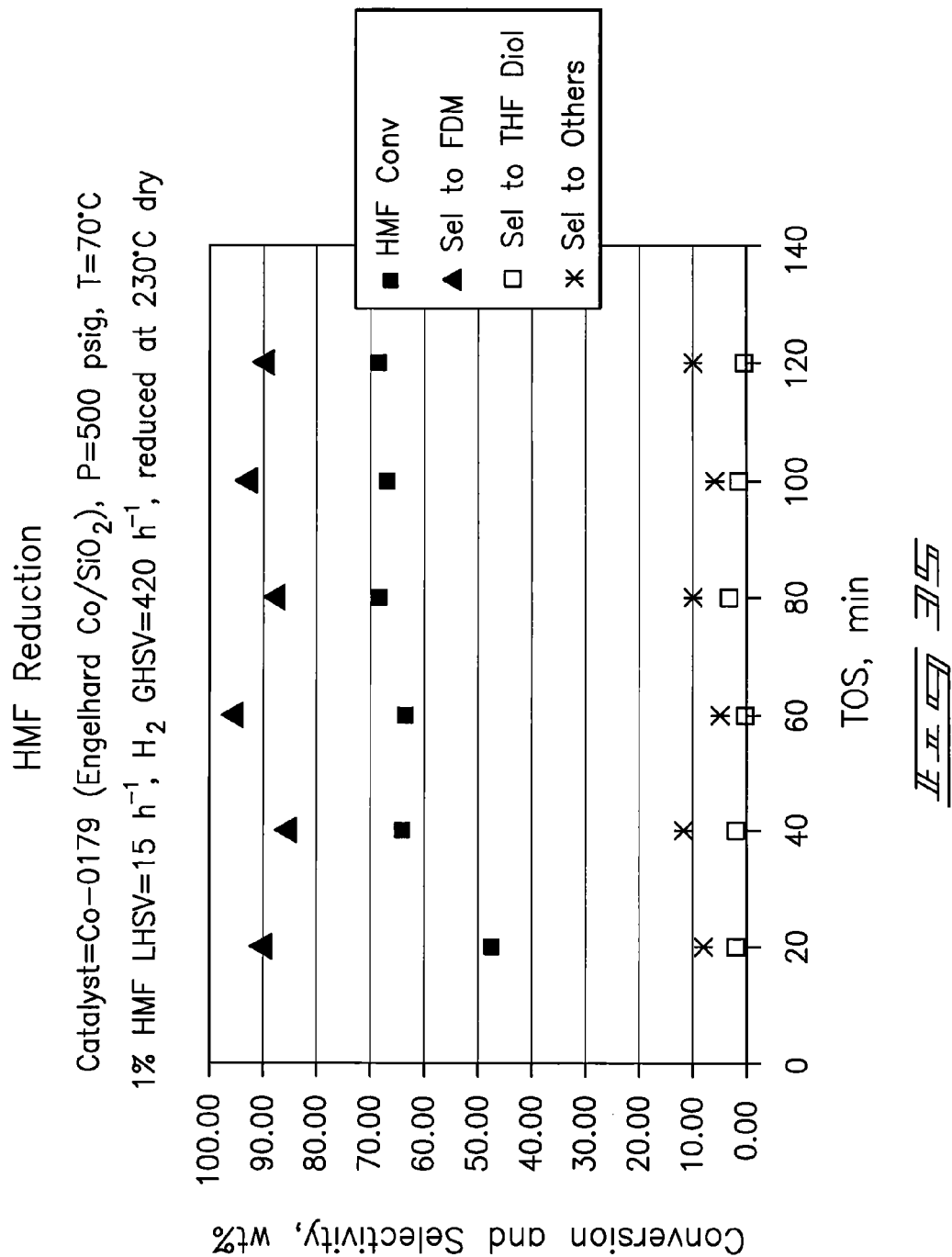
FIG. 35 shows HMF conversion and product selectivity as a function of time on stream for the catalyst of FIG. 23 reduced at 230° C.
Figure 36:
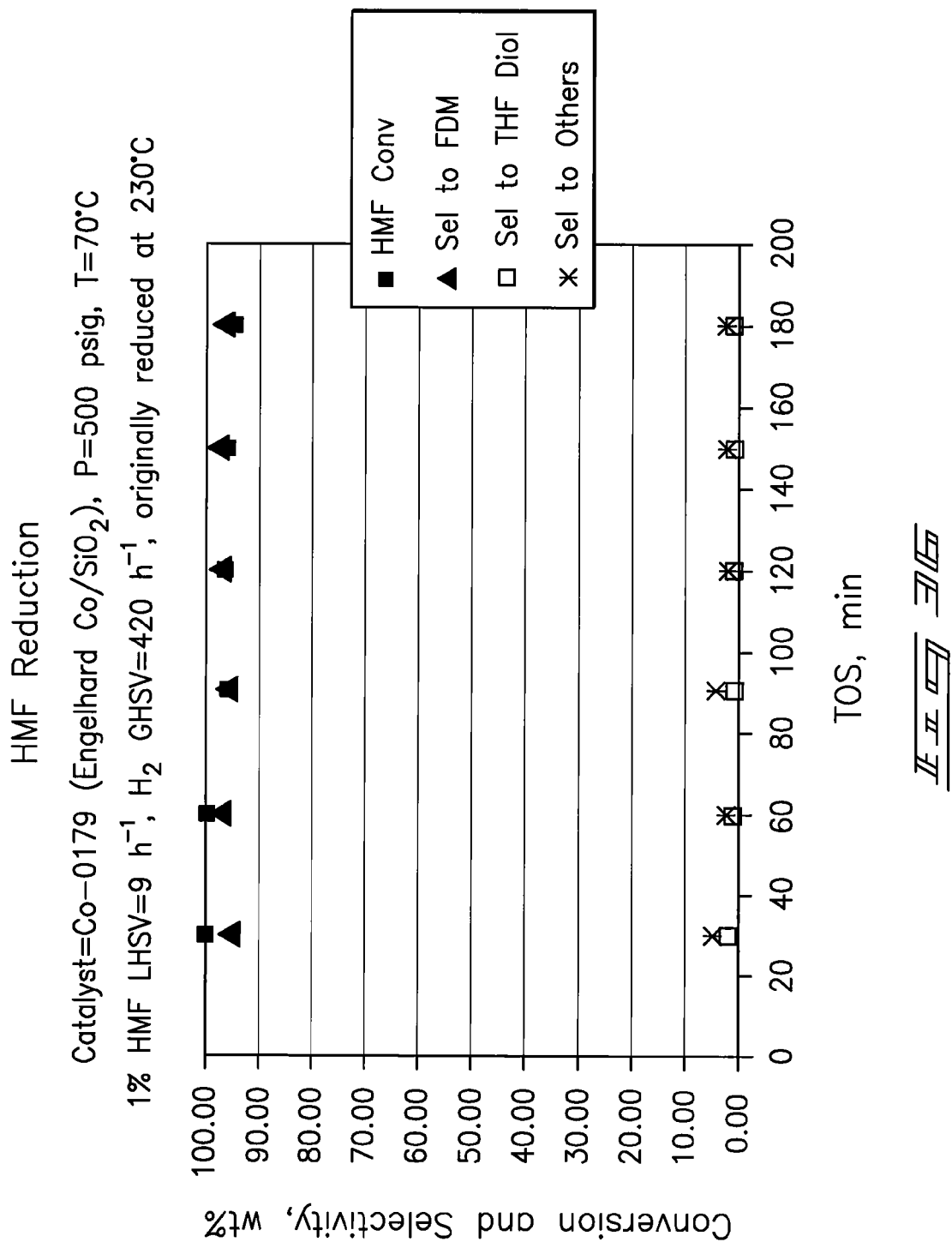
FIG. 36 shows HMF conversion and product selectivity as a function of time on stream for the catalyst of FIG. 23 originally reduced at 230° C. utilizing a decreased LHSV relative to FIG. 23.
Figure 37:
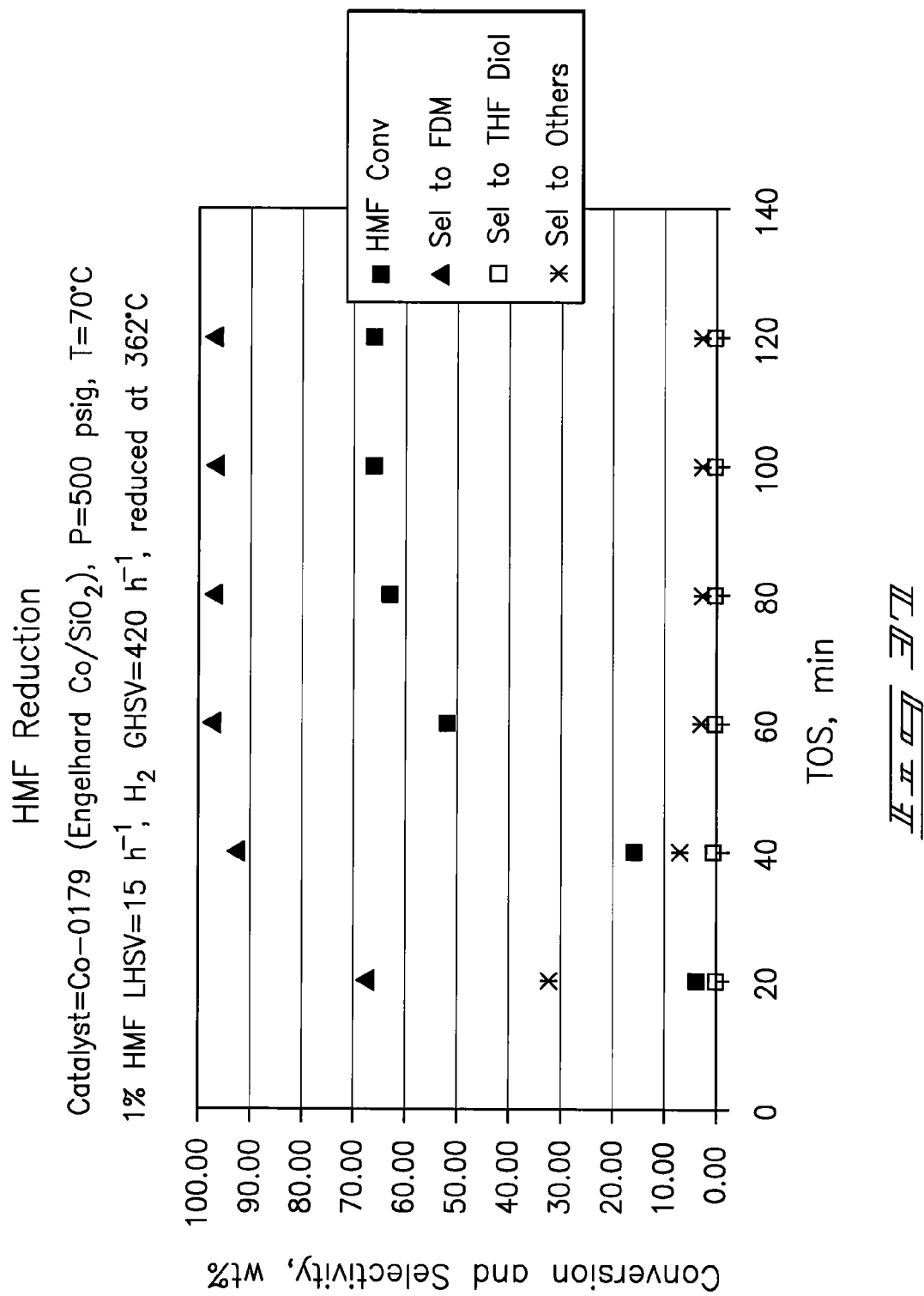
FIG. 37 shows HMF conversion and product selectivity as a function of time on stream for the catalyst of FIG. 23 reduced at a temperature of 362° C.
Figure 38:
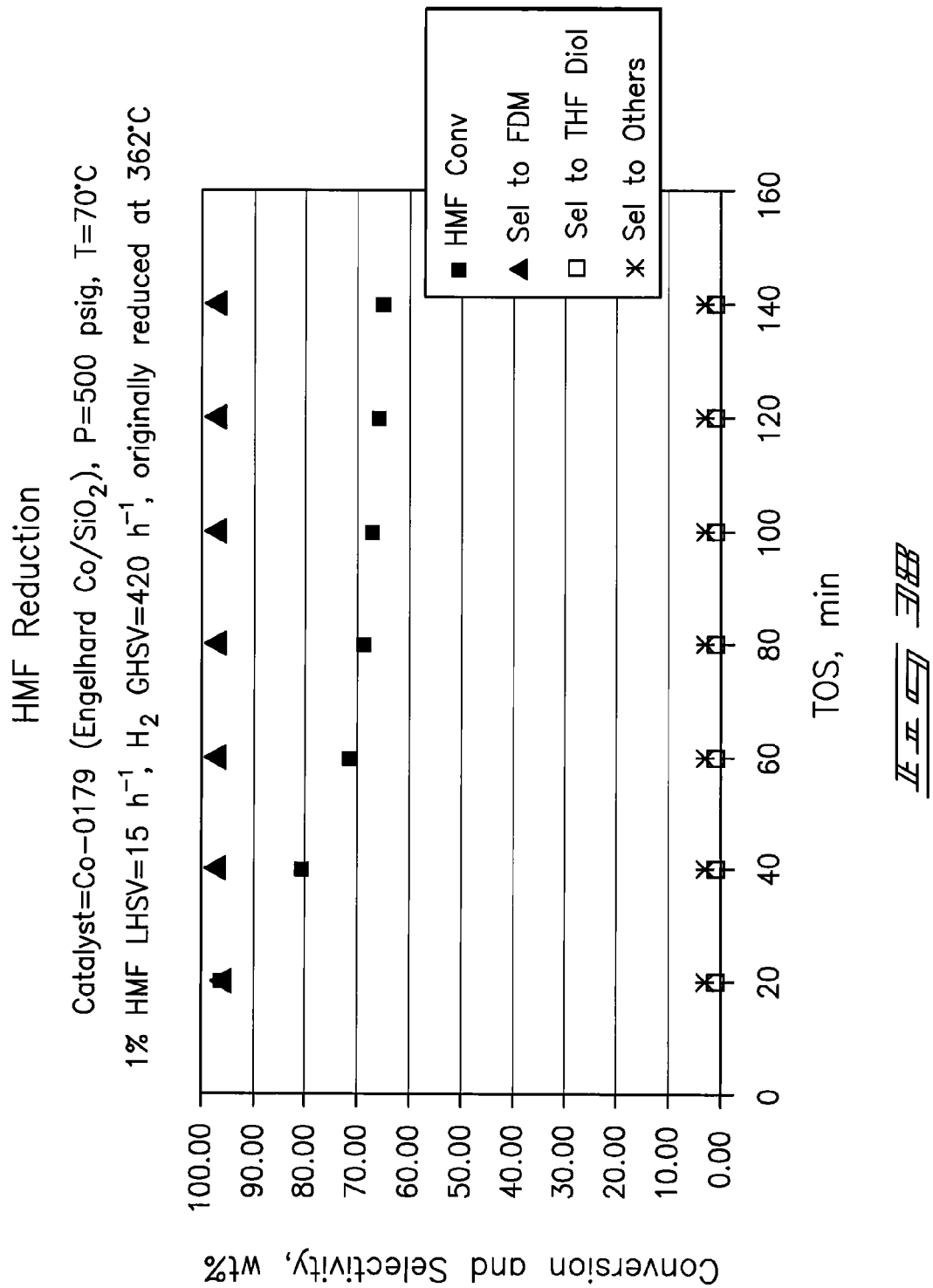
FIG. 38 shows HMF conversion and product selectivity as a function of time on stream for the catalyst of FIG. 23 originally reduced at 362° C.
Figure 39:
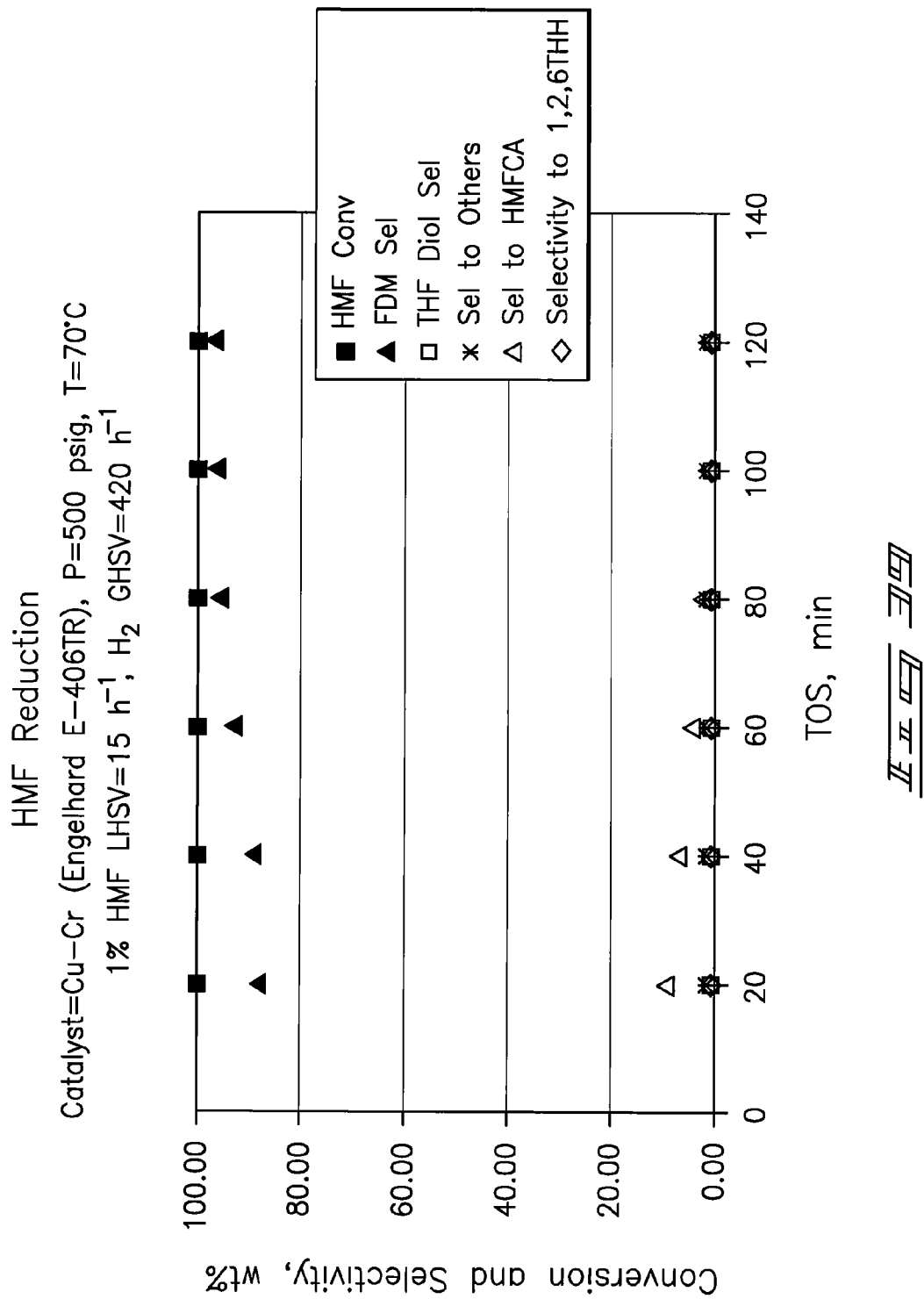
FIG. 39 shows HMF conversion and product selectivity as a function of time on stream utilizing a Cu—Cr catalyst and a base set of reaction parameters in accordance with another aspect of the invention.
Figure 40:
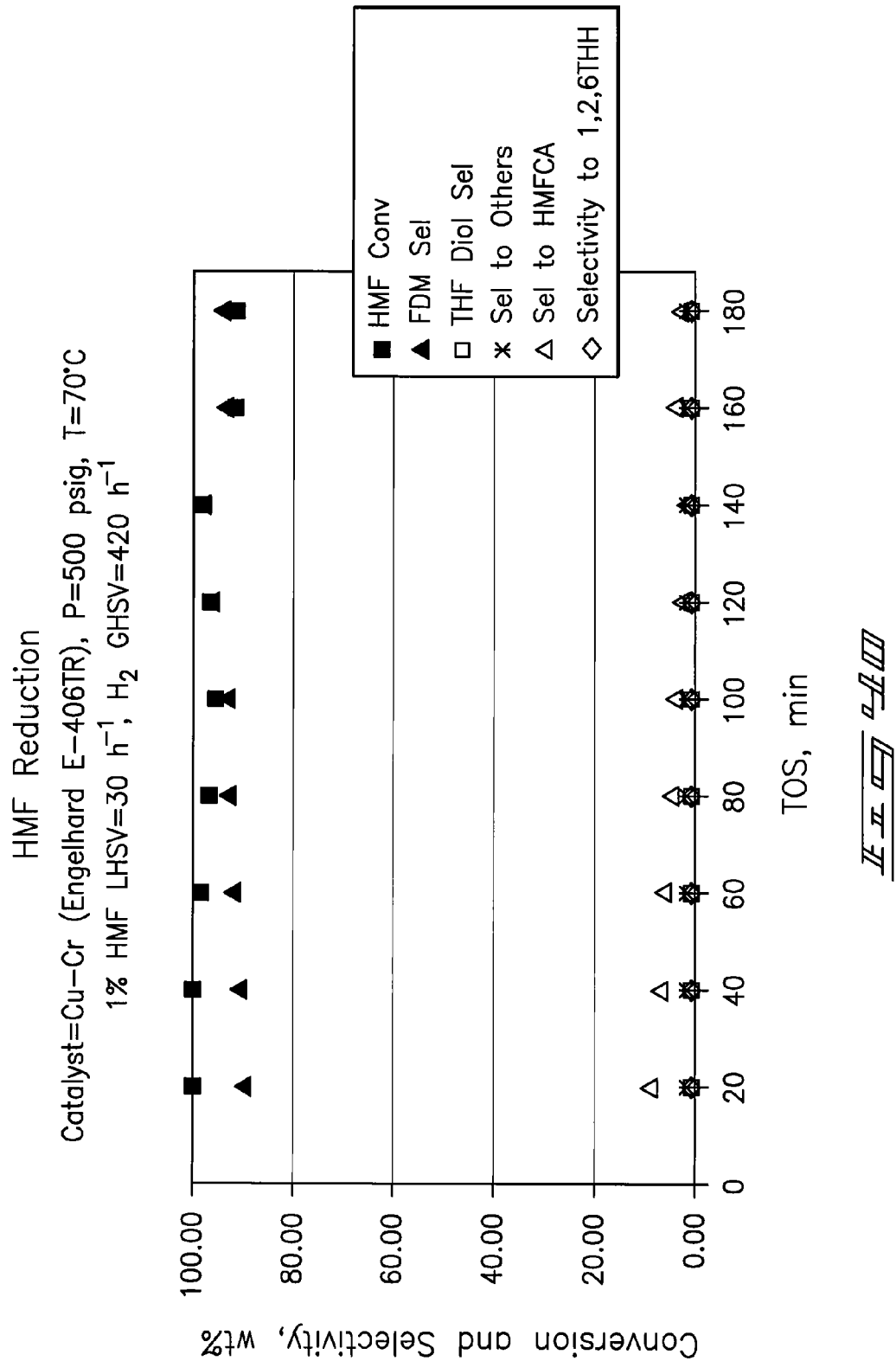
FIG. 40 shows HMF conversion and product selectivity as a function of time on stream utilizing the catalyst of FIG. 39 and an increased LHSV relative to FIG. 39.
Figure 41:
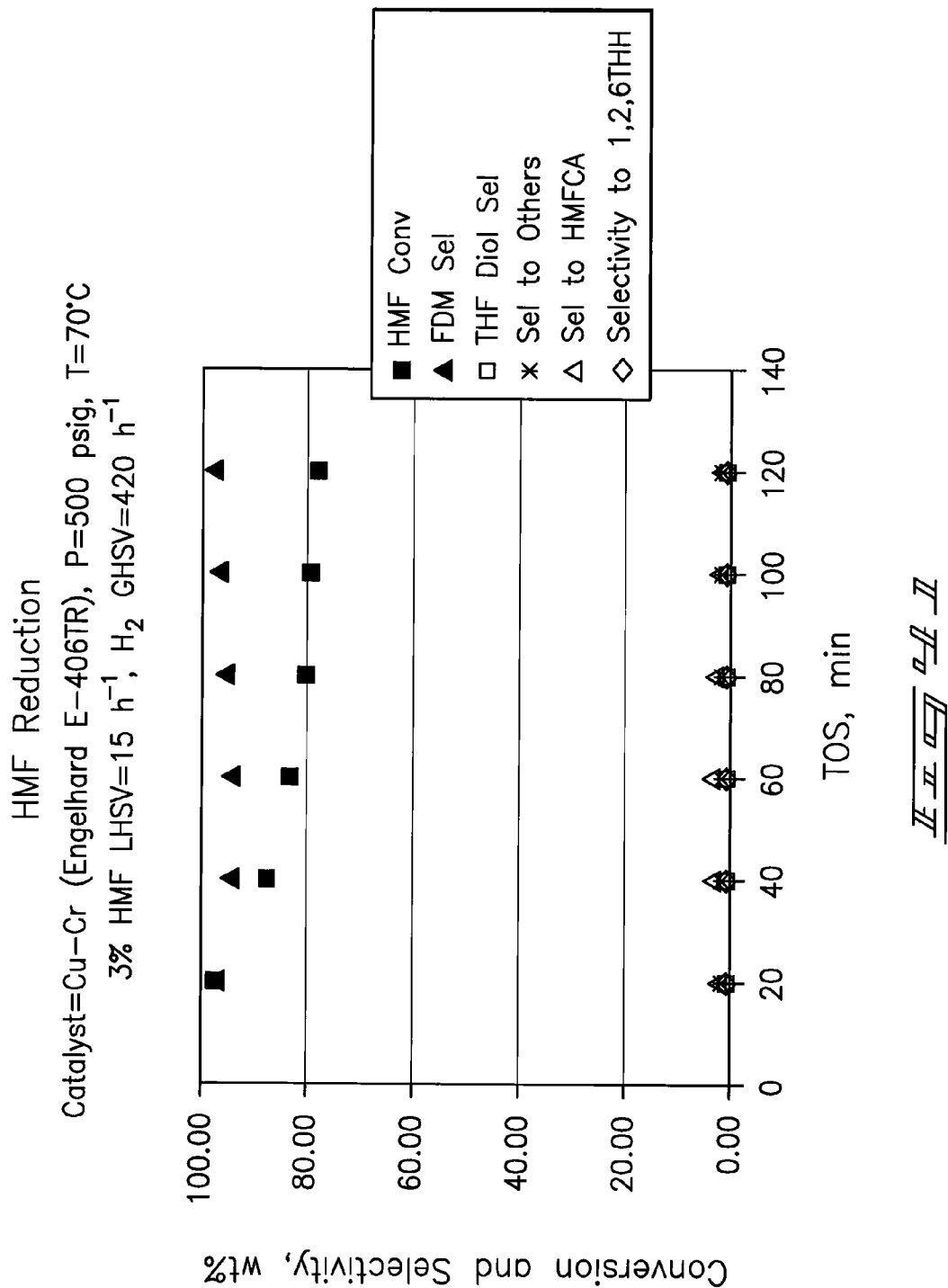
FIG. 41 shows HMF conversion and product selectivity as a function of time on stream for the catalyst of FIG. 39 at an increased HMF feed concentration relative to FIG. 39.
Figure 42:
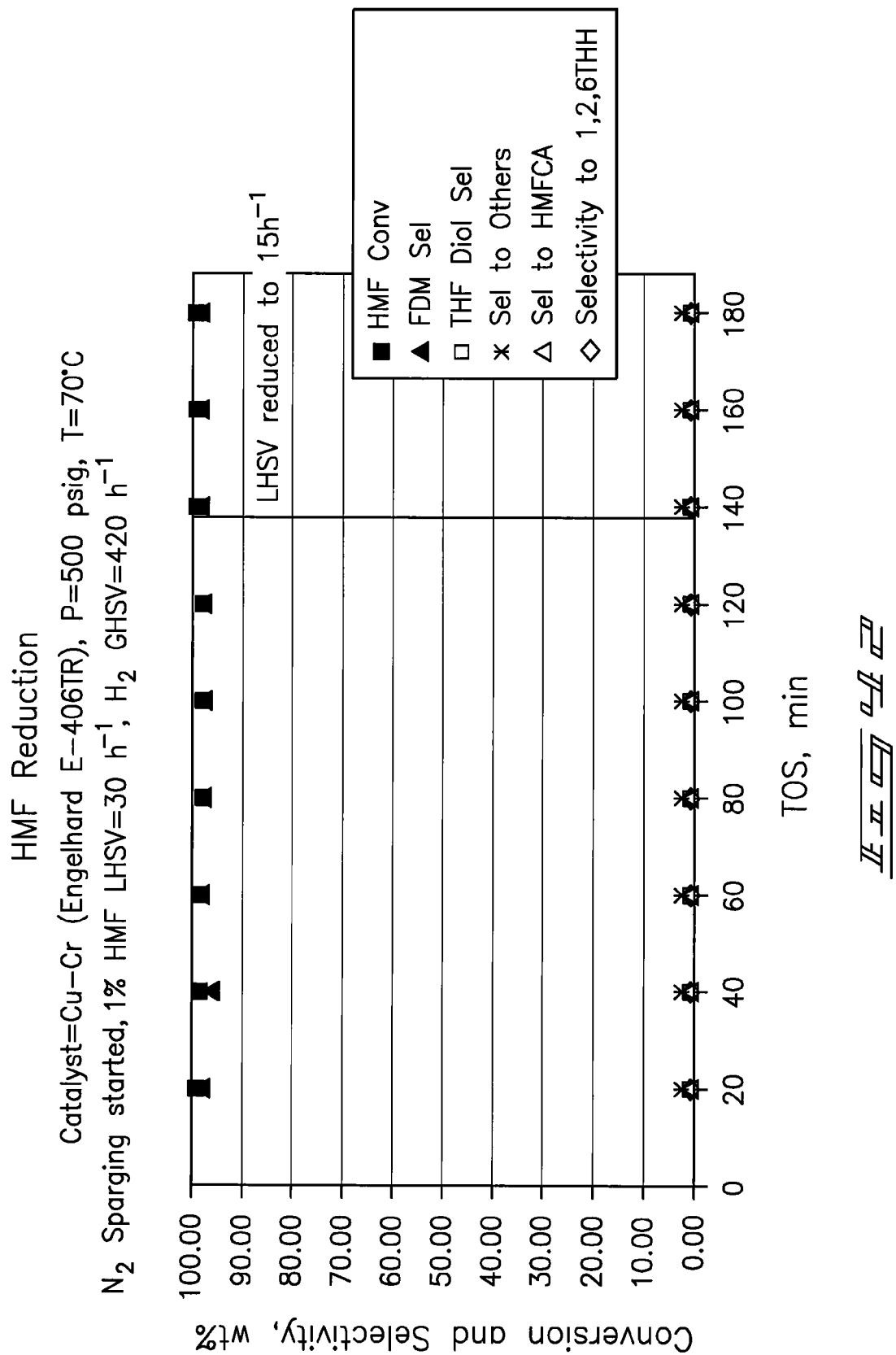
FIG. 42 shows HMF conversion and product selectivity as a function of time on stream for the catalyst of FIG. 39 at an increased LHSV over a portion of the run and $N_2$ sparging.
Figure 43:
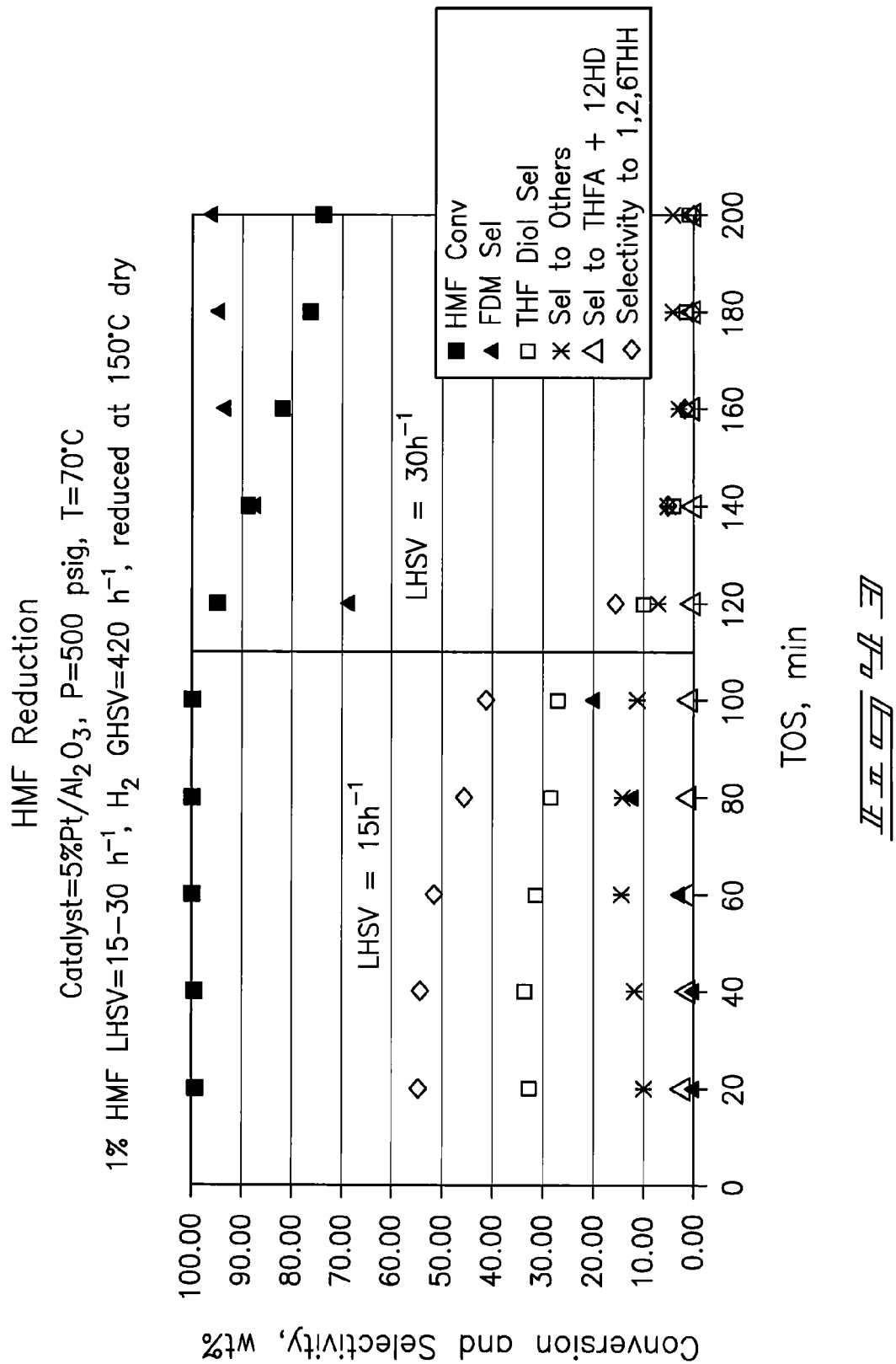
FIG. 43 shows HMF conversion and product selectivity as a function of time on stream for a 5% Pt/$Al_2O_3$ catalyst reduced at 150° C. at a base set of reaction parameters with varied LHSV.
Figure 44:
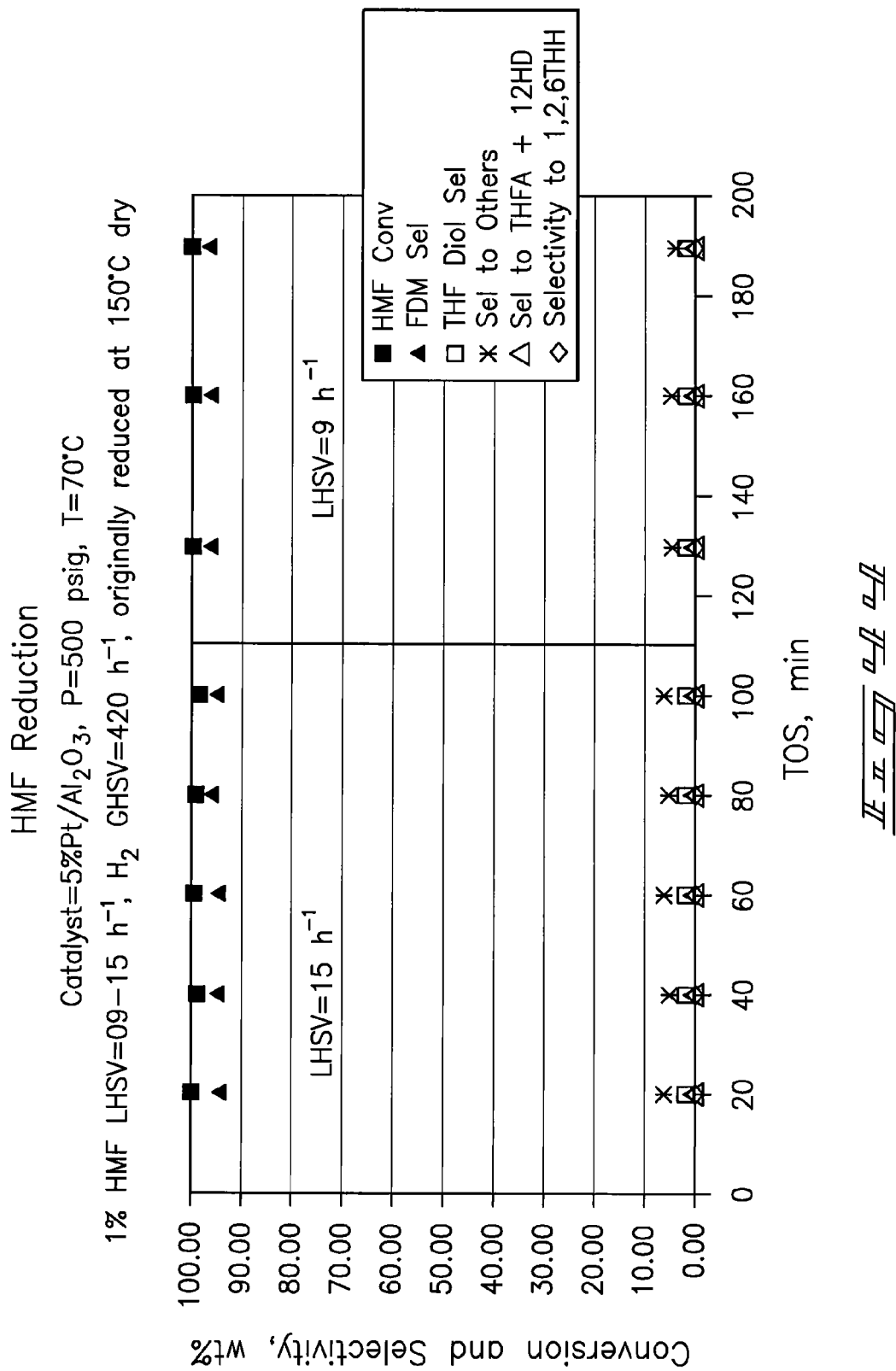
FIG. 44 shows HMF conversion and product selectivity as a function of time on stream for the catalyst of FIG. 43 originally reduced at 150° C. at a decreased LHSV relative to FIG. 43.
Figure 45:
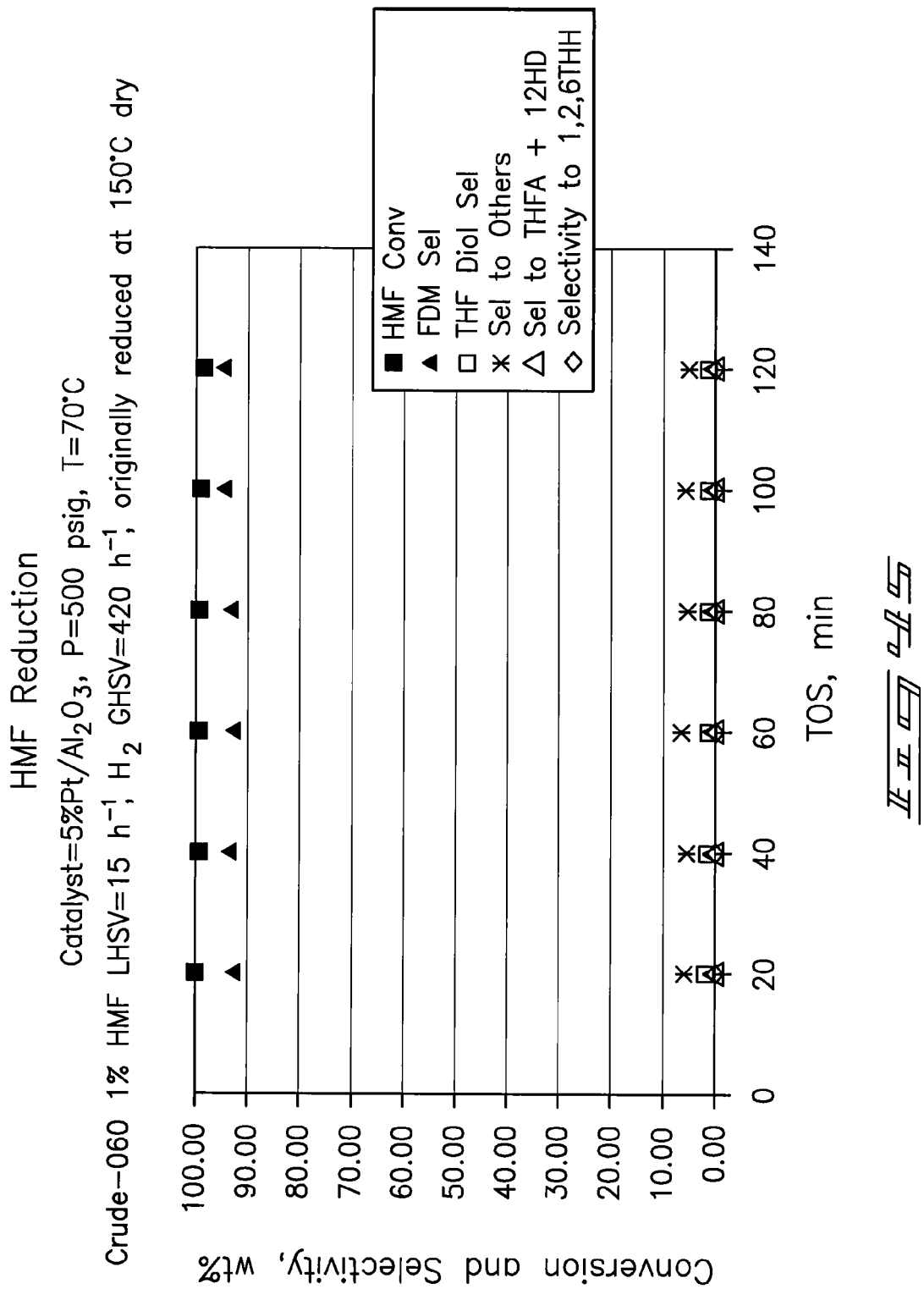
FIG. 45 shows HMF conversion and product selectivity as a function of time on stream utilizing the catalyst of FIG. 43 and a crude HMF feed.
Figure 48B:
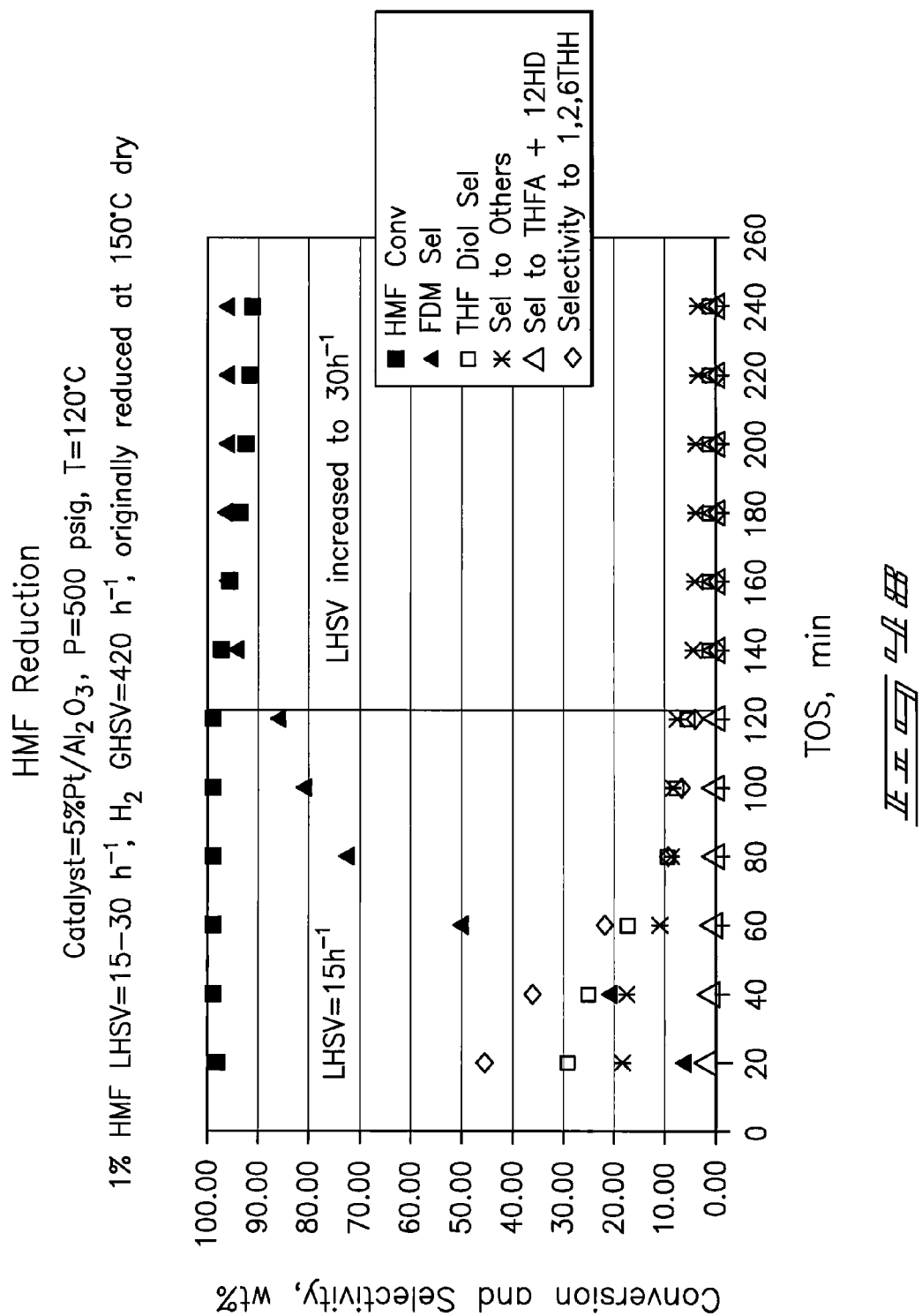
FIG. 48 shows HMF conversion and product selectivity as a function of time on stream utilizing the catalyst of FIG. 43 at an increased reactor temperature relative to FIG. 43.
Figure 52:
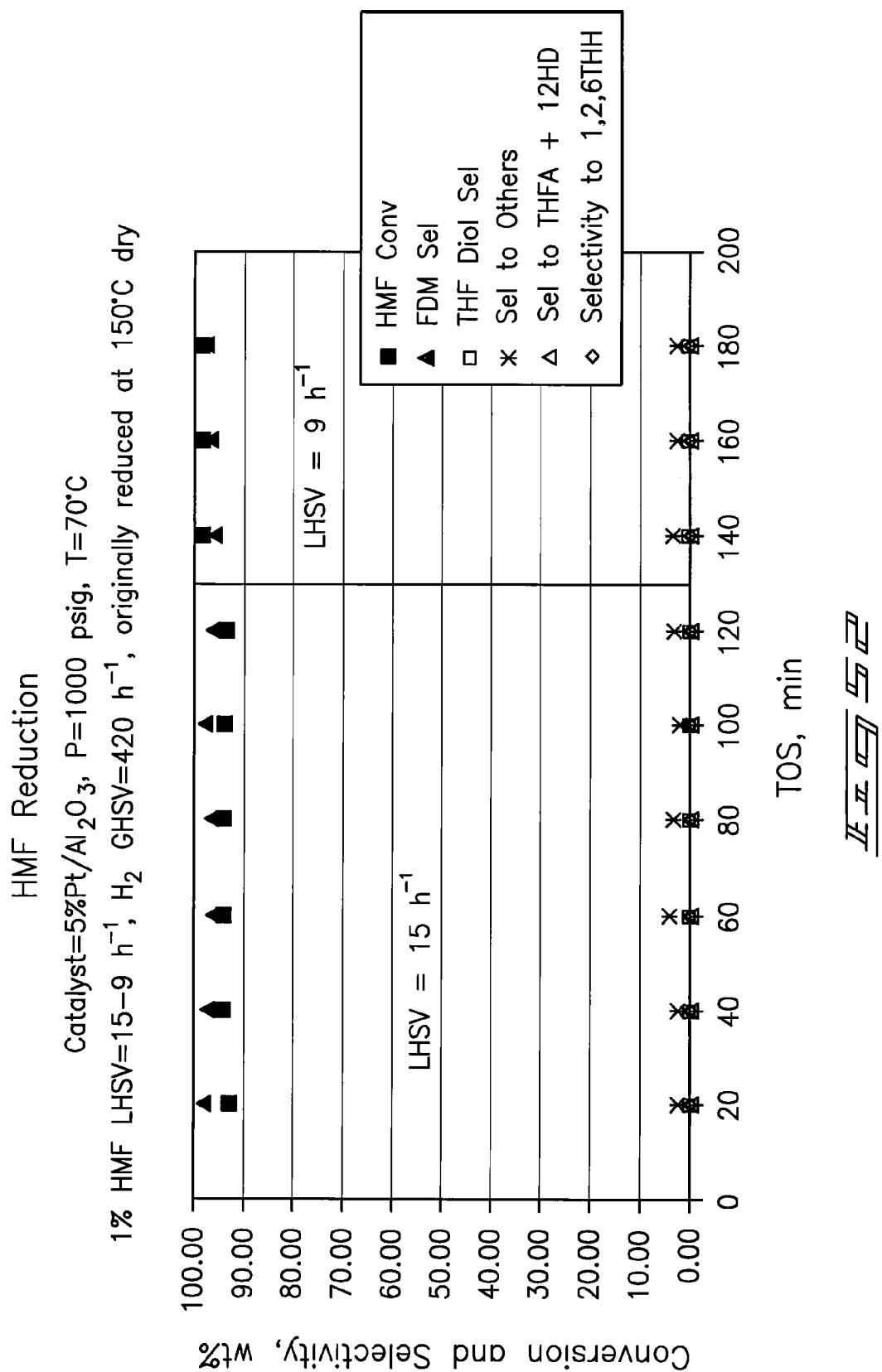
FIG. 52 shows HMF conversion and product selectivity as a function of time on stream for the catalyst of FIG. 43 at an increased pressure and decreased LHSV relative to FIG. 43.
Figure 53:
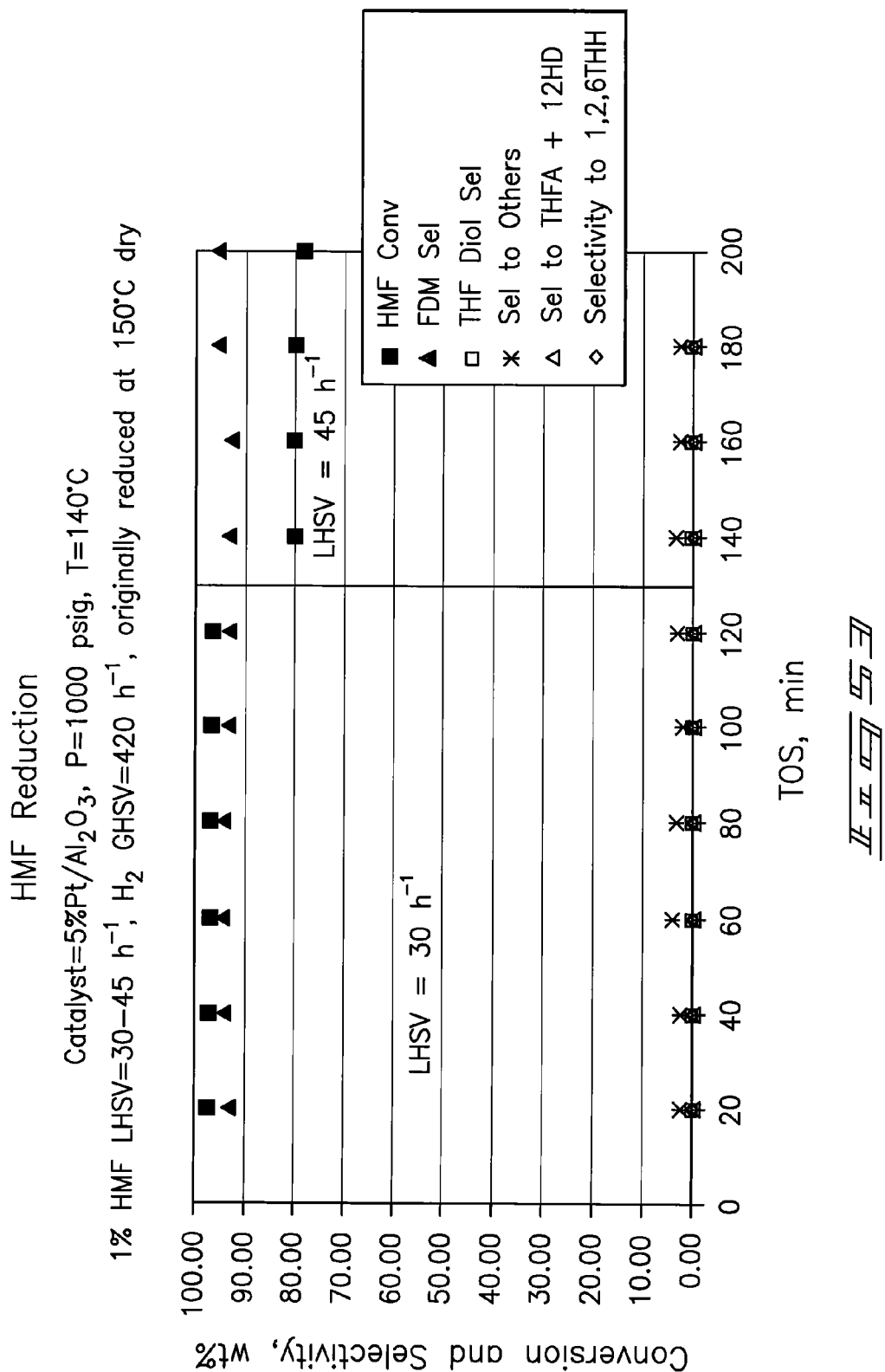
FIG. 53 shows HMF conversion and product selectivity as a function of time on stream for the catalyst of FIG. 43 at an increased pressure, an increased temperature and at an increased LHSV relative to FIG. 43.
Figure 54:
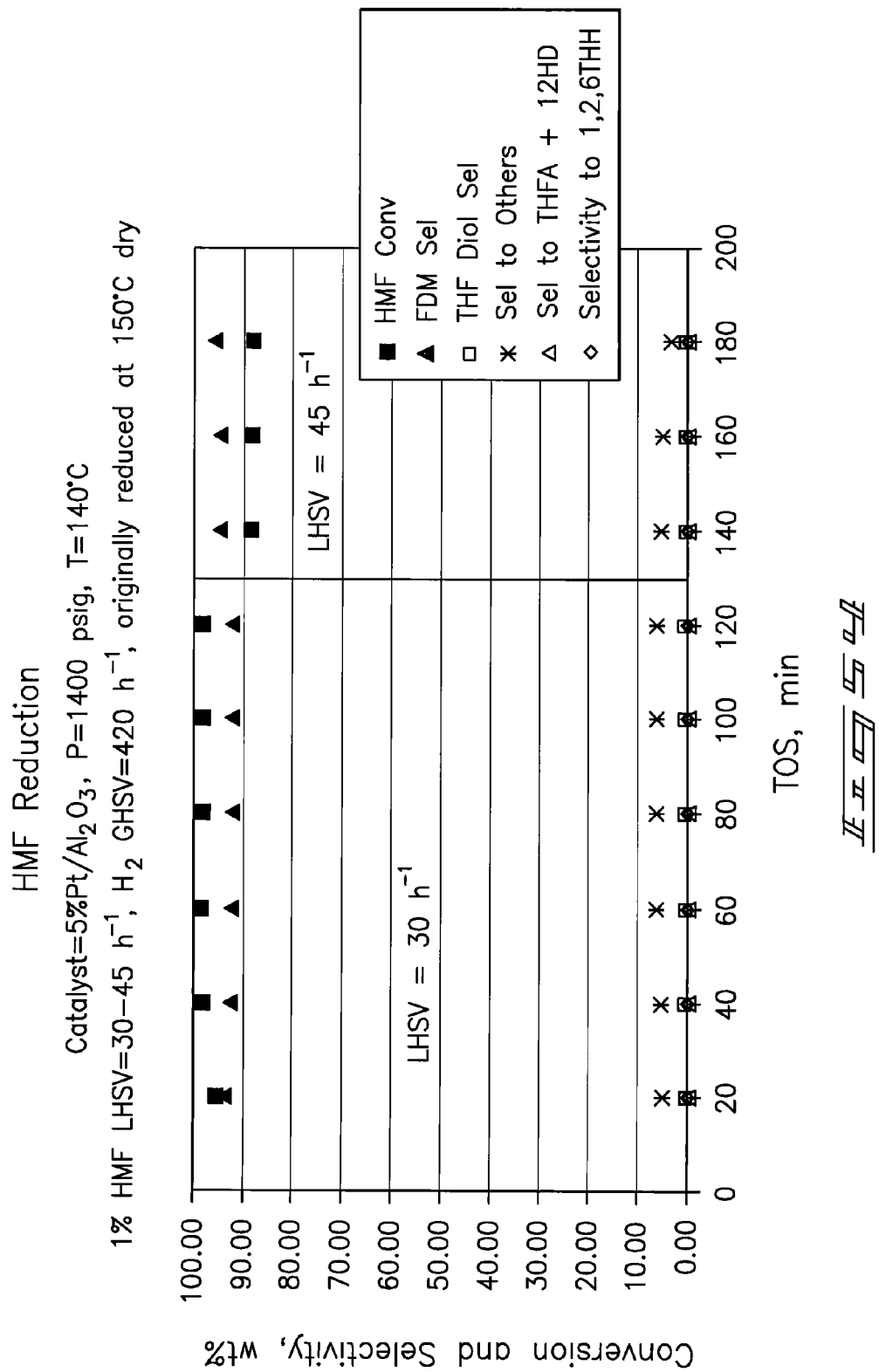
FIG. 54 shows HMF conversion and product selectivity as a function of time on stream for the catalyst of FIG. 43 at an increased pressure, an increased temperature and at an increased LHSV relative to FIG. 43.
Figure 55:
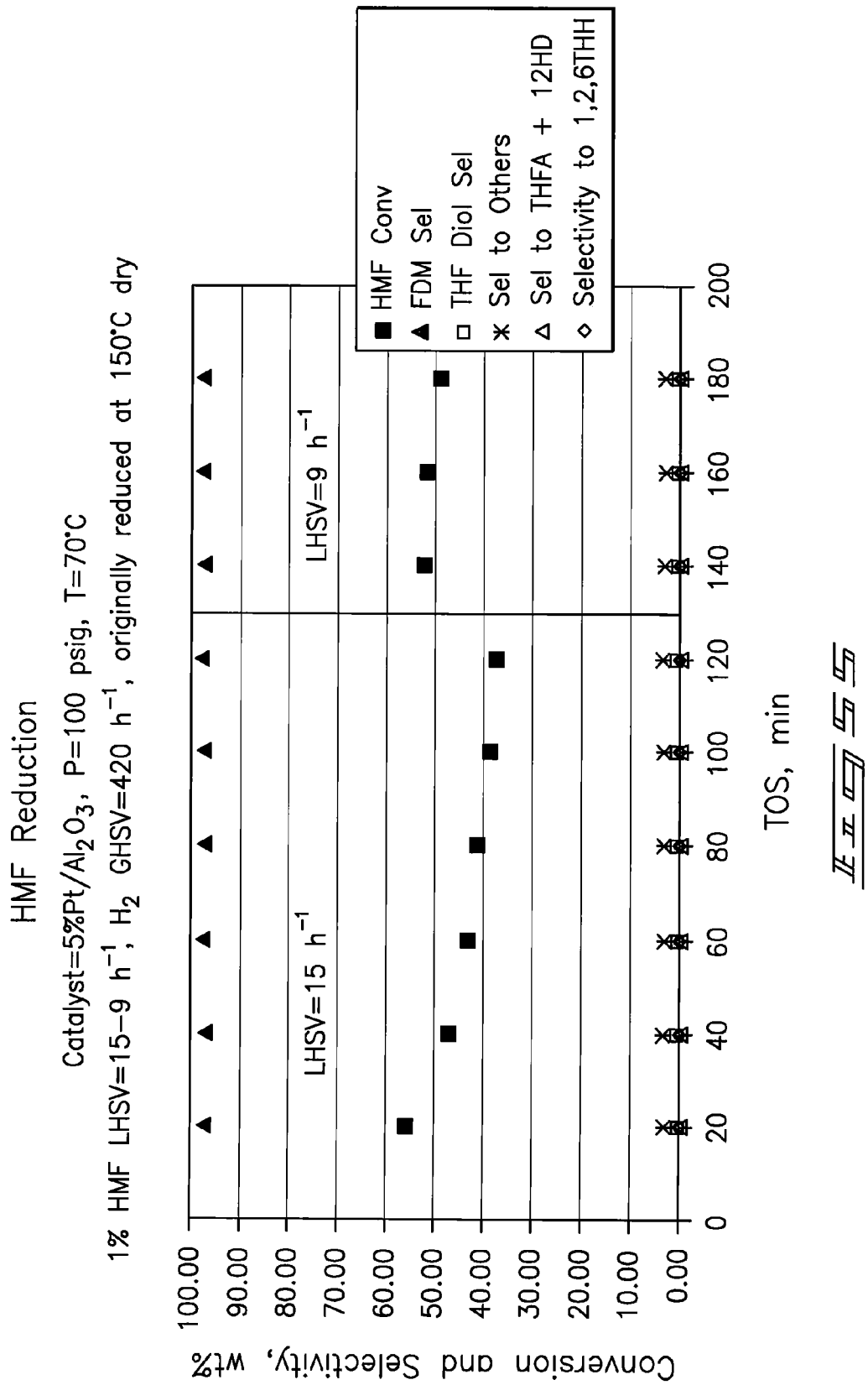
FIG. 55 shows HMF conversion and product selectivity as a function of time on stream for the catalyst of FIG. 43 at a decreased pressure and decreased LHSV relative to FIG. 43.
Figure 56:
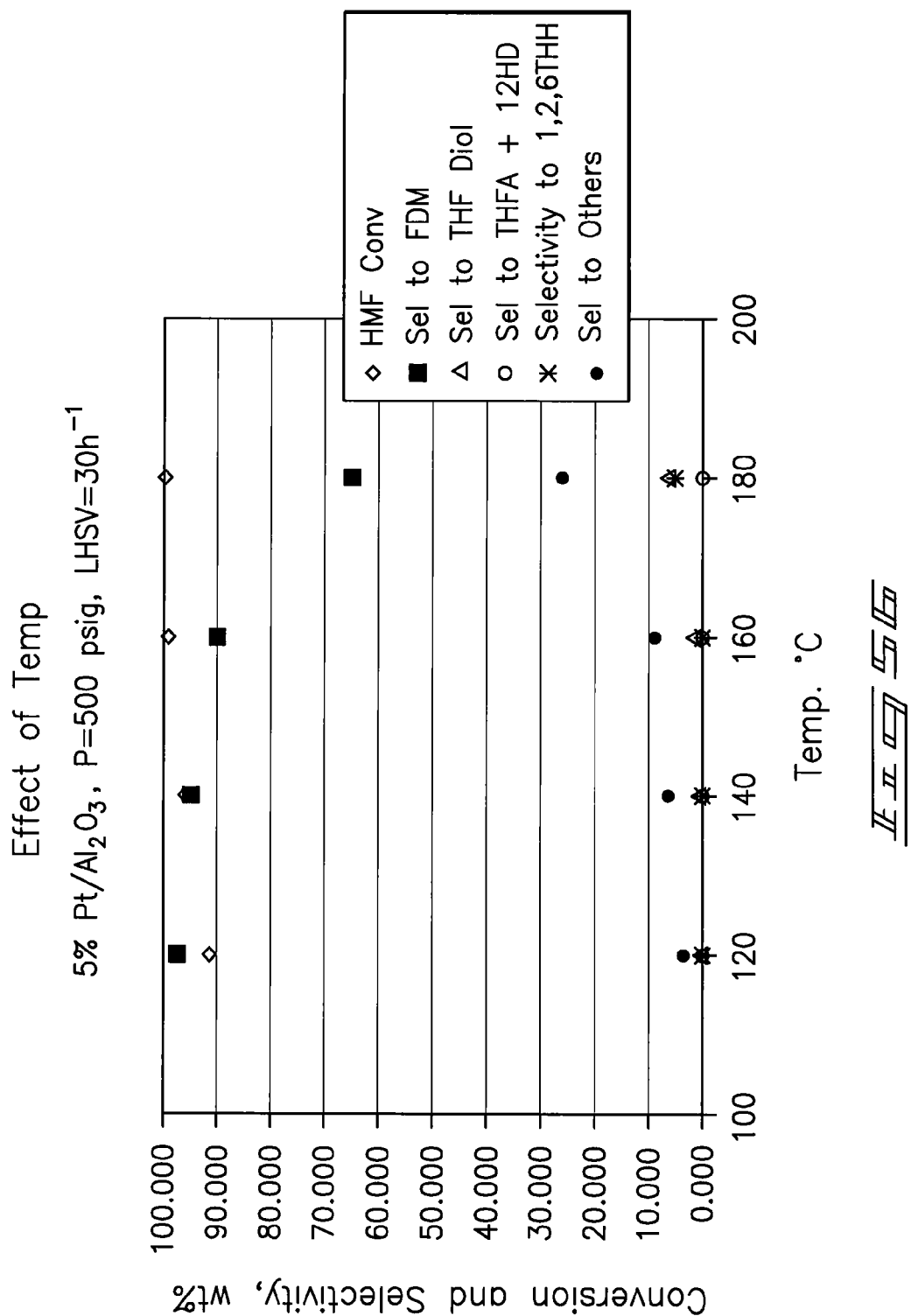
FIG. 56 shows HMF conversion and product selectivity as a function of temperature for the catalyst of FIG. 43.

Additional flow reactor studies were conducted utilizing alternative catalysts. Presented herewith are results of flow reactor studies conducted utilizing Pt/SiO$_2$ (FIG. 22), an alternative Co/SiO$_2$ catalyst (FIGS. 23-38), a copper-chromite catalyst (FIGS. 39-42), or Pt/Al$_2$O$_3$ (FIGS. 43-56). The enclosed sets of results for the alternative Co/SiO$_2$ catalyst, Cu-chromite, and Pt/Al$_2$O$_3$ include effects on conversion and product selectivity of varied reaction parameters including gas and liquid flow rates, HMF feed concentration, H$_2$ pressure, and/or temperature. Table 5 shows the effect of pretreatment temperature for the alternative Co/SiO$_2$ catalyst (Engelhard Co-0179). Table 6 shows the effect of pressure for continuous flow reaction utilizing the Pt/Al$_2$O$_3$ catalyst.

TABLE 5

Effect of Catalyst Pretreatment Temperature

|  | Condition # | | |
|---|---|---|---|
|  | 1 | 13 | 9 |
| Reaction Temp,° C. | 362 | 230 | 150 |
| Con Conv, % | 99.9 | 66.9 | 84.3 |
| FDM Sel | 68.7 | 93.2 | 88.3 |
| THF Diol Sel | 29.5 | 1.0 | 4.0 |
| Others Sel | 1.7 | 5.8 | 7.7 |

TABLE 6

Effect of Pressure (5% Pt/Al$_2$O$_3$)

|  | 70° C., LHSV = 15 h$^{-1}$ | | 140° C., LHSV = 30 h$^{-1}$ | | |
|---|---|---|---|---|---|
|  | P = 500 psig | P = 1000 psig | P = 500 psig | P = 1000 psig | P = 1400 psig |
| HMF Conv, wt % | 91.63 | 93.68 | 96.21 | 96.66 | 98.46 |
| Sel to FDM, wt % | 95.10 | 96.06 | 94.22 | 93.33 | 92.82 |
| Sel to THF Diol | 0.49 | 0.10 | 0.53 | 0.73 | 1.14 |
| Sel to Others | 4.41 | 3.84 | 5.25 | 5.93 | 6.04 |

EXAMPLE 4

Reduction of HMF with Production of FDM in a Fixed-Bed Continuous Flow Reactor

A tubular reactor made of ⅜ inch stainless-steel thick-wall tubing (0.065 inch wall thickness) was utilized. 2 mL (1.11 g) of dry Pt/Al$_2$O$_3$ catalyst (prepared with 5% Pt on 40-80 mesh alumina support) was reduced before testing at 150° C. at atmospheric pressure with a hydrogen flow of 20 mL/minute. The reactor was then cooled to 40° C. and water was introduced at a flow rate of 0.5 mL/min with a high pressure liquid pump.

The hydrogen gas flow was increased to approximately 120 mL/minute until the system pressure increased to 500 psig, at which time the hydrogen flow rate was decreased to 14 mL/minute. The temperature operating set point of the system was increased to 70° C. and upon achieving 70° C., a 1% feed solution of HMF (optionally purged with nitrogen) was fed to the catalyst bed at a rate of 0.5 mL/minute. At 20 minute reaction time intervals (measured from the time feed was started) liquid samples of the product exiting the reactor were collected for LC analysis. LC results for each sample taken showed 100% conversion of HMF and 95% selectivity to FDM.

After 1 hour and 40 minutes of testing the liquid feed rate of the 1% HMF solution was decreased to 0.3 mL/minute. Sampling and analysis was repeated at 20 minute intervals for an additional 1 hour and 40 min. The results indicate no observed over-reduction at this lower liquid flow rate (as apparent by the absence of THF dimethanol) and that HMF conversion remained at 100% with 95% selectivity to FDM.

As can be observed in the forgoing figures, under certain conditions products other than FDM can be selectively produced from HMF with particular catalysts. Further studies sere conducted to selectively produce non-FDM products utilizing HMF, FDM or tetrahydrofuran dimethanol (THFDM, THF diol) starting material.

Figure 57:
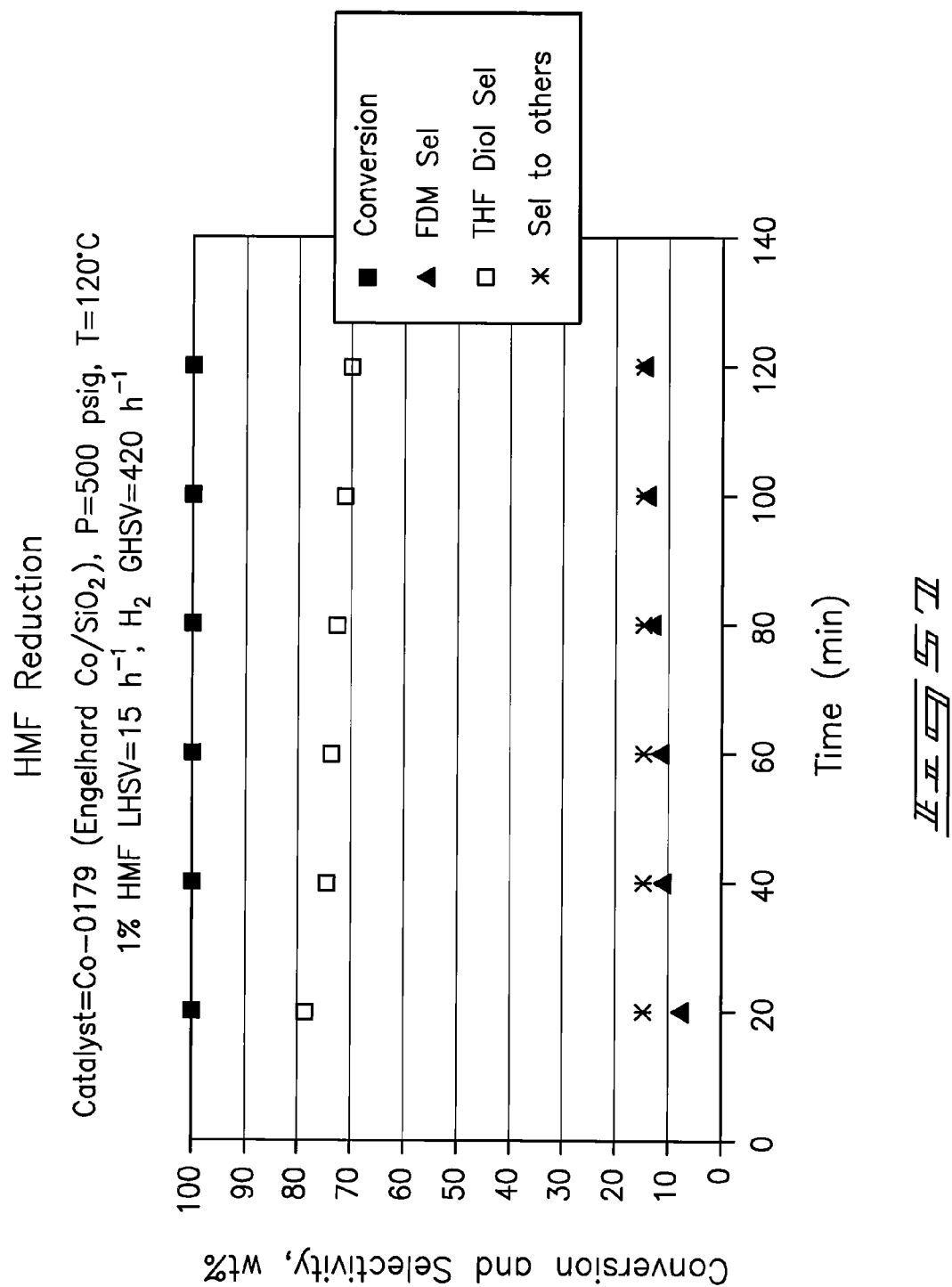
FIG. 57 shows HMF conversion and product selectivity as a function of time on stream utilizing a continuous flow reactor and a Co/$SiO_2$ catalyst at 120° C.

The Co-179 catalyst in a continuous flow reactor at 70° C. resulted in high selectivity (>95%) to FDM (see FIGS. 28, 29 and 36), with only moderate selectivities to THFDM when the temperature is raised to 120° C. Referring to FIG. 57, at about 100% HMF conversion at 120° C. a THFDM selectivity of about 70% was achieved. Reduction to THFDM was incomplete and significant by-products were observed at the higher temperature.

Figure 58:
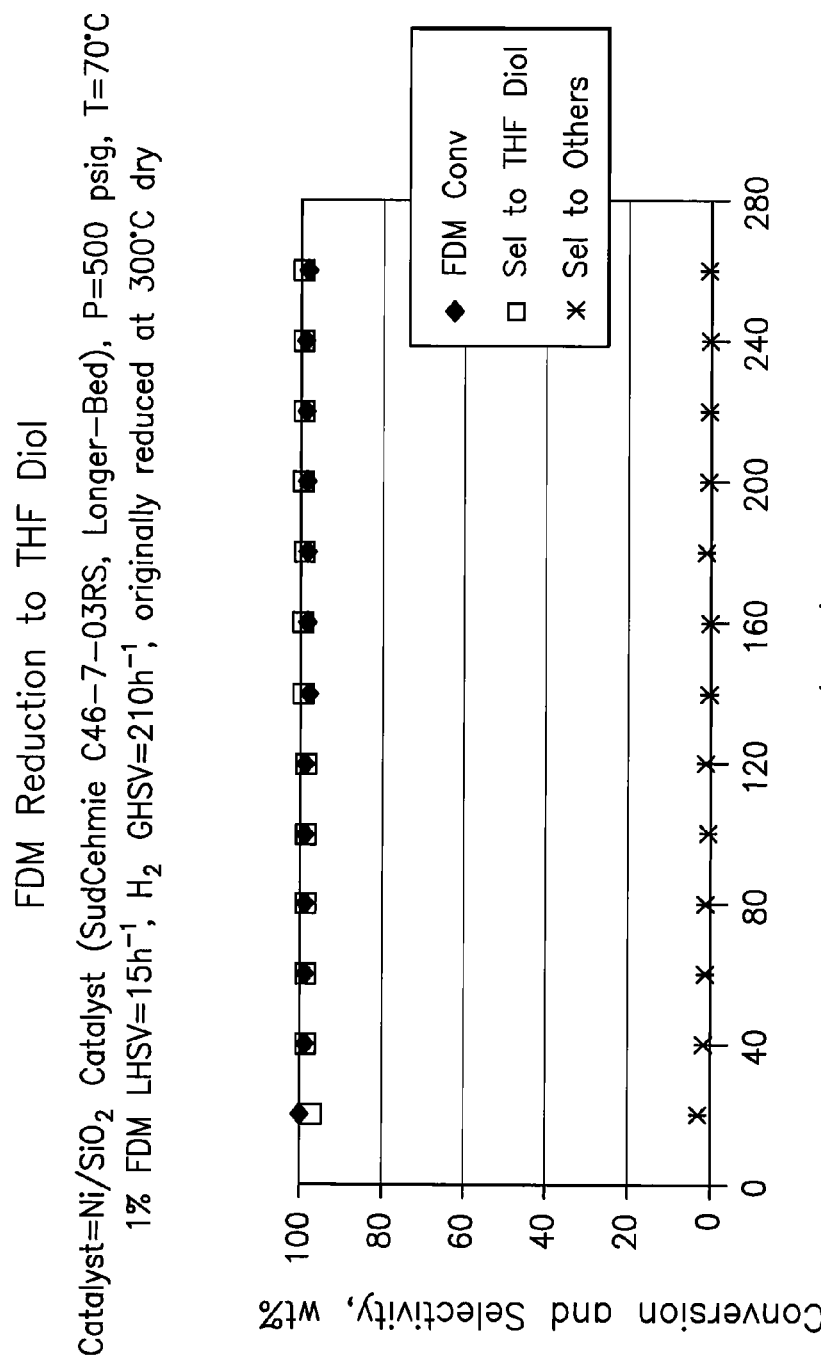
FIG. 58 shows FDM conversion and product selectivity as a function of time on stream for a continuous flow reactor utilizing a Ni/SiO$_2$ catalyst at 70° C.
Figure 59:
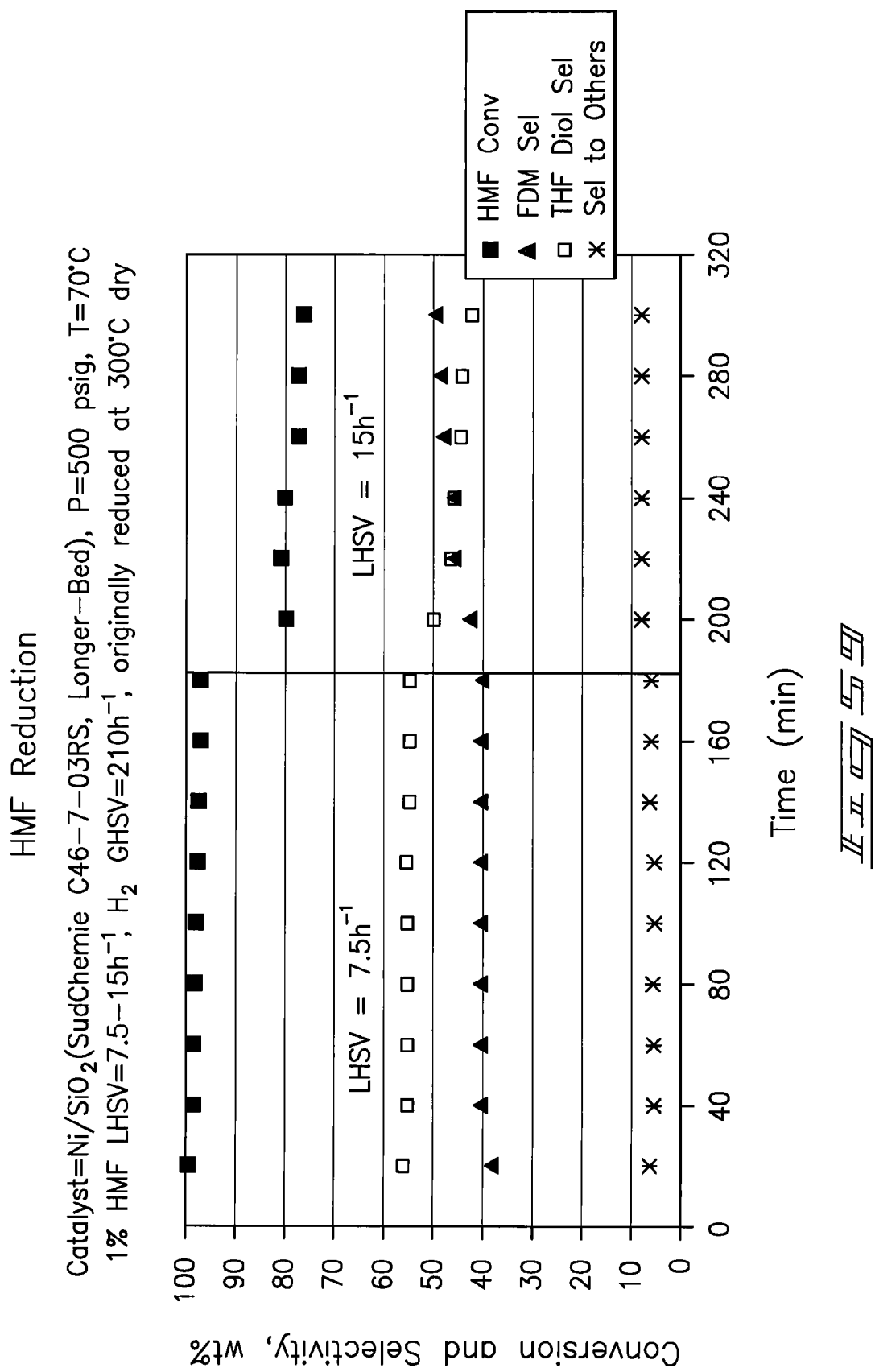
FIG. 59 shows HMF conversion and product selectivity as a function of time on stream for a continuous flow reactor utilizing a Ni/SiO$_2$ catalyst at 70° C. at varied LHSV.
Figure 60:
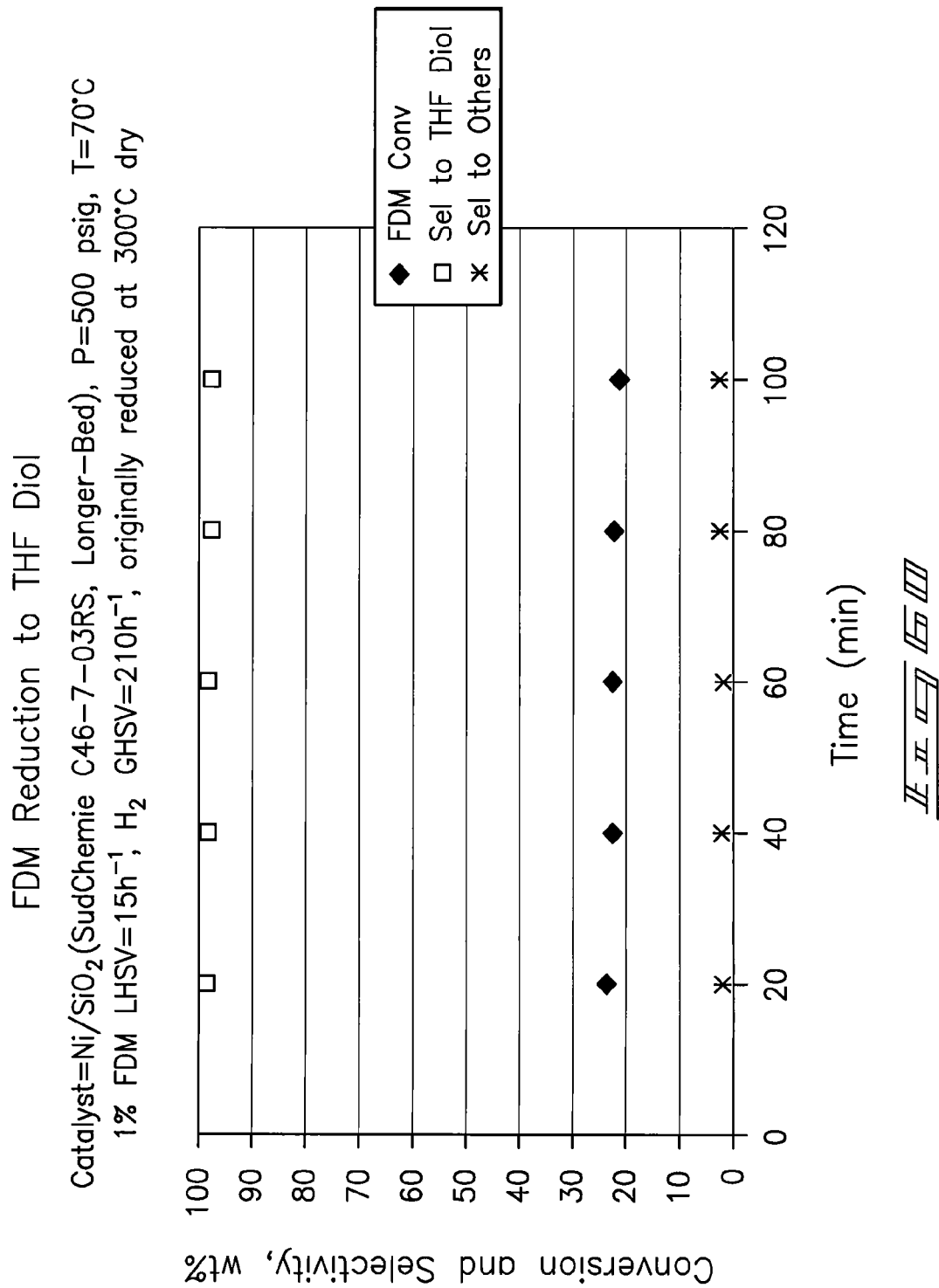
FIG. 60 shows a repeat of FDM conversion and product selectivity as a function of time on stream for a continuous flow reactor utilizing a Ni/SiO$_2$ catalyst at 70° C., after the run shown in FIG. 59.
Figure 62:
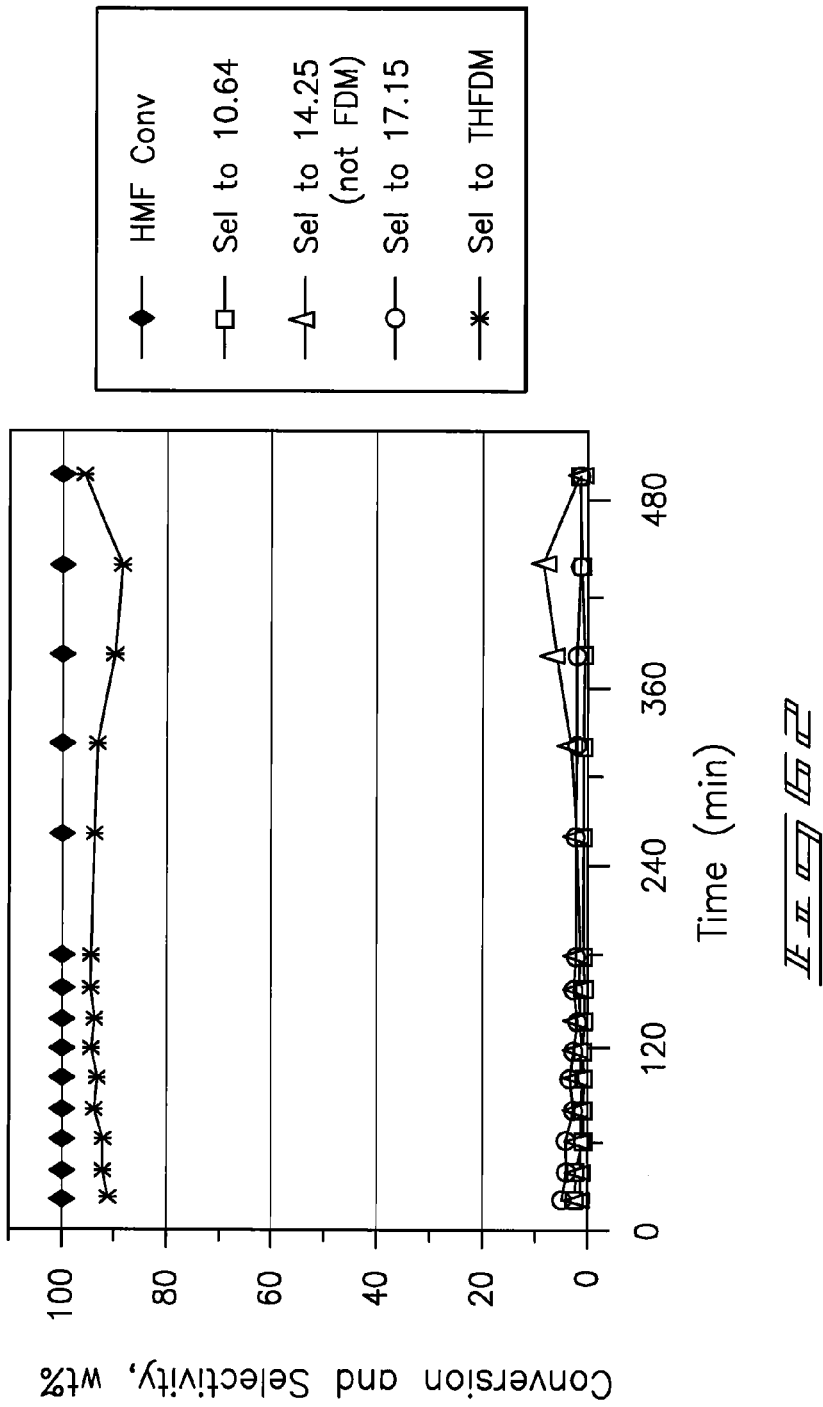
FIG. 62 shows HMF conversion as a function of time on stream for a staged bed continuous flow reactor utilizing segregated Co/SiO$_2$ and Ni/SiO$_2$ catalysts and a base set of reaction conditions in accordance with one aspect of the invention.
Figure 63:
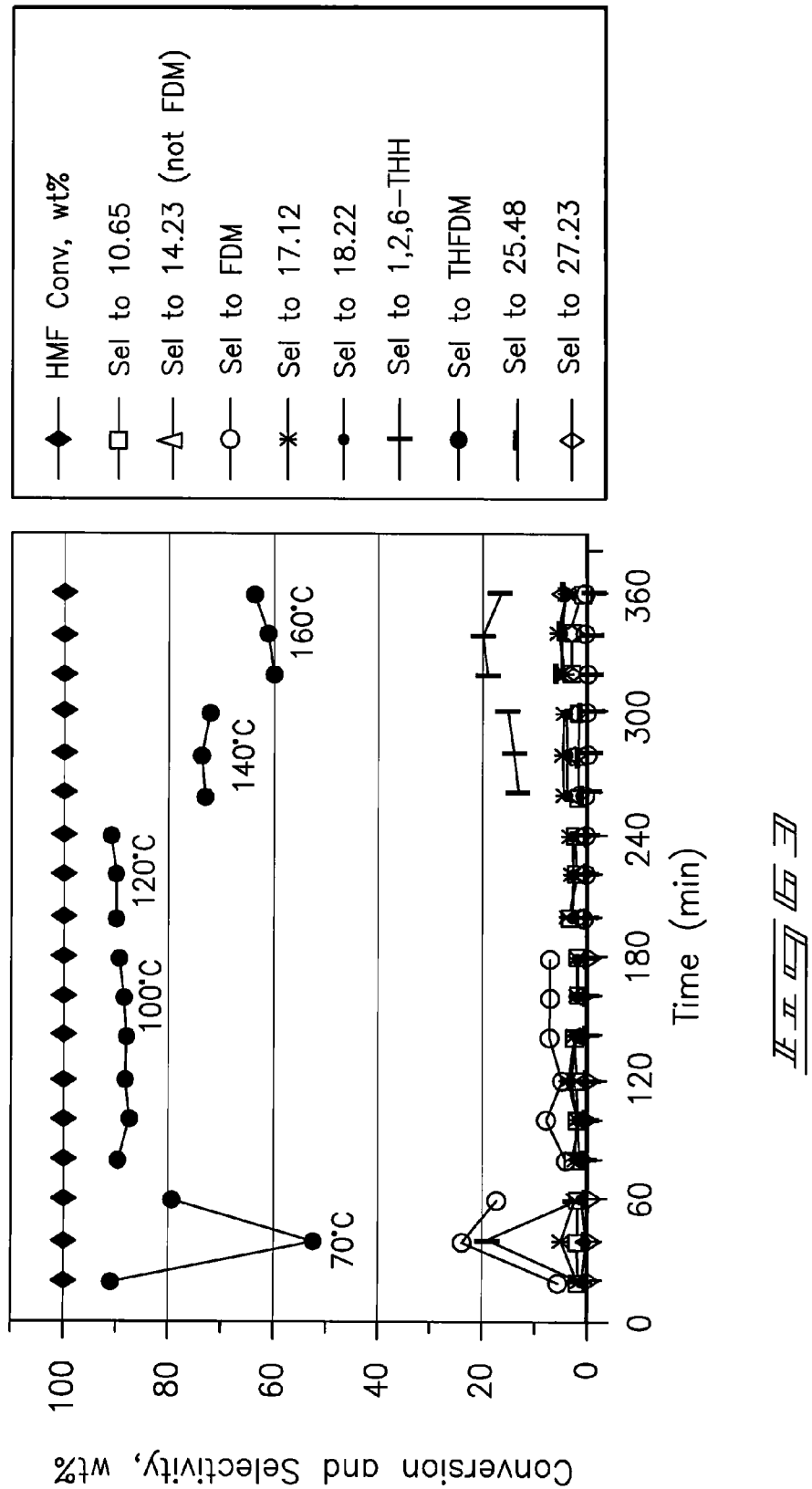
FIG. 63 shows HMF conversion as a function of time on stream utilizing the system of FIG. 62 and increased temperatures relative to FIG. 62.
Figure 64:
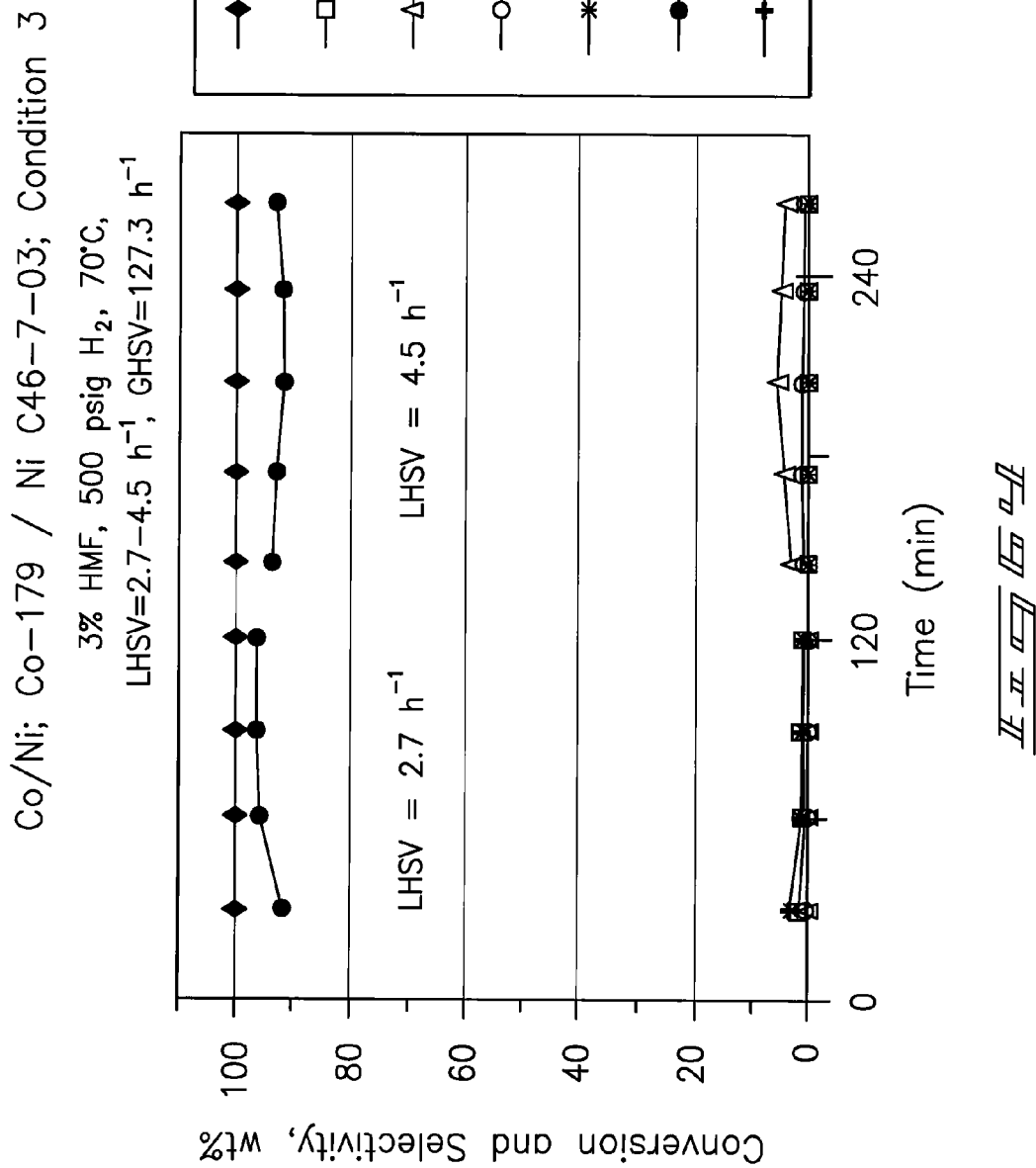
FIG. 64 shows HMF conversion as a function of time on stream utilizing the system of FIG. 62 and increased feed concentration and increased LHSV relative to FIG. 62.
Figure 65:
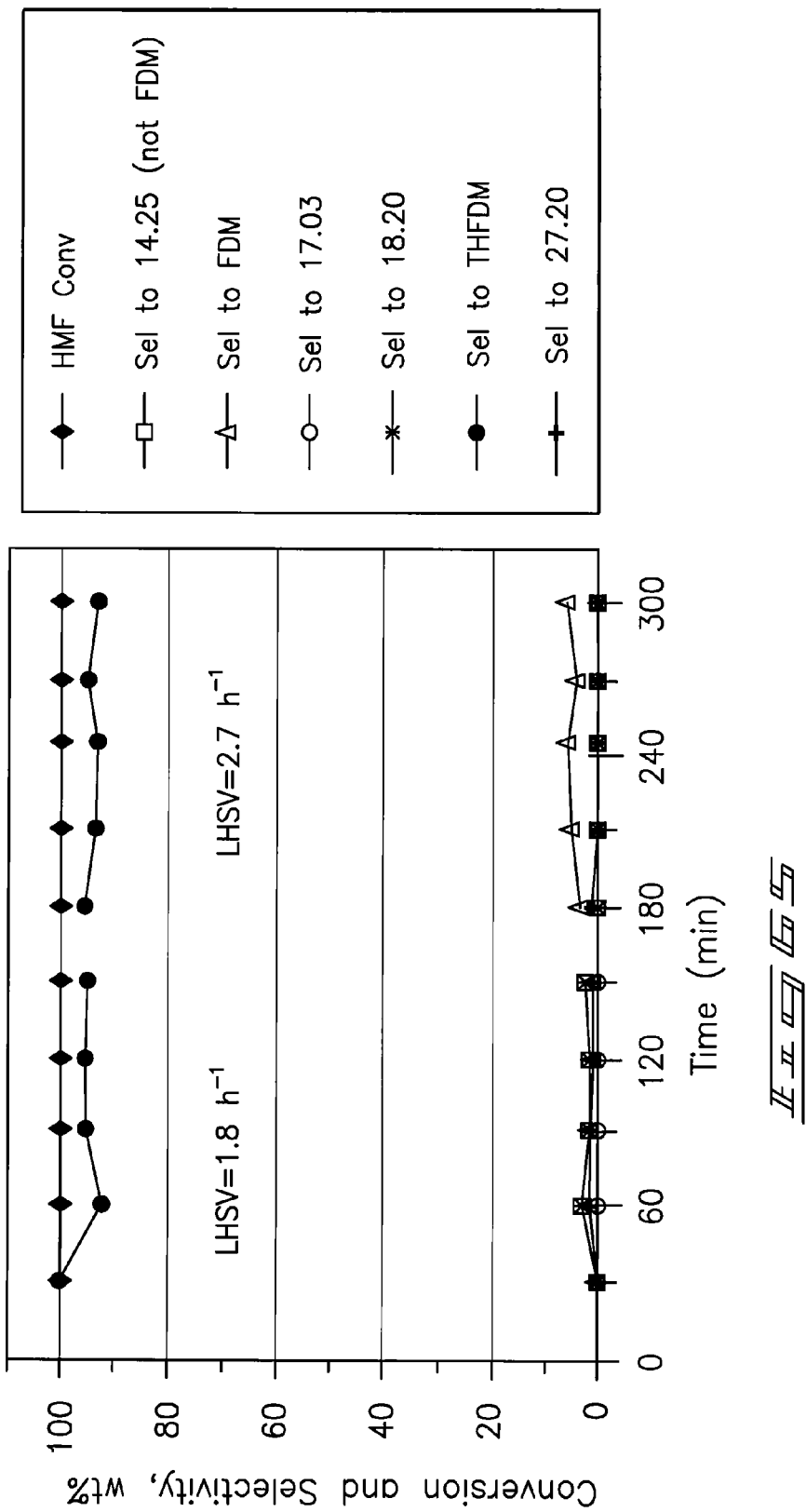
FIG. 65 shows HMF conversion as a function of time on stream utilizing the system of FIG. 62 with increased feed concentration and decreased LHSV relative to FIG. 62.
Figure 66:
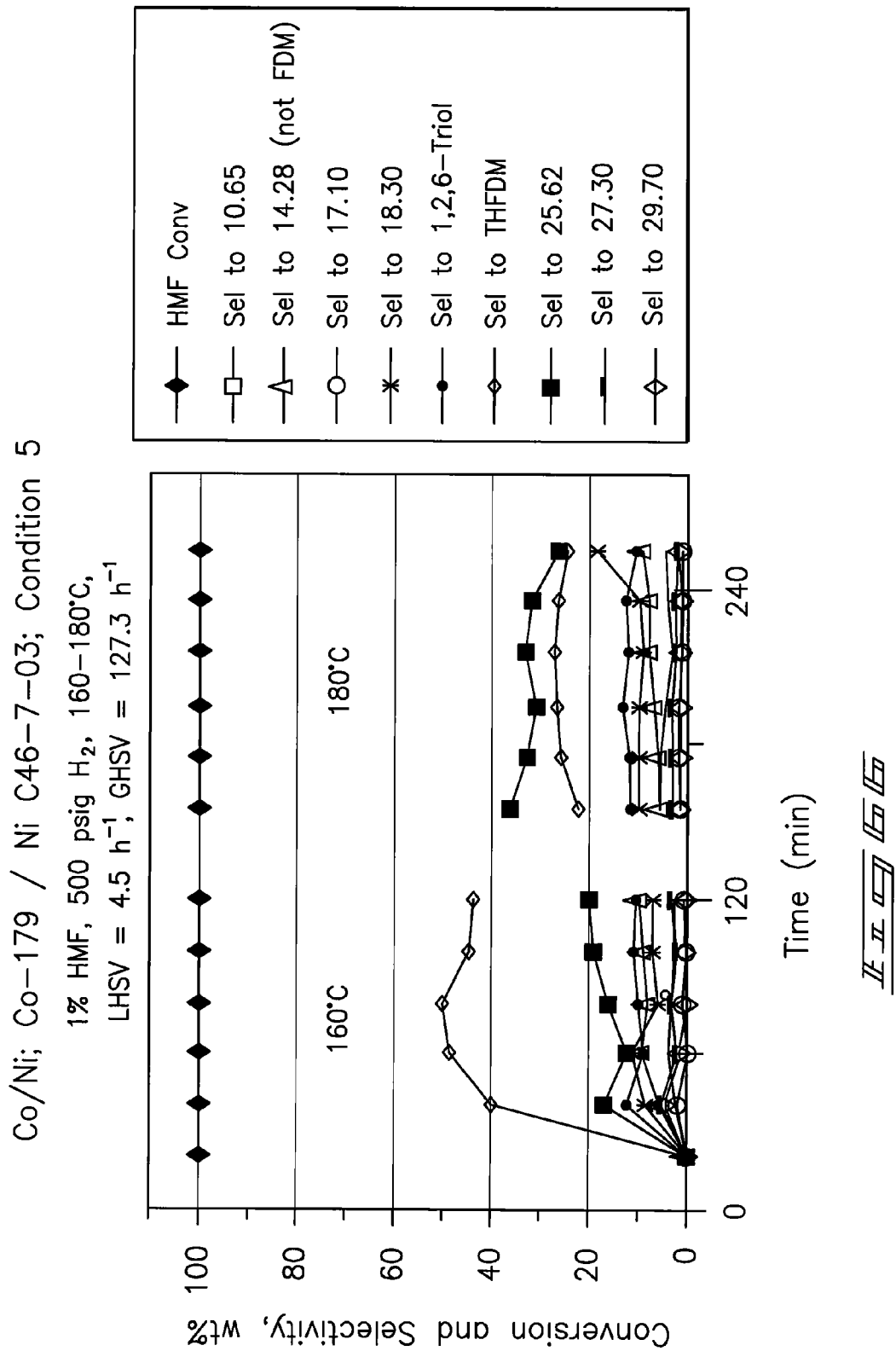
FIG. 66 shows HMF conversion as a function of time on stream utilizing the system of FIG. 62 with increased temperatures and decreased LHSV relative to FIG. 62.
Figure 67:
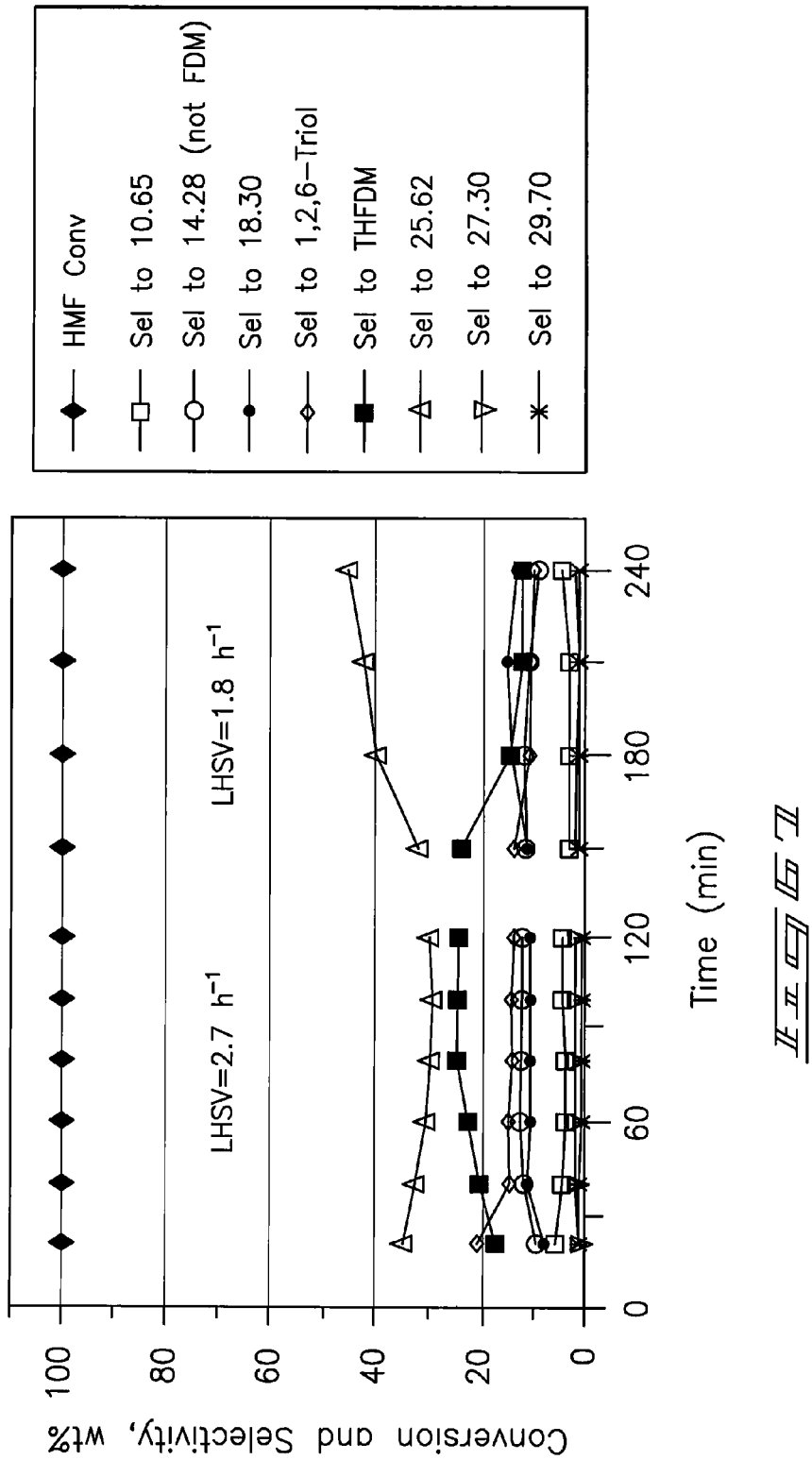
FIG. 67 shows HMF conversion as a function of time on stream utilizing the system of FIG. 62 with increased temperature and decreased LHSV relative to FIG. 62.
Figure 68:
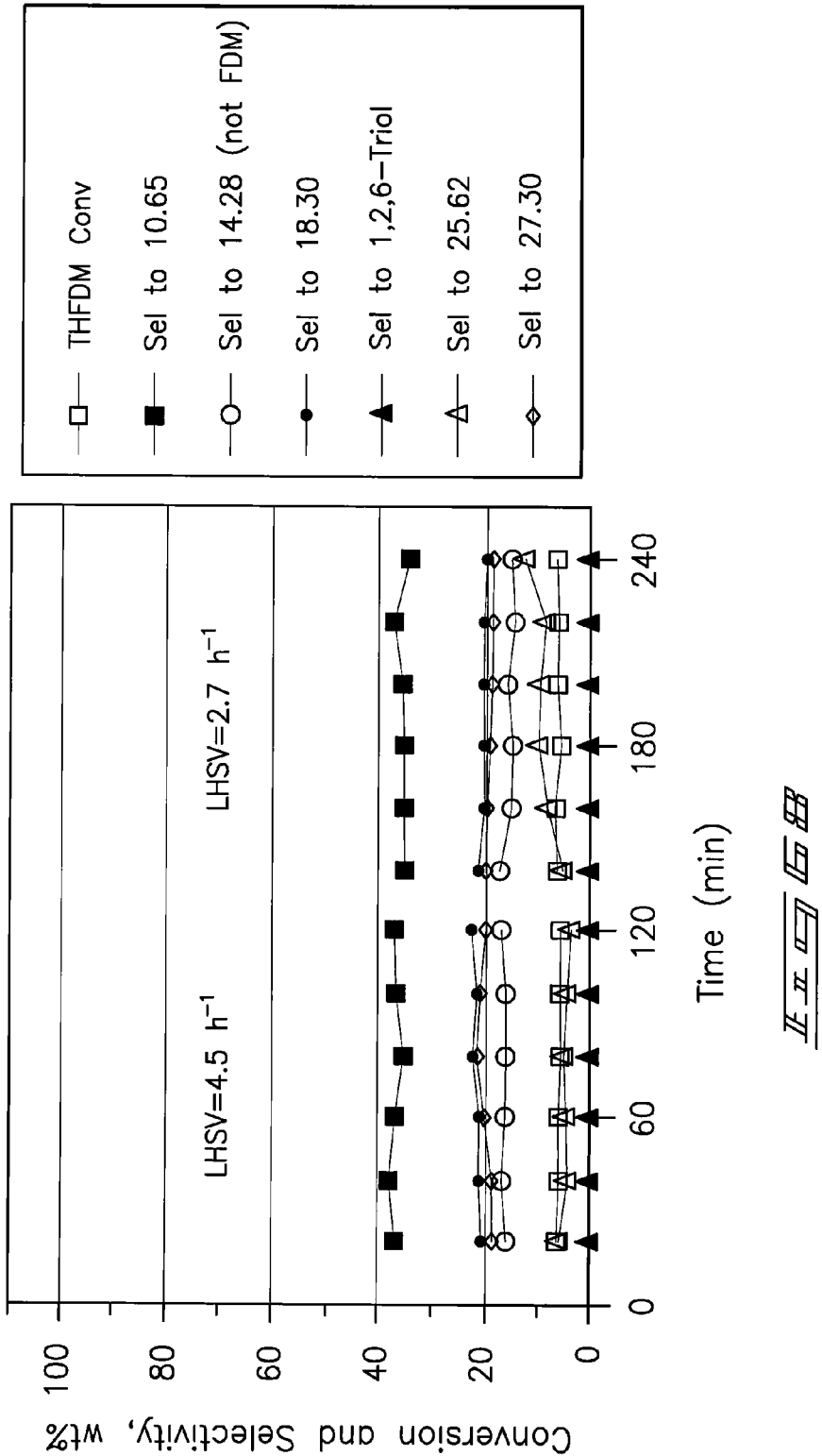
FIG. 68 shows tetrahyrofuran dimethanol (THFDM) conversion as a function of time on stream utilizing the system of FIG. 62 and increased temperature with decreased LHSV relative to FIG. 62.
Figure 69:
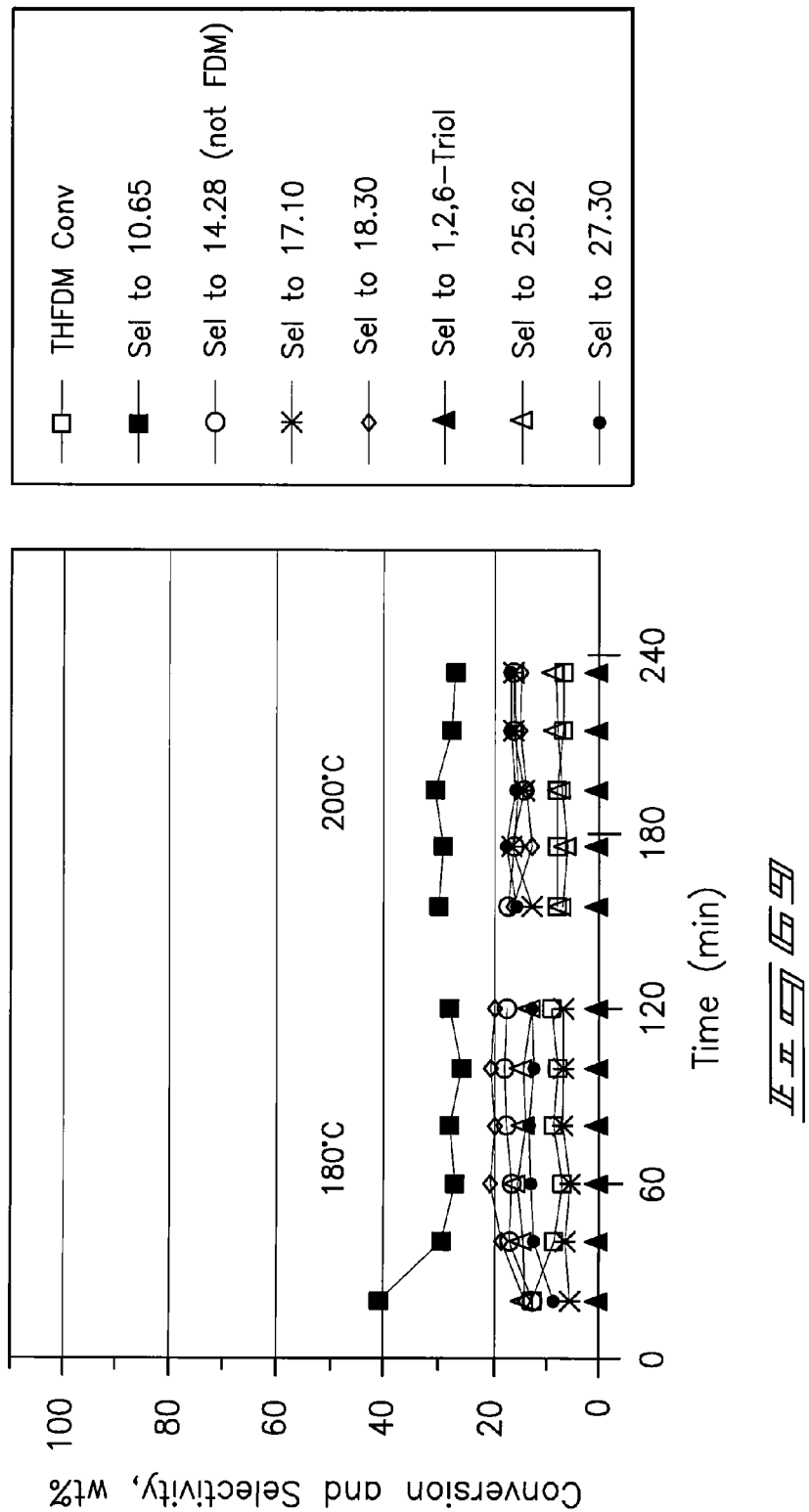
FIG. 69 shows THFDM conversion as a function of time on stream utilizing the system of FIG. 62 and increased temperature with decreased LHSV relative to FIG. 62.
Figure 70:
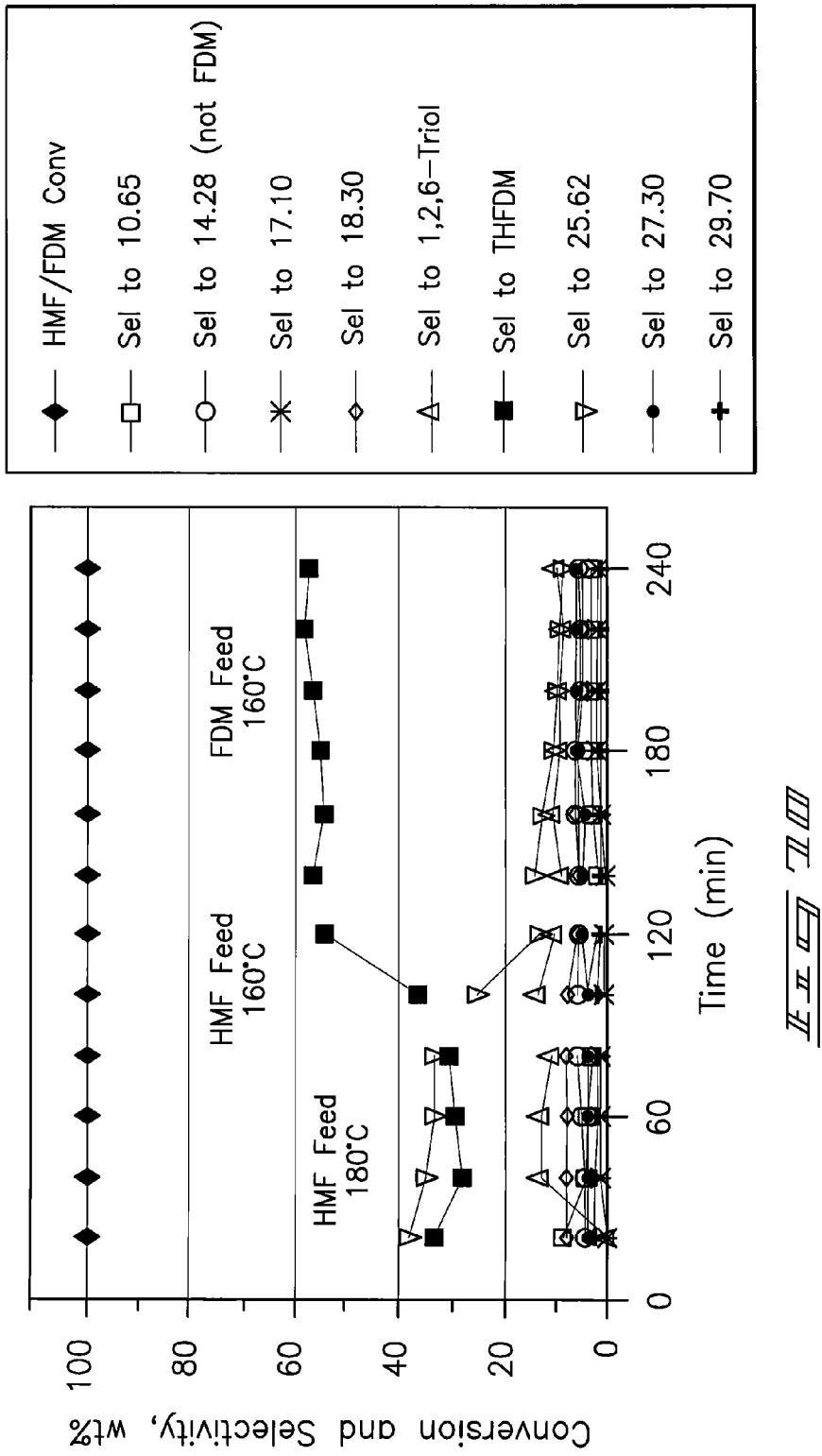
FIG. 70 shows HMF or FDM conversion as a function of time on stream utilizing the system of FIG. 62 and increased temperature with decreased LHSV relative to FIG. 62.
Figure 71:
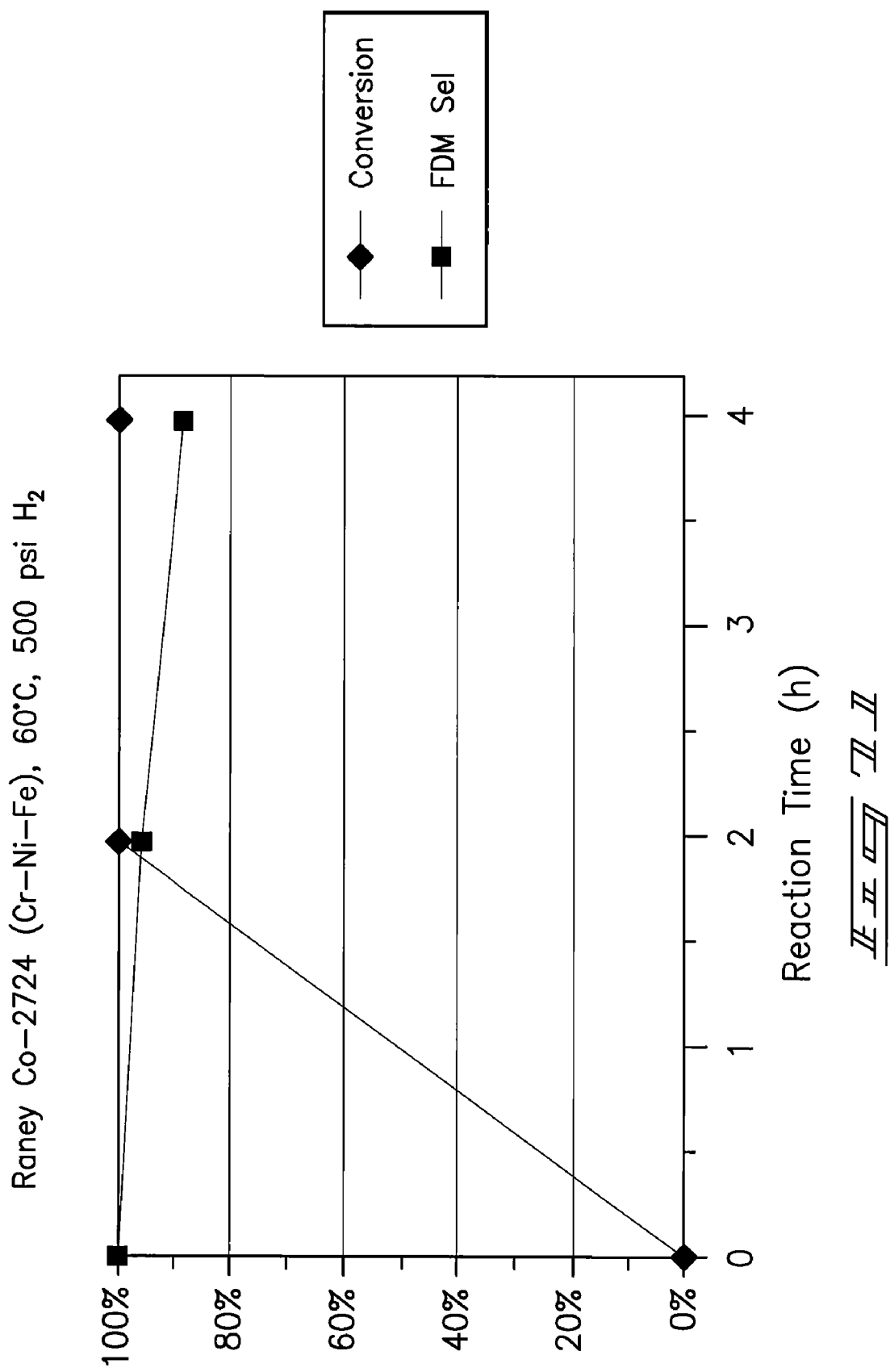
FIG. 71 shows HMF conversion and product selectivity as a function of reaction time for a batch reaction utilizing RANEY® cobalt (Cr—Ni—Fe).
Figure 72:
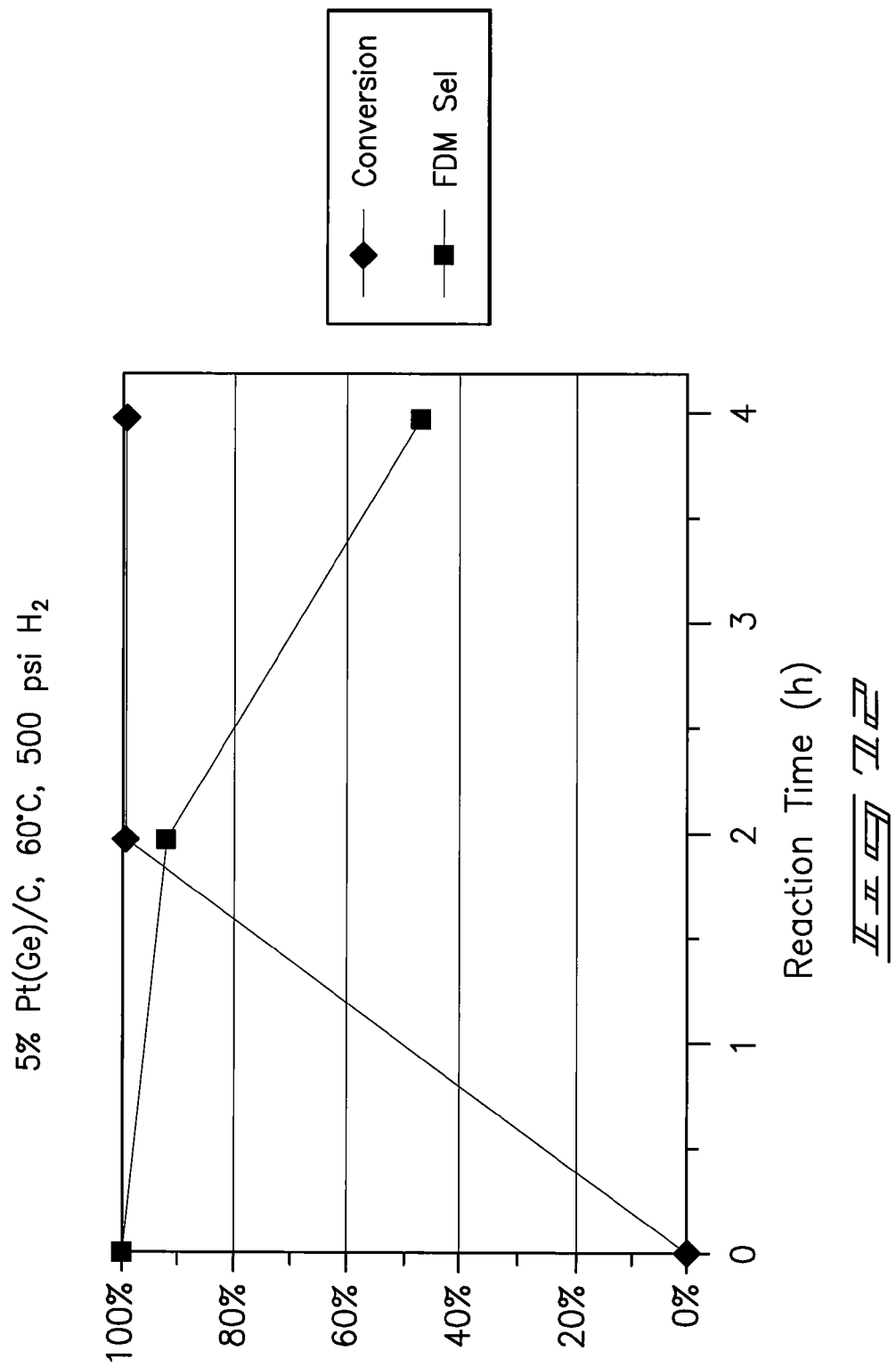
FIG. 72 shows HMF conversion and product selectivity as a function of reaction time for a batch reactor utilizing 5% Pt (Ge)/C catalyst.
Figure 73:
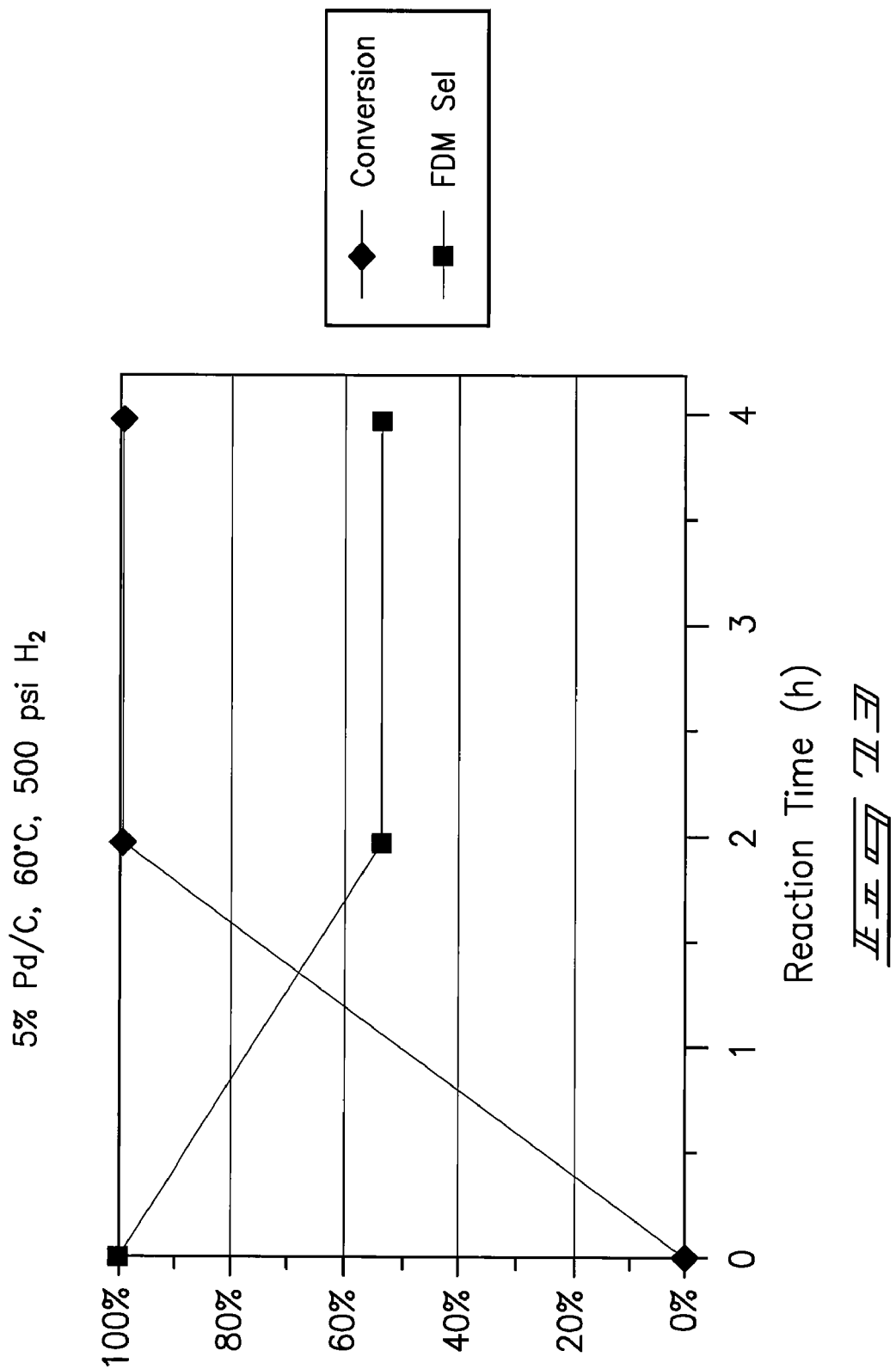
FIG. 73 shows HMF conversion and product selectivity as a function of reaction time for a batch reactor utilizing a 5% Pd/C catalyst.

Referring to FIG. 58, Ni/SiO$_2$ reduced FDM nearly quantitatively to THFDM at 70° C. However, under identical conditions utilizing HMF (FIG. 59), only 80% HMF conversion was obtained and selectivity to THFDM was about 40%. When the feed was switched again to FDM, only about 20% FDM conversion was observed (FIG. 60), indicating that HMF poisons the Ni catalyst.

A staged bed (segregated catalysts in the same bed) containing ⅓ cobalt catalyst and ⅔ nickel catalyst was tested for production of THFDM from HMF. The HMF feed first passed through the Co catalyst which primarily reduced the HMF to FDM, then through the Ni catalyst which primarily reduced the FDM to THFDM. Very high HMF conversion and selectivity to THFDM was obtained as shown in FIG. 61. The Ni catalyst appeared to remain active for THFDM production when HMF was reduced first to FDM with the Co catalyst. HMF feed concentrations of 1%, 3%, and 6%, were tested, all giving similar conversions and selectivities.

Additional experiments were conducted utilizing the staged Co/Ni catalysts at high temperatures with either HMF or FDM feeds to examine polyol production (FIGS. 62-70). Temperatures as high as 180° C. were evaluated. The major product was 1,2,6-hexanetriol but yields decreased with increased temperatures with production of may unknown products. One major by-product was identified as 2,5-hexanediol. When the feed was THFDM however, almost no ring-opening occurred. THFDM was quite stable up to 200° C. Ring-opened polyols therefore likely are formed via HMF or FDM, not via THFDM. FIGS. 62-70 show the results obtained under a variety of temperatures, feed (FDM vs. HMF) feed concentration and space velocity.

A batch-wise experiment was conducted to study the effect of organic solvent on the catalytic hydrogenation of HMF to FDM utilizing two different catalysts. Selectivity toward FDM production was compared for reactions conducted in ethanol and reactions conducted in water. As shown in Table 7, conversion and selectivity toward FDM are lower in ethanol than in water under the same reaction conditions and reaction times.

TABLE 7

Effect of Organic Solvent on HMF Reduction

| | | 60° C. 500 psi $H_2$ | | | 100° C. 950 psi $H_2$ | | |
|---|---|---|---|---|---|---|---|
| | | Time | Conversion | Selectivity | Time | Conversion | Selectivity |
| $Co/SiO_2$ | $H_2O$ | 4 hr | 100% | 96% | 1 hr | 98% | 83% |
| | EtOH | 4 hr | 1% | 16% | 1 hr | 2% | 49% |
| $Pt/Al_2O_3$ | $H_2O$ | 2 hr | 94% | 98% | 1 hr | 89% | 96% |
| | EtOH | 2 hr | 82% | 98% | 1 hr | 53% | 96% |

The impact of various impurities on the hydrogenation of HMF was investigated in both batch-wise and flow reactor studies. Impurities included fructose, ethyl acetate, dimethylacetamide, methyl t-butyl ether, methyl iso-butyl ketone, levulinic acid, formic acid, acetic acid, sodium sulfate, and N-methyl pyrrolidinone. These impurities were found to be non-detrimental to HMF conversion within the accuracy of the experiments.

Of particular interest were the results with fructose impurity in batch experiments conducted between 60 and 100° C. and 500 psi for at least 2 h. Both Pt(Ge)/C (Engelhard #43932) and $Co/SiO_2$ (Sud Chemie G62aRS) catalysts converted HMF to reduced products without reducing fructose to sorbitol or mannitol, even at high HMF conversions. FDM can be formed in high yield. In the absence of HMF, fructose is easily reduced under these reaction conditions, suggesting that HMF either inhibits fructose reduction or is reduced at a faster rate. These results indicate that highly selective reduction of HMF is possible with the HMF precursor fructose present in the feed and that fructose need not be separated from the HMF solution prior to reduction.

EXAMPLE 5

Reduction of HMF in the Presence of Fructose

Batch-wise experiments were conducted with an aqueous solution of 15 wt % each of HMF and fructose under 500 psi $H_2$ between 75 and 100° C. using Ge-promoted 5% Pt on carbon (Engelhard #43932) for at least 2 h. In a sample taken at 1 h, LC and $^{13}C$ NMR analysis showed that HMF was converted to FDM with good selectivity but that essentially no fructose was converted to sorbitol or mannitol even at high HMF conversion. Only trace amounts of levulinic and formic acids were formed.

Figure 74:
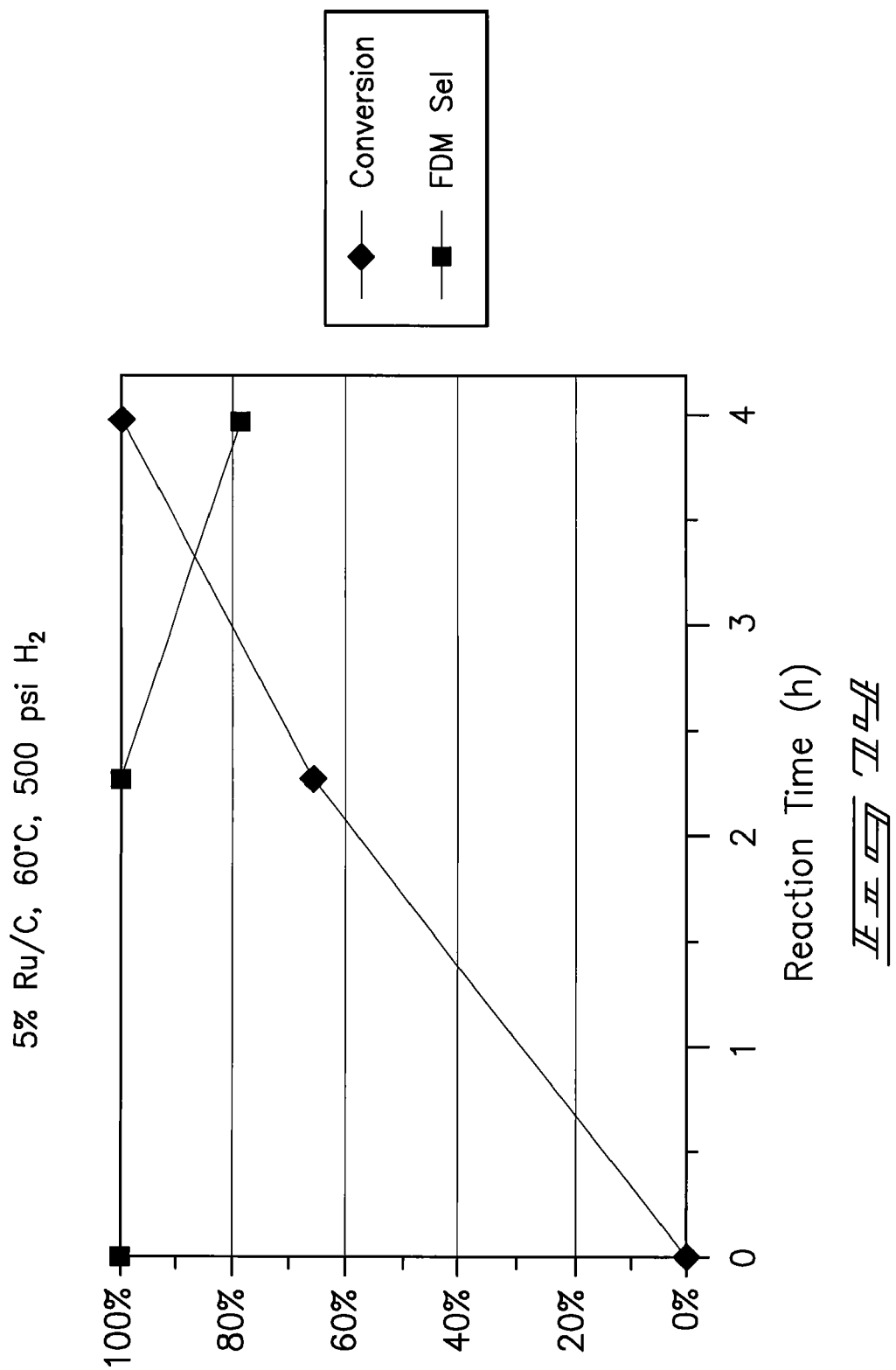
FIG. 74 shows HMF conversion and product selectivity as a function of reaction time for a batch reactor utilizing a 5% Ru/C catalyst.
Figure 75:
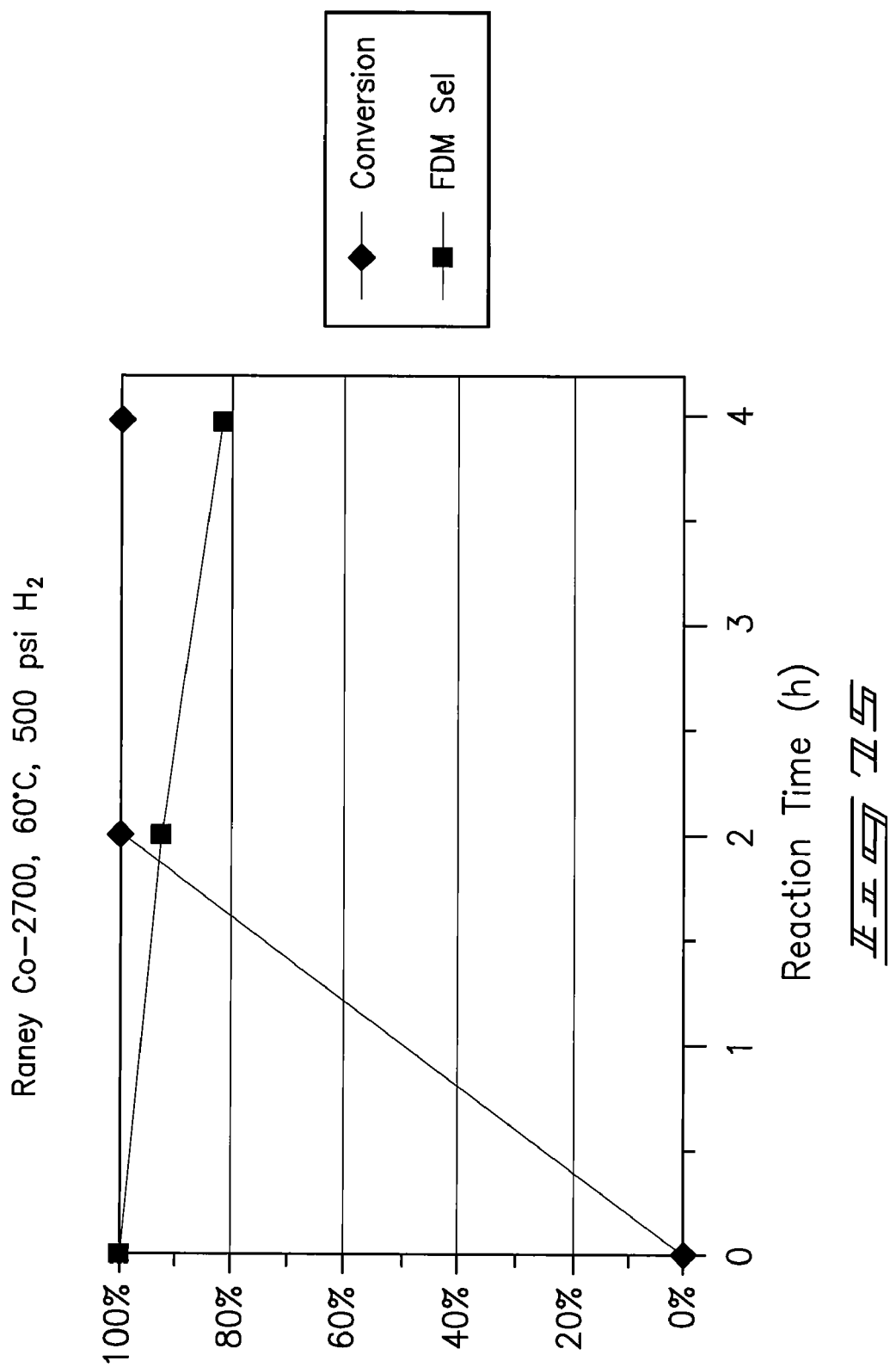
FIG. 75 shows HMF conversion and product selectivity as a function of reaction time for a batch reactor utilizing a RANEY® cobalt catalyst at 60° C.
Figure 76:
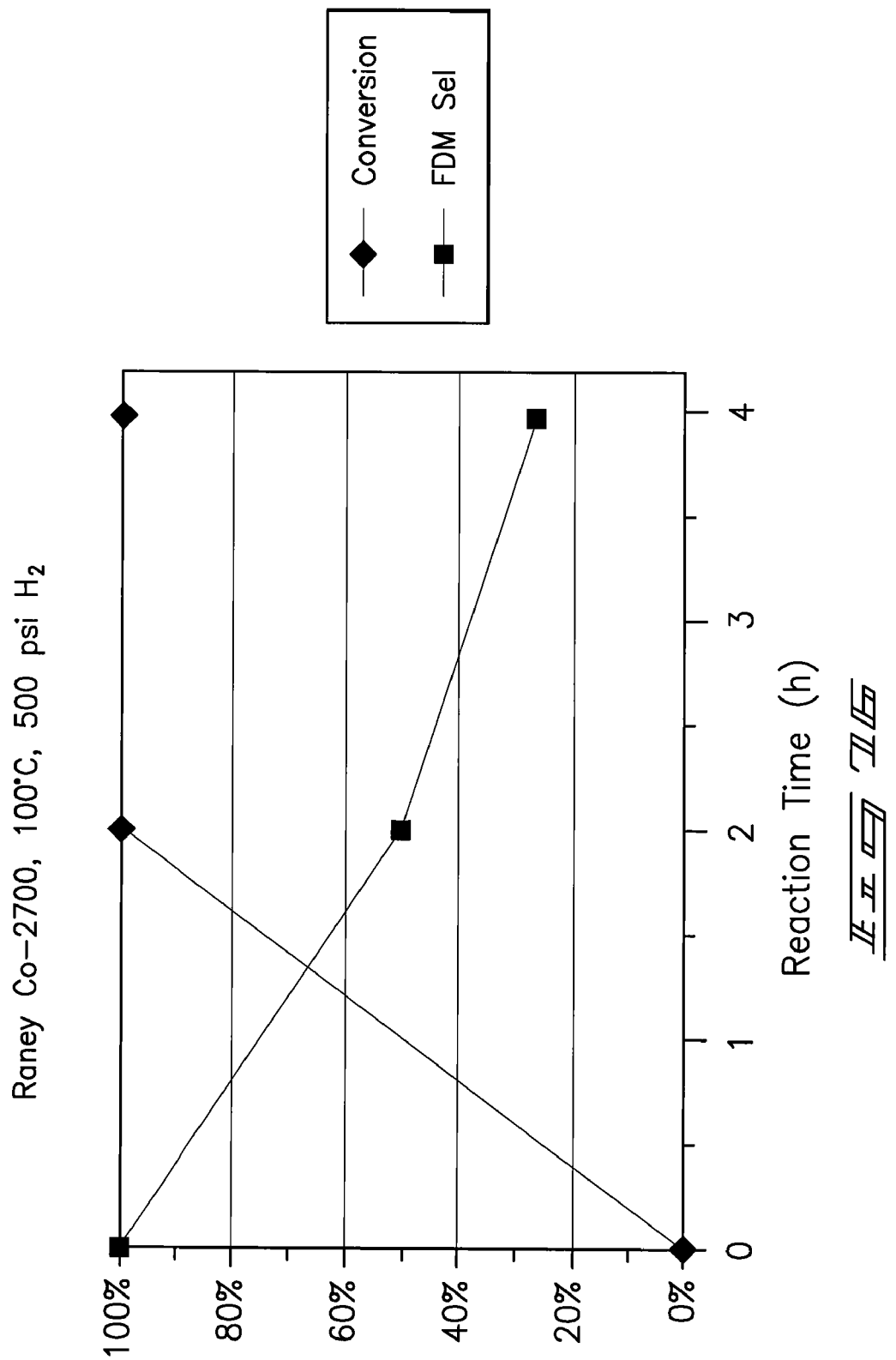
FIG. 76 shows HMF conversion and product selectivity as a function of reaction time for the catalyst of FIG. 75 at an increased temperature relative to FIG. 75.
Figure 77:
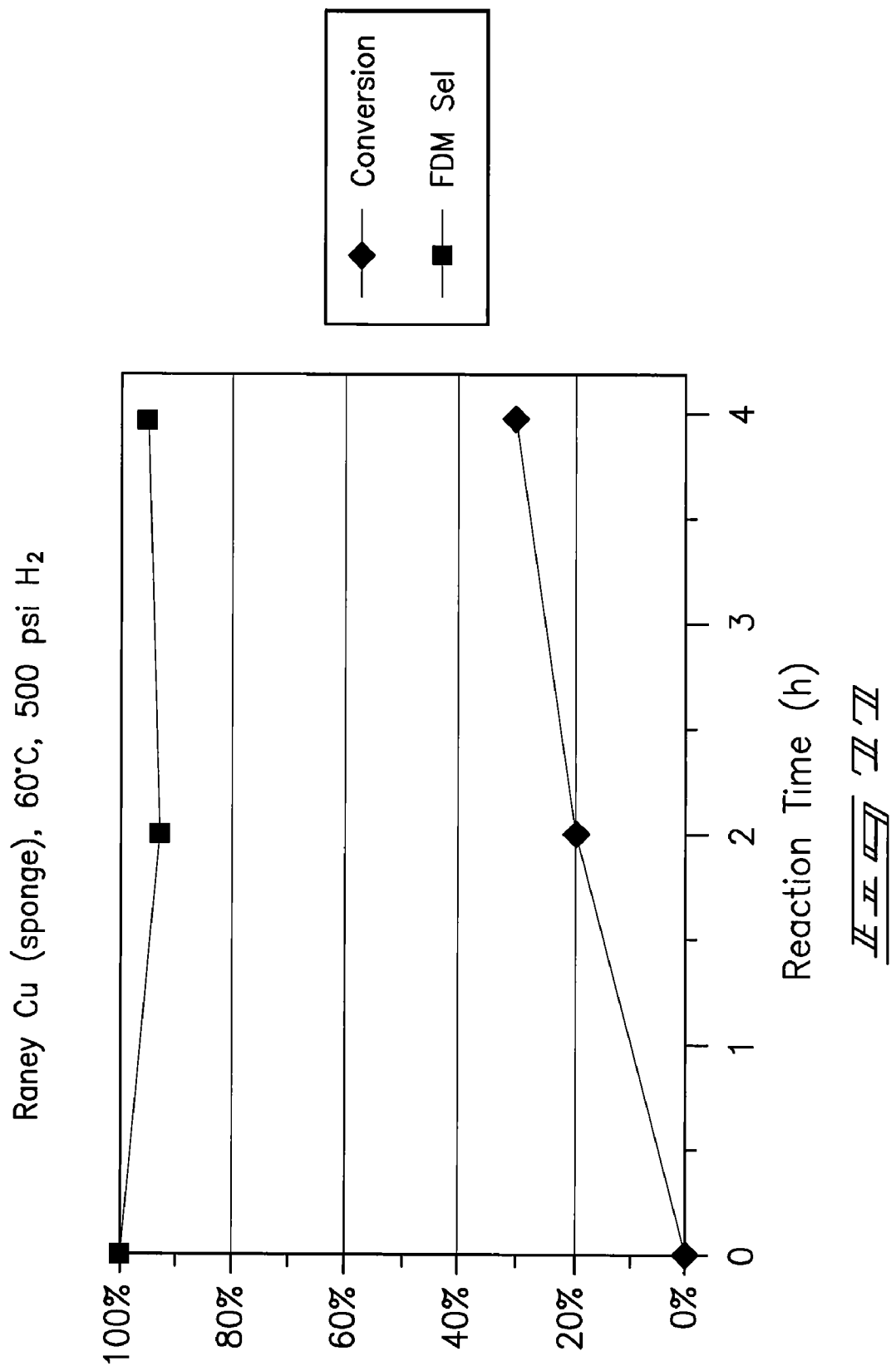
FIG. 77 shows HMF conversion and product selectivity as a function of reaction time for a batch reactor utilizing a RANEY® copper sponge catalyst.
Figure 78B:
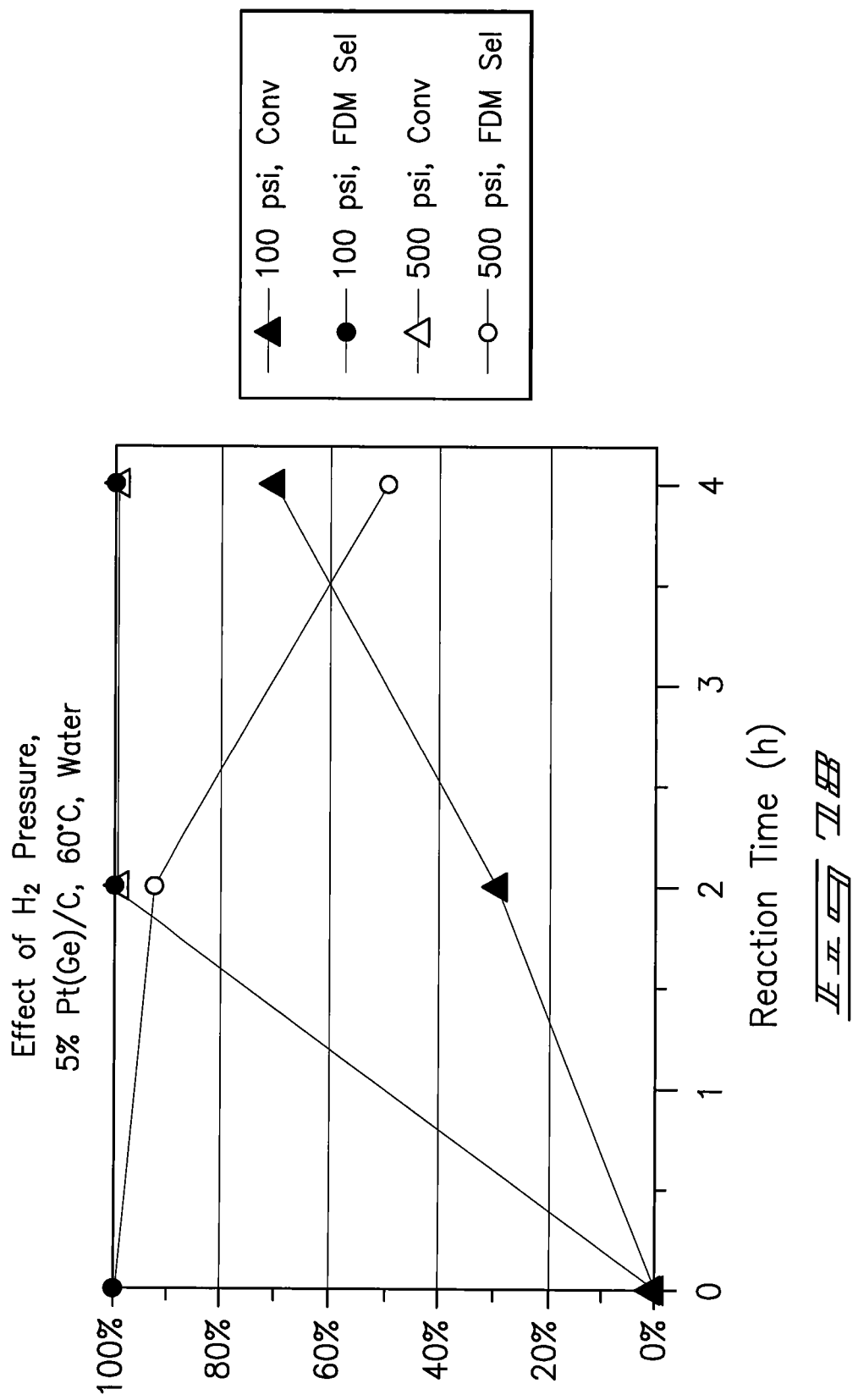
FIG. 78 shows HMF conversion and product selectivity as a function of reaction time at two different reactor pressures for a batch reactor utilizing 5% Pt (Ge)/C catalyst.
Figure 80:
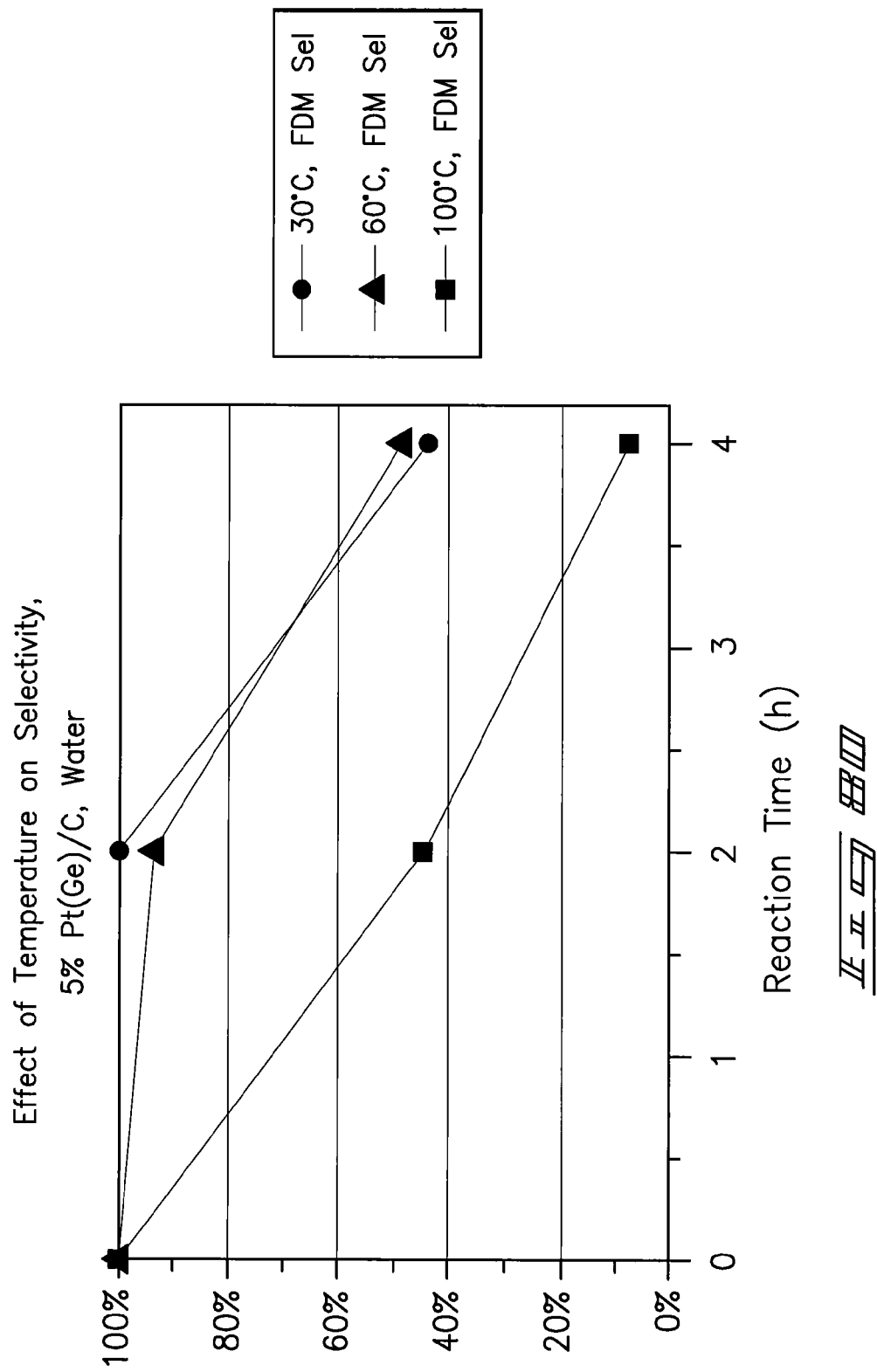
FIG. 80 shows FDM product selectivity as a function of reaction time at three different temperatures utilizing the 5% Pt (Ge)/C catalyst of FIG. 79.

FIGS. 71-80 show the results of a number of batchwise HMF conversion reactions utilizing RANEY® Co-2724 (FIG. 71); 5% Pt(Ge)/C (FIG. 72); 5% Pd/C (FIG. 73); 5% Ru/C (FIG. 74); RANEY® Co-2700 (FIGS. 75-76); and RANEY® Cu (FIG. 77) catalysts. The effect of $H_2$ pressure was investigated utilizing a 5% Pt(Ge)/C catalyst as shown in FIG. 78. FIG. 79 shows the effect of temperature on HMF conversion using the Pt(Ge)/C catalyst, and FIG. 80 shows the effect of temperature on FDM selectivity for the Pt(Ge)/C catalyst.

Reaction methods of the invention for selective reduction of HMF to produce FDM and/or THF dimethanol have many advantages relative to conventional technologies. The reaction temperature of the inventive methodology is relatively low, thereby reducing unwanted side reactions and decomposition of reactants and/or products, and allowing increased selectivity. The hydrogen pressure is also low resulting in reduced operating costs. Since the solvent utilized is water rather than an organic solvent, the methodology is relatively less expensive and more environmentally friendly than many conventional processes. The reaction rates obtained through the methodology of the invention are high, allowing highly efficient continuous flow reactors to be utilized.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of reducing hydroxymethylfurfural (HMF), comprising:
   providing both HMF and water into a reactor to form a reactant mixture comprising HMF and water;
   providing $H_2$ into the reactor; and
   contacting the reactant mixture with a catalyst comprising at least one metal selected from Ni, Co, Cu, Pd, Pt, Ru, Ir, Re and Rh, the contacting being conducted while maintaining the temperature of the reactant mixture below or equal to 250° C., the contacting reducing the HMF.

2. The method of claim 1 wherein the temperature of the reactant mixture is maintained below or equal to 180° C. during the contacting.

3. The method of 1 wherein the temperature of the reactant mixture is maintained below or equal to 70° C. during the contacting.

4. The method of claim 1 wherein the temperature of the reactant mixture is maintained below or equal to 60° C. during the contacting.

5. The method of claim 1 wherein the catalyst further comprises one or more metal selected from the group consisting of Ni, Rh, Cu, Ca, Cr, Ru, Mn, Ag, Au, In, S, Fe, Re, Sn, Ge, Ir, Pd, Pt, Cd, Ga, Mo, Zn, Al, and Bi.

6. The method of claim 1 wherein the reactor is a continuous flow reactor, and wherein the providing both HMF and water into the reactor comprises flowing the reactant mixture as a feed stream into the reactor.

7. The method of claim 6 further comprising purging one or more of the HMF, the water, or the $H_2$ from the reactor with inert gas.

8. The method of claim 1 further comprising reducing at least a portion of the HMF to form tetrahydrofuran dimethanol.

9. The method of claim 1 further comprising reducing at least a portion of the HMF to form furandimethanol (FDM).

10. The method of claim 9 wherein the converting produces FDM as the major product.

11. The method of claim 1 wherein the catalyst comprises Co on an inorganic support material.

12. The method of claim 1 wherein the catalyst comprises Cu-chromite.

13. The method of claim 1 wherein the catalyst comprises Pd on a carbon support material.

14. The method of claim 1 wherein the catalyst comprises Pt on an inorganic support material.

* * * * *

UNITED STATES PATENT AND TRADEMARK OFFICE
CERTIFICATE OF CORRECTION

PATENT NO. : 8,367,851 B2
APPLICATION NO. : 13/173942
DATED : February 5, 2013
INVENTOR(S) : Michael A. Lilga et al.

It is certified that error appears in the above-identified patent and that said Letters Patent is hereby corrected as shown below:

In the Specifications:

Column 12, line 29 – Replace "sere conducted" with --were conducted--

Column 12, line 63 – Replace "may unknown" with --many unknown--

Signed and Sealed this
Twenty-fifth Day of June, 2013

Teresa Stanek Rea
*Acting Director of the United States Patent and Trademark Office*